(12) United States Patent
Holoshitz et al.

(10) Patent No.: US 7,074,893 B2
(45) Date of Patent: Jul. 11, 2006

(54) METHODS AND COMPOSITIONS FOR THE TREATMENT OF DISEASES ASSOCIATED WITH SIGNAL TRANSDUCTION ABERRATIONS

(75) Inventors: Joseph Holoshitz, Ann Arbor, MI (US); Song Ling, Ypsilanti, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/786,774

(22) Filed: Feb. 25, 2004

(65) Prior Publication Data

US 2004/0236071 A1    Nov. 25, 2004

Related U.S. Application Data

(63) Continuation of application No. 10/161,959, filed on Jun. 3, 2002.

(51) Int. Cl.
*A61K 38/04*    (2006.01)
(52) U.S. Cl. ........................... 530/330; 530/300
(58) Field of Classification Search ............... 530/330, 530/300
See application file for complete search history.

(56) References Cited

U.S. PATENT DOCUMENTS

| | | | |
|---|---|---|---|
| 4,552,891 A | 11/1985 | Ho et al. | 514/443 |
| 4,588,394 A | 5/1986 | Schulte et al. | 604/9 |
| 4,902,505 A | 2/1990 | Pardridge et al. | 424/85.7 |
| 5,004,697 A | 4/1991 | Pardridge | 436/547 |
| 5,051,448 A | 9/1991 | Shashoua | 514/547 |
| 5,130,129 A | 7/1992 | Pardridge | 424/85.8 |
| 5,147,855 A | 9/1992 | Gozes et al. | 514/12 |
| 5,166,320 A | 11/1992 | Wu et al. | 530/395 |
| 5,169,862 A | 12/1992 | Burke et al. | 514/450 |
| 5,192,746 A | 3/1993 | Lobl et al. | 514/11 |
| 5,354,844 A | 10/1994 | Beug et al. | 530/345 |
| 5,393,773 A | 2/1995 | Craig et al. | 514/415 |
| 5,525,727 A | 6/1996 | Bodor | 546/39 |
| 5,539,085 A | 7/1996 | Bischoff et al. | 530/350 |
| 5,554,639 A | 9/1996 | Craig et al. | 514/415 |
| 5,559,103 A | 9/1996 | Gaeta et al. | 514/54 |
| 5,576,423 A | 11/1996 | Aversa et al. | 530/388.75 |
| 5,601,835 A | 2/1997 | Sabel et al. | 424/424 |
| 5,618,803 A | 4/1997 | Bodor | 514/81 |
| 5,624,894 A | 4/1997 | Bodor | 514/2 |
| 5,643,207 A | 7/1997 | Rise | 604/93 |
| 5,670,477 A | 9/1997 | Poduslo et al. | 514/2 |
| 5,801,161 A | 9/1998 | Merkus | 514/52 |
| 5,864,037 A | 1/1999 | Chasin et al. | 544/118 |
| 5,869,479 A | 2/1999 | Kreutner et al. | 514/212 |
| 5,972,883 A | 10/1999 | Gozes et al. | 514/12 |
| 6,042,579 A | 3/2000 | Elsberry et al. | 604/891.1 |
| 6,117,454 A | 9/2000 | Kreuter et al. | 424/490 |
| 6,132,764 A | 10/2000 | Li et al. | 424/450 |
| 6,153,193 A | 11/2000 | Kabanov et al. | 424/184.1 |
| 6,153,200 A | 11/2000 | Carson et al. | 424/201.1 |
| 6,172,277 B1 | 1/2001 | Tate et al. | 800/12 |
| 6,179,826 B1 | 1/2001 | Aebischer et al. | 604/522 |
| 6,753,314 B1 * | 6/2004 | Giot et al. | 514/12 |

FOREIGN PATENT DOCUMENTS

| | | |
|---|---|---|
| WO | WO 90/14835 | 12/1990 |
| WO | WO 97/34002 | 9/1997 |

OTHER PUBLICATIONS

Chen et al. (Jun. 15, 1992) "Studies of cloned 37-kDa subunit of activator 1 (replication factor C) of HeLa cells". Proc Natl Acad Sci USA 89(12): 5211-5.*

Auger I et al., "HLA-DR4 and HLA-DR10 Motifs That Carry Susceptibility To Rheumatoid Arthritis Bind 70-kD Heat Shock Proteins," *Nature Med* 2:306-310 (1996).

Basu S. et al., "CD91 is a common receptor for heat shock proteins gp96, hsp70, and calreticulin," *Immunity* 14: 303-313 (2001).

Benvenisty and Reshef, "Direct introduction of genes into rats and expression of the genes" *Proc. Nat. Acad. Sci. USA*, 83:9551-55 (1986).

Bickel et al., "Pharmacologic effects *in vivo* in brain b yvector-mediated peptide drug delivery, " *Proc. Natl. Acad. Sci. USA* 90:2618-2622 (1993).

Borisova et al., "Behavior of a Short preSI Epitope on the Surface of Hepatitis B Core Particles, " *Biol Chem* 380:315-324 (1999).

Colaco CB et al., "Deficient repair of $O^6$-methylguanine in lympocytes from rheumatoid arthritis may be and acquired defect, "*Clin Exp Immunol* 72:15-19 (1988).

Corder EH et al., "Gene Dose of Apolipoprotein E Type 4 Allele and the Risk of Alzheimer's Disease in Late Onset Families, "*Science* 261:921-923 (1993).

Corder EH et al., "Protective effect of apolipoprotein E type 2 allele for late on onset Alzheimer disease, " *Nat Genet* 7:180-184 (1994).

Curran M et al., "HLA-DR antigens associated with major genetic risk for late-onset Alzheimer's disease, "*NeuroReport* 8:1467-1469 (1997).

Dubensky et al., "Direct transfection of viral and plasmid DNA into the liver or spleen of mice, " *Proc. Nat. Acad. Sci. USA* , 81:7529-33 (1984).

(Continued)

*Primary Examiner*—Janet L. Andres
*Assistant Examiner*—Steven H. Standley
(74) *Attorney, Agent, or Firm*—Medlen & Carroll, LLP

(57) ABSTRACT

The present invention relates generally to therapeutic methods and compositions. More particularly, methods and compositions to counteract and reverse disease-causing signaling defects in diseases with underlying signal transduction aberrations, including but not limited to Alzheimer's Disease.

14 Claims, 19 Drawing Sheets

OTHER PUBLICATIONS

Eldred et al., "Orally Active Non-Peptide Fibrinogen Receptor (Gpllb/llla) Antagonists: Identification of 4-[4-[4-(Aminoiminomethyl)phenyl]-1-piperazinyl]-1-piperidineacetic Acid as a Long-Acting, Broad-Spectrum Antithrombotic Agent, "*J. Med. Chem.* 37:3882 (1994).

Fisher et al., "(±)-cis-2-Methyl-spiro (1,3-oxathiolane-5,3') quinuclidine (AF102B): a new $M_1$ agonist attenuates cognitive dysfunctions in AF64-treated rats, "*Neurosci Lett* 102:325-331 (1989).

Forsythe and Westbrooke, "Slow Excitatory Postsynaptic Currents Mediated By N-Methyl-D-Asparate Receptors On Cultured Mouse Central Neurones, "*J Physiol* (Lond) 396:515-533 (1988).

Galea E and Feinstein DL., "Regulation of the expression of the inflammatory nitric oxide synthase (NOS2) by cyclic AMP, "*FASEB J* 13:2125-2137 (1999).

Greegersen PK et al., "The Share Epitope Hypothesis: An Approach to Understanding The Molecular Genetics of Susceptibility to Rheumatoid Arthritis, "*Atrhritis Rheum* 30:1205-1213 (1987).

Ku et al., "Potent Non-peptide Fibrinogen Receptor Antagonists Which Present An Alternative Pharmacohore, "*J. Med. Chem.* 38:9 (1995).

Levitzki A., "Targeting signal transduction for disease therapy, " *Curr Opin Cell Biol* 8:239-244 (1996).

Linden et al., "Characterization of Human $A_B$ Adenosine Receptors: Radiogland Binding, Western Blotting, and Coupling to $G_q$ in Human Embryonic Kidney 293 Cells and HMC-1 Mast Cells, "*Molecular Pharmacology* 56:705-713 (1999).

Lipman and Pearson, "Rapid and Sensitive Protein Similarity Searches, "*Science* 227:1435-1441 (1985).

McCurdy D et al., "Delayed Repair of DNA Damage by Ionizing Radiation in Cells from Patients with Juvenile Systemic Lupus Erythematosus and Rheumatoid Arthritis, " *Radiat Res* 147:48-54 (1997).

Nepom GT et al., "HLA Genes Associated With Rheumatoid Arthritis: Identification of Susceptibility Alleles Using Specific Oligonucleotide Probes, " *Arthritis Rheum* 32:15-21 (1989).

Pearson and Lipman, "Improved tools for biological Sequence comparison, "*Proc. Natl. Acad. Sci. (USA)* 85:2444-2448 (1988).

Pericak-Vance MA et al., "Linkage Studies in Familial Alzheimer Disease: Evidance for Chromosome 19 Linkage, "*Am J Hum Genet* 48:1034-1050 (1991).

Pumpens P and Grens E., "Hepatitis B core particles as a universal display model: a structure-function basis for development, "*FEBS Lett* 442:1-6 (1999).

Strittmatter WJ and Roses AD, "Apolipoprotein E and Alzheimer disease, " *Proc Natl Acad Sci USA* 92:4725-4727 (1995).

Wagner, et al., "Transferin-polycation-DNA complexes: The effect of polycations on the structure of the complex and DNA delivery to cells, " *Proc. Natl. Acad. Sci.*, 88:4255-4259 (1991).

Weisgraber KH., "Apolipoprotein E distribution among human plasma lioproteins: role of the cysteine-arginine interchange at residue 112, " *J Lipid Res* 31:1503-1511 (1990).

Weyand CM et al., "The Influence of HLA-DRBI Genes on Disease Severity in Rheumatoid Arthritis, " *Ann Intern Med* 117:10 801-806 (1992).

Wolff et al., "Direct Gene Transfer Into Mouse Muscle in Vivo, " *Science*, 247: 1456-68 (1990).

Walker et al., "Proteopathy: The next therapeutic frontier?," *Curr Opin Investig Drugs*, 3(5):782-787 (2002).

Fitjohn et al., "Age-related impairment of synaptic transmission but normal long-term potentiation in transgenic mice that overexpress the human APP695SWE mutant form of amyloid precursor protein, "*J. Neuroscience*, 21(13):4691-4698 (2001).

Chapman et al., "Impaired synaptic plasticity and learning in aged amyloid precursor protein transgenic mice,"*Nature Neuroscience*, 2:271-276 (1999).

Schenk et al., "Potential treatment oppertunities for alzheimer's disease through inhibition of secretases and Aβ immunization, "*J. Mole. Neuroscience*,17:259-267 (2001).

Perdriger et al., "Role of HLA-DR-DR and DR-DQ associations in the expression of extraarticular manifestations and rheumatoid factor in rheumatoid arthritis, "*J. Rheumatology*, 24(7):1272-1276 (1997).

Auger et al., "A function for the QKRAA amino acid motif: mediating binding of DnaJ to DnaK, " *J. Clin Invest*, 99(8):1818-1822 (1997).

Singal et al., "Genetics of rheumatoid arthritis (RA): two separate regions in the major histocompatibility compex contribute to suscepitibility to RA, "*Immunology Letters*, 69:301-306 (1999).

Vitolo et al., "Amyloid β-peptide inhibition of the PKA/CREB pathway and long-term potentation: reversibility by drugs that enhance cAMP signaling, " *PNAS*, 99(20):13217-13221 (2002).

Sun et al., "Bilateral injection of isoproterenol into hippocampus induces alzheimers-like hyperphosphorylation of tau and spatial memory deficit in rat, "*FEBS Letters*, 579:251-258 (2005).

Gong et al., "Persistent improvement in synaptic and congnitive functions in an alzheimer mouse model after rolipram treatment, "*J. Clin. Invest.*, 114 (11):1624-1634 (2004).

* cited by examiner

| | | | |
|---|---|---|---|
| HLA-DRβ*0401 | $X_n$QKRAAX$_n$ | Xaa$_n$Gln Lys Arg Ala AlaXaa$_n$ | [SEQ ID NO:28] |
| *0402 | $X_n$DERAAX$_n$ | Xaa$_n$Asp Glu Arg Ala AlaXaa$_n$ | [SEQ ID NO:29] |
| *0403 | $X_n$QRRAEX$_n$ | Xaa$_n$Gln Arg Arg Ala GluXaa$_n$ | [SEQ ID NO:30] |
| *0404 | $X_n$QRRAAX$_n$ | Xaa$_n$Gln Arg Arg Ala AlaXaa$_n$ | [SEQ ID NO:31] |
| H. Laminin β2 | $X_n$QRRAAX$_n$ | Xaa$_n$Gln Arg Arg Ala AlaXaa$_n$ | [SEQ ID NO:31] |
| M. Laminin β2 | $X_n$QRRTAX$_n$ | Xaa$_n$Gln Arg Arg Thr AlaXaa$_n$ | [SEQ ID NO:32] |
| APLP1 | $X_n$QRRAAX$_n$ | Xaa$_n$Gln Arg Arg Ala AlaXaa$_n$ | [SEQ ID NO:31] |
| ApoE ε4 | $X_n$QKRLAX$_n$ | Xaa$_n$Gln Lys Arg Leu AlaXaa$_n$ | [SEQ ID NO:33] |
| ε3 | $X_n$QKRLAX$_n$ | Xaa$_n$Gln Lys Arg Leu AlaXaa$_n$ | [SEQ ID NO:33] |
| ε2 | $X_n$QKCLAX$_n$ | Xaa$_n$Gln Lys Cys Leu AlaXaa$_n$ | [SEQ ID NO:34] |

FIG. 7

HBc*0401 [SEQ ID NO:17]

MDIDPYKEFGATVELLSFLPSDFFPSVRDLLDNASALYREALESPEHCSPHHTALRQAILCWGELMTLATWVGGNLED
HKDLLEQKRAAVDTYCVDPISRDLVVSYVNTNMGLKFRQLLWFHISCLTFGRETVIEYLVSFGVWIRTPPAYRPPNAP
ILSTLPAWARVIN

Met Asp Ile Asp Pro Tyr Lys Glu Phe Gly Ala Thr Val Glu Leu Leu Ser Phe Leu Pro
Ser Asp Phe Phe Pro Ser Val Arg Asp Leu Leu Asp Asn Ala Ser Ala Leu Tyr Arg Glu
Ala Leu Glu Ser Pro Glu His Cys Ser Pro His His Thr Ala Leu Arg Gln Ala Ile Leu
Cys Trp Gly Glu Leu Met Thr Leu Ala Thr Trp Val Gly Gly Asn Leu Glu Asp His Lys
Asp Leu Leu Glu Gln Lys Arg Ala Ala Val Asp Thr Tyr Cys Val Asp Pro Ile Ser Arg
Asp Leu Val Val Ser Tyr Val Asn Thr Asn Met Gly Leu Lys Phe Arg Gln Leu Leu Trp
Phe His Ile Ser Cys Leu Thr Phe Gly Arg Glu Thr Val Ile Glu Tyr Leu Val Ser Phe
Gly Val Trp Ile Arg Thr Pro Pro Ala Tyr Arg Pro Pro Asn Ala Pro Ile Leu Ser Thr
Leu Pro Ala Trp Ala Arg Val Ile Asn

FIG. 11 A

HBC*0402 [SEQ ID NO:18]

MDIDPYKEFGATVELLSFLPSDFFPSVRDLLDNASALYREALESPEHCSPHHTALRQAILCWGELMTLATWVGGNLED
HKDILEDERAAVDTYCVDPISRDLVVSYVNTNMGLKFRQLLWFHISCLTFGRETVIEYLVSFGVWIRTPPAYRPPNAP
ILSTLPAWARVIN

Met Asp Ile Asp Pro Tyr Lys Glu Phe Gly Ala Thr Val Glu Leu Leu Ser Phe Leu Pro

Ser Asp Phe Phe Pro Ser Val Arg Asp Leu Leu Asp Asn Ala Ser Ala Leu Tyr Arg Glu

Ala Leu Glu Ser Pro Glu His Cys Ser Pro His His Thr Ala Leu Arg Gln Ala Ile Leu

Cys Trp Gly Glu Leu Met Thr Leu Ala Thr Trp Val Gly Gly Asn Leu Glu Asp His Lys

Asp Ile Leu Glu Asp Glu Arg Ala Ala Val Asp Thr Tyr Cys Val Asp Pro Ile Ser Arg

Asp Leu Val Val Ser Tyr Val Asn Thr Asn Met Gly Leu Lys Phe Arg Gln Leu Leu Trp

Phe His Ile Ser Cys Leu Thr Phe Gly Arg Glu Thr Val Ile Glu Tyr Leu Val Ser Phe

Gly Val Trp Ile Arg Thr Pro Pro Ala Tyr Arg Pro Pro Asn Ala Pro Ile Leu Ser Thr

Leu Pro Ala Trp Ala Arg Val Ile Asn

FIG. 11 A Cont.

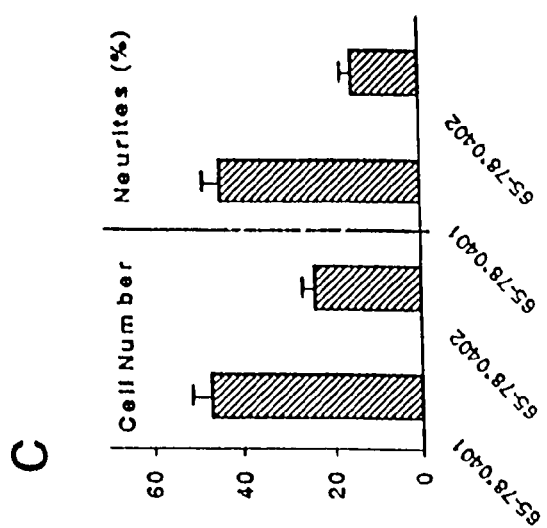
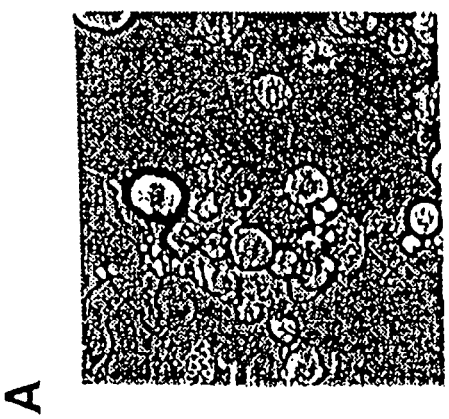
FIG. 12

```
  1 mllsvpllig llglavaepa vyfkeqfldg dgwtsrwies khksdfgkfv lssgkfygde
 61 ekdkglqtsq darfyalsas fepfsnkgqt lvvqftvkhe qmidcgggyv klfpnsldqt
121 dmhgdseyni mfgpdicgpg tkkvhvifny kgknvlinkd irckddefth lytlivrpdn
181 tyevkidnsq vesgsleddw dflppkkikd pdaskpedwd erakiddptd skpedwdkpe
241 hipdpdakkp edwdeemdge weppviqnpe ykgewkprqi dnpdykgtwi hpeidnpeys
301 pdpsiyaydn fgvlgldlwq vksgtifdnf litndeayae efgnetwgvt kaaekqmkdk
361 qdeeqrlkee eedkkrkeee eaedkededd kdedeedeed keedeeedvp gqakdel
```

METHODS AND COMPOSITIONS FOR THE TREATMENT OF DISEASES ASSOCIATED WITH SIGNAL TRANSDUCTION ABERRATIONS

This application is a continuation of U.S. Ser. No. 10/161,959 filed Jun. 3, 2002.

FIELD OF THE INVENTION

This invention generally relates to compositions and methods for counteracting and reversing disease-causing signaling defects in diseases with underlying signal transduction aberrations, including but not limited to Alzheimer's Disease.

BACKGROUND

Several signaling pathways are involved in a wide range of physiologic functions in the immune, cardiovascular, endocrine and nervous systems. Two of these pathways are the cyclic adenosine 3',5' monophosphate (cAMP)-mediated pathway and the nitric oxide (NO)-mediated pathway. These pathways interact at a number of levels.

The diseases associated with signal transduction abnormalities (either increased or decreased signaling) include (but are not limited to) Alzheimer's disease, polycystic kidney disease, prostate cancer, atopic dermatitis, rheumatoid arthritis, osteoarthritis, septic shock and congestive heart failure. Among these, Alzheimer's disease (AD) is particularly common, accounting for 50–70% of all cases of dementia. According to some estimates, the current prevalence of AD in the United States is over 4,000,000. Because the major risk factor for AD is age, its prevalence is projected to double within the next two decades due to aging of the "Baby Boomer" generation and improved life expectancy. The disease poses a major economic burden, with the national cost in 1990 estimated to be $100 billion.

At the present time, there is no cure for AD. AD management efforts are directed mostly at preventing complications, treating co-morbidities, providing symptomatic relief, as well as offering educational and emotional support to patients and families.

What is needed is a way to counteract and reverse disease-causing signaling defects in diseases with underlying signal transduction aberrations, including but not limited to Alzheimer's Disease.

SUMMARY OF THE INVENTION

In one embodiment, the present invention contemplates a method of treating a disease with an underlying signal transduction aberration (including, but not limited to those diseases listed in Tables 1 and 2) comprising: a) providing: i) a subject with one or more symptoms of a disease with an underlying signal transduction aberration, and ii) a preparation comprising an SE- or SE motif-containing peptide; and b) administering said preparation to said subject. In one embodiment, said administration to said subject is under conditions such that said one or more symptoms are reduced.

In some embodiments, said SE-containing peptides comprise (or consist of) the sequence QKRAA [Gln Lys Arg Ala Ala] [SEQ ID NO: 1]. In other embodiments, said SE-containing peptides comprise (or consist of) the sequence QRRAA [Gln Arg Arg Ala Ala] [SEQ ID NO:2]. Said SE motif-containing peptides comprise (or consist of) the sequence Q(K/R)XXA [Gln (Lys/Arg) Xaa Xaa Ala] [SEQ ID NO: 3].

In some embodiments, said SE- or SE motif-containing peptides are synthetic peptides. In some embodiments, the peptides are naturally occurring peptides or fragments thereof (e.g. fragments containing the SE sequence or SE motif). In still other embodiments, said SE- or SE motif-containing peptides are non-naturally occurring. In other embodiments, said SE- or SE motif-containing peptides range in length from five amino acids to 75 amino acids. In other embodiments, said SE- or SE motif-containing peptides range in length from five amino acids to 25 amino acids, more preferably from five amino acids to 15 amino acids. In other embodiments, said SE- or SE motif-containing peptides may be longer than 75 amino acids.

In some embodiments, said SE- or SE motif-containing peptides are conjugates, coupled to at least one moiety. In some embodiments, said SE- or SE motif-containing peptides are synthetic peptides that are conjugates, coupled to at least one moiety. In one embodiment, said conjugation is at the N-terminus of said peptides. In other embodiments, said conjugation is at the C-terminus of said peptides. In yet other embodiments, said conjugation is at both the N- and the C-terminus of said peptides. In other embodiments, said conjugated moiety is a carrier molecule. In such embodiments, said SE- or SE motif-containing peptide is conjugated to at least one carrier. Such carrier molecules facilitate targeting or delivery of the conjugate composition to a particular tissue or organ (e.g. a carrier molecule having affinity for a surface antigen of said tissue or organ). In some embodiments, said carrier molecule is selected from the group consisting of lipophilic moieties, antibodies (including antibody fragments such as Fc, Fab, single chain, and $Fab_2$) and polyamines. In some embodiments, said antibody molecule is an anti-transferrin receptor antibody. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus of said synthetic peptide, in other embodiments, said lipophilic moiety is conjugated at the C terminus of said synthetic peptide. In yet other embodiments, said lipophilic moiety is conjugated to both the N and the C terminus.

In some embodiments, said SE- or SE motif-containing peptide is selected from the group consisting of SEQ ID NOs: 1, 2, 3, 5, 6, 10, 11, 12 and 17.

In some embodiments, said SE-containing peptide is selected from the group consisting of SEQ ID NOs: 1, 2, 5, 6, 10 and 17.

In some embodiments, said SE motif-containing peptide is selected from the group consisting of SEQ ID NOs: 3, 11 and 12.

In another embodiment, the present invention contemplates a method of treating a disease with an underlying signal transduction aberration (including, but not limited to those diseases listed in Tables 1 and 2) comprising: a) providing: i) a subject with one or more symptoms of a disease with an underlying signal transduction aberration, and ii) a preparation comprising an SE-mimicking agent, such as an analogue, derivative or mimetic of an SE- or SE motif-containing peptide; and b) administering said preparation to said subject. In one embodiment, said administration to said subject is under conditions such that said one or more symptoms are reduced. In another embodiment, said analogues, derivatives or mimetics still retain biological activity.

In another embodiment, the present invention contemplates a method of treating a disease with an underlying signal transduction aberration (including, but not limited to those diseases listed in Tables 1 and 2) comprising: a) providing: i) a subject with one or more symptoms of a disease with an underlying signal transduction aberration, and ii) a preparation comprising an antagonist of an SE- or SE motif-containing peptide; and b) administering said preparation to said subject. In one embodiment, said administration to said subject is under conditions such that said one or more symptoms are reduced. In another embodiment, said antagonist retains biological activity.

In some embodiments, said SE-mimicking agents (such as analogues, derivatives or mimetics of SE- or SE motif-containing peptides) or antagonists are peptides. In other embodiments, said analogues, derivatives, mimetics or antagonists are non-peptide compounds. In cases where said analogues, derivatives, mimetics or antagonists are peptides, the length of said peptides may vary. In one embodiment, said peptides range in length from five amino acids to 75 amino acids. In other embodiments, said peptides range in length from five amino acids to 25 amino acids, and more preferably from five amino acids to fifteen amino acids.

In another embodiment, said analogues, derivatives, mimetics or antagonists are conjugates, coupled to at least one moiety. In one embodiment, said conjugation is at the N-terminus of said analogues, derivatives, mimetics or antagonists. In other embodiments, said conjugation is at the C-terminus of said analogues, derivatives, mimetics or antagonists. In yet other embodiments, said conjugation is at both the N- and the C-terminus of said analogues, derivatives, mimetics or antagonists. In other embodiments, said conjugated moiety is a carrier molecule. In such embodiments, said analogues, derivatives, mimetics or antagonists are conjugated to at least one carrier. Such carrier molecules facilitate targeting or delivery of the conjugate composition to a particular tissue or organ (e.g. by affinity for a target molecule on said organ or tissue). In some embodiments, said carrier molecule is selected from the group consisting of lipophilic moieties, antibodies (including fragments) and polyamines. In some embodiments, said antibody is an anti-transferrin receptor antibody. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the C terminus, while in other embodiments, said lipophilic moiety is conjugated at the N terminus. In other embodiments, said lipophilic moiety is conjugated to both the N and the C terminus.

In yet other embodiments, said analogues, derivatives, mimetics and antagonists are biologically active nonpeptide compounds. In such cases, conjugation (e.g. to a carrier molecule) may be direct or through a crosslinker, to an appropriate region of said nonpeptide compound (so as not to interfere with the biological activity of said nonpeptide compound).

A variety of modes of administration of the compounds of the present invention are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a joint or a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art.

In one embodiment, the present invention contemplates a method of treating Alzheimer's disease comprising: a) providing: i) a subject with one or more symptoms of Alzheimer's disease, and ii) a preparation comprising an SE-containing peptide; and b) administering said preparation to said subject. In one embodiment, said administration to said subject is under conditions such that said one or more symptoms are reduced.

In one embodiment, the present invention contemplates a method of treating Alzheimer's disease comprising: a) providing: i) a subject with one or more symptoms of Alzheimer's disease, and ii) a preparation comprising an SE motif-containing peptide; and b) administering said preparation to said subject. In one embodiment, said administration to said subject is under conditions such that said one or more symptoms are reduced.

In some embodiments, said SE-containing peptides comprise (or consist of) the sequence QKRAA [Gln Lys Arg Ala Ala] [SEQ ID NO: 1]. In other embodiments, said SE-containing peptides comprise (or consist of) the sequence QRRAA [Gln Arg Arg Ala Ala] [SEQ ID NO: 2]. Said SE motif-containing peptides comprise (or consist of) the sequence Q(K/R)XXA [Gln (Lys/Arg) Xaa Xaa Ala] [SEQ ID NO: 3].

In some embodiments, said SE- or SE motif-containing peptides are synthetic peptides. In some embodiments, said synthetic peptides are selected from the group consisting of SEQ ID NOs: 1, 2, 3, 5, 6, 10, 11, 12 and 17. In some embodiments, the peptides are naturally occurring peptides or fragments thereof (e.g. fragments containing the SE sequence or SE motif). In still other embodiments, said SE- or SE motif-containing peptides are non-naturally occurring. In other embodiments, said SE- or SE motif-containing peptides range in length from five amino acids to 75 amino acids. In other embodiments, said SE- or SE motif-containing peptides range in length from five amino acids to 25 amino acids, more preferably from five amino acids to 15 amino acids. In other embodiments, said SE- or SE motif-containing peptides may be longer than 75 amino acids.

In some embodiments, said SE- or SE motif-containing peptides are conjugates, coupled to at least one moiety. In some embodiments, said SE- or SE motif-containing peptides are synthetic peptides that are conjugates, coupled to at least one moiety. In one embodiment, said conjugation is at the N-terminus of said peptides. In other embodiments, said conjugation is at the C-terminus of said peptides. In yet other embodiments, said conjugation is at both the N- and the C-terminus of said peptides. In other embodiments, said conjugated moiety is a carrier molecule. In such embodiments, said SE- or SE motif-containing peptide is conjugated to at least one carrier. Such carrier molecules facilitate targeting or delivery of the conjugate composition to a particular tissue or organ (e.g. by affinity binding to a target molecule on tissue, such as neuronal tissue). In a preferred embodiment, said tissue or organ comprises nervous tissue in the brain. In some embodiments, said carrier molecule is selected from the group consisting of lipophilic moieties, antibodies (including fragments) and polyamines. In some embodiments, said antibody is an anti-transferrin receptor antibody. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus of said synthetic peptide, in other embodiments, said lipophilic moiety is conjugated at the C terminus of said synthetic peptide. In yet other embodiments, said lipophilic moiety is conjugated to both the N and the C terminus.

In some embodiments, said SE- or SE motif-containing peptide is selected from the group consisting of SEQ ID NOs: 1, 2, 3, 5, 6, 10, 11, 12 and 17.

In some embodiments, said SE-containing peptide is selected from the group consisting of SEQ ID NOs: 1, 2, 5, 6, 10 and 17.

In some embodiments, said SE motif-containing peptide is selected from the group consisting of SEQ ID NOs: 3, 11 and 12.

In another embodiment, the present invention contemplates a method of treating Alzheimer's disease comprising: a) providing: i) a subject with one or more symptoms of Alzheimer's disease, and ii) a preparation comprising an analogue, derivative, mimetic of an SE- or SE motif-containing peptide; and b) administering said preparation to said subject. In one embodiment, said administration to said subject is under conditions such that said one or more symptoms are reduced. In another embodiment, said analogues, derivatives, or mimetics retain biological activity.

In some embodiments, said derivative comprises a peptide containing (or consisting of) the sequence QHXXA [Gln His Xaa Xaa Ala] [SEQ ID NO: 4].

In one embodiment, said analogues, derivatives, or mimetics are conjugates, coupled to at least one moiety. In some embodiments, said analogues, derivatives or mimetics are synthetic peptides that are conjugates, coupled to at least one moiety. In one embodiment, said conjugation is at the N-terminus of said analogues, derivatives, mimetics or antagonists. In other embodiments, said conjugation is at the C-terminus of said analogues, derivatives, mimetics or antagonists. In yet other embodiments, said conjugation is at both the N- and the C-terminus of said analogues, derivatives, mimetics or antagonists. In other embodiments, said conjugated moiety is a carrier molecule. In such embodiments, said analogues, derivatives or mimetics are conjugated to at least one carrier. Such carrier molecules facilitate targeting or delivery of the conjugate composition to a particular tissue or organ. In a preferred embodiment, said tissue or organ comprises nervous tissue in the brain. In some embodiments, said carrier molecule is selected from the group consisting of lipophilic moieties, antibodies and polyamines. In some embodiments, said antibody is an anti-transferrin receptor antibody. In some embodiments, said carrier molecule is directly conjugated, while in other embodiments, said carrier molecule is conjugated via a crosslinker. In some embodiments, said lipophilic moiety is in the form of a saturated or unsaturated radical, such as hydrocarbyl or carboxylic acyl having at least five carbon atoms. In some embodiments, said lipophilic moiety is conjugated at the N terminus, in other embodiments, said lipophilic moiety is conjugated at the C terminus. In yet other embodiments, said conjugation is at both the N and the C terminus.

In yet other embodiments, said analogues, derivatives, and mimetics are biologically active nonpeptide compounds. In such cases, conjugation (e.g. to a carrier molecule) may be direct or through a crosslinker, to an appropriate region of said nonpeptide compound (so as not to interfere with the biological activity of said nonpeptide compound).

A variety of methods of administration of the compounds of the present invention for the treatment of Alzheimer's disease are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art. In the case of treatment of Alzheimer's disease, one preferred embodiment is direct application of compositions comprising compounds of the present invention directly to the brain. Such application may be accomplished, in one embodiment, by direct injection, or by implantation of a catheter and pump system for delivery into the brain. Another preferred embodiment for the treatment of Alzheimer's disease is intranasal administration, which facilitates penetration to the central nervous system through the olfactory nerve.

The dosage of the compositions used in the methods of the present invention (e.g. SE- or SE motif-containing peptides, analogues, derivatives, mimetics or antagonists) is any that is effective to reduce one or more symptoms of the subject. In some embodiments, the dosage is sufficient to attain a serum or local concentration in the range of approximately 0.5 µg/ml to approximately 500 µg/ml. In a preferred embodiment, the serum concentration is in the range of approximately 5 µg/ml to approximately 100 µg/ml, and even more preferably in the range of approximately 10 µg/ml to approximately 50 µg/ml.

In one embodiment, the present invention contemplates a method of treating rheumatoid arthritis comprising: a) providing: i) a subject with one or more symptoms of rheumatoid arthritis, and ii) a preparation comprising an antagonist of an SE- or SE motif-containing peptide; and b) administering said preparation to said subject. In one embodiment, said administration to said subject is under conditions such that said one or more symptoms are reduced.

In some embodiments, said antagonist is a conjugate, coupled to another moiety. In some embodiments, said conjugated moiety is a carrier molecule. Such carrier molecules facilitate targeting or delivery of the conjugate composition to a particular tissue or organ. In some embodiments, said carrier molecule is selected from the group consisting of lipophilic moieties, antibodies (including fragments) and polyamines. In some embodiments, said carrier molecule is directly conjugated, while in other embodiments, said carrier molecule is conjugated via a crosslinker.

In yet other embodiments, said antagonists are biologically active nonpeptide compounds. In such cases, conjugation (e.g. to a carrier molecule) may be direct or through a crosslinker, to an appropriate region of said nonpeptide compound (so as not to interfere with the biological activity of said nonpeptide compound).

A variety of methods of administration of the compounds of the present invention for the treatment of rheumatoid arthritis are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a joint or a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art. In the case of treatment of rheumatoid arthritis, one preferred embodiment is direct injection of compositions comprising compounds of the present invention directly into an affected joint. In other embodiments, such compositions suitable for intra-articular injection further comprise an anesthetic.

In other embodiments, the present invention contemplates compositions comprising SE- or SE motif-containing peptides. In some embodiments, the biological activity of such peptides can be assayed in assays of intracellular cAMP-mediated signaling. In some embodiments, said SE- or SE motif-containing peptide is selected from the group consisting of SEQ ID NOs 1, 2, 3, 5, 6, 10, 11, 12 and 17. In some embodiments, said SE-containing peptide is selected from the group consisting of SEQ ID NOs: 1, 2, 5, 6, 10 and 17. In other embodiments, said SE motif-containing peptide is selected from the group consisting of SEQ ID NOs: 3, 11 and 12. In other embodiments, said SE- or SE motif-containing peptides range in length from five amino acids to 75 amino acids. In other embodiments, said SE- or SE motif-containing peptides are between five and 25 amino acids in length, and preferably, between five and fifteen amino acids in length.

In other embodiments, the present invention contemplates biologically active derivatives and analogues of said SE- or SE motif-containing peptides. Such analogues vary from said peptides by virtue of one or more amino acid substitutions, deletions or additions. In some embodiments, said analogue or derivative is based on the sequence QHXXA [Gin His Xaa Xaa Ala] [SEQ ID NO:4]. In other embodiments, synthetic peptides that are analogues or derivatives of SEQ ID NOs: 1, 2 and 3 are contemplated. In other embodiments, the invention contemplates genetically engineered SE-containing or SE motif-containing proteins. In one embodiment, said genetically engineered protein is the hepatitis B core protein.

In some embodiments, the present invention contemplates protease-resistant peptides comprising the SE, SE motif or a derivative. In one embodiment, such protease-resistant peptides are peptides comprising protecting groups (e.g: either an N-terminal group, a C-terminal group, or both). In other embodiments, endoprotease resistance is achieved using peptides which comprise at least one D-amino acid. Such protease resistant peptides are contemplated for use in methods of treatment of a subject with symptoms of a disease with an underlying signal transduction aberration. Examples of such diseases include, but are not limited to, Alzheimer's disease.

In some embodiments, the present invention contemplates compositions comprising mimetics of SE- or SE motif-containing peptides, derivatives and analogues. Said mimetics may be peptides, or may be nonpeptide compounds. In either case, said mimetics may be conjugated to carrier molecules. In such cases, conjugation (e.g. to a carrier molecule) may be direct or through a cross linker, to an appropriate region of said nonpeptide mimetic (so as not to interfere with the biological activity of said nonpeptide mimetic). In some embodiments, said carrier molecule is a lipophilic moiety, in other embodiments, said carrier molecule is an antibody (or fragment thereof). In yet other embodiments, said carrier molecule is a polyamine.

In other embodiments, the present invention contemplates compositions comprising antagonists of SE- or SE motif-containing peptides, derivatives, analogues and mimetics. In some embodiments, said antagonist is a peptide. In other embodiments, said antagonist is a nonpeptide compound. In other embodiments, said antagonist is conjugated to another moiety. In some embodiments, the other moiety is a carrier molecule. In some embodiments, said carrier molecule is a lipophilic moiety, in other embodiments, said carrier molecule is an antibody (or fragments thereof), and in yet other embodiments, said carrier molecule is a polyamine.

In other embodiments of the present invention, pharmaceutical compositions or preparations comprising any of the compositions of the present invention (singly or in combination) are contemplated. Said pharmaceutical compositions further comprise pharmaceutically acceptable vehicles for the parenteral, oral, intranasal, intra-articular, intercerebroventricular, topical, mucosal, ocular or respiratory administration, as is well known in the art.

The present invention also contemplates the in vivo delivery of exogenous nucleic acids encoding an SE-containing or SE-motif containing peptide. While nucleic acid can be introduced to mammalian cells in vitro by a variety of physical methods, including transfection, direct microinjection, electroporation, and coprecipitation with calcium phosphate, most of these techniques are impractical for delivering genes to cells within intact animals. Therefore, a preferred approach is Receptor-Mediated DNA Delivery In Vivo.

Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu, et al., U.S. Pat. No. 5,166,320 (hereby incorporated by reference) discloses tissue-specific delivery of DNA using a conjugate of a polynucleic acid binding agent (such as polylysine, polyarginine, polyomithine, histone, avidin, or protamine) and a tissue receptor-specific protein ligand. For targeting liver cells, Wu suggests "asialoglycoprotein (galactose-terminal) ligands".

Wagner, et al., *Proc. Natl. Acad. Sci.*, 88:4255–4259 (1991) and U.S. Pat. No. 5,354,844 (hereby incorporated by reference) disclose complexing a transferrin-polylysine conjugate with DNA for delivering DNA to cells via receptor mediated endocytosis. Wagner, et al., teach that it is important that there be sufficient polycation in the mixture to ensure compaction of plasmid DNA into toroidal structures of 80–100 nm diameter, which, they speculate, facilitate the endocytic event.

The possibility of detecting gene expression by directly injecting naked DNA into animal tissues was demonstrated first by Dubenski et al., *Proc. Nat. Acad. Sci. USA*, 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, *Proc. Nat. Acad. Sci. USA*, 83:9551–55 (1986) injected calcium phosphate precipitated DNA intraperitoneally into newborn rats and noted gene expression in the livers of the animals 48 hours after transfection. In 1990, Wolff et al., *Science*, 247:1456–68 (1990), reported that the direct injection of DNA or RNA expression vectors into the muscle of mice resulted in the detectable expression of the genes for periods for up to 2 months. This technique has been extended by Acsadi et al., *New Biologist*, 3:71–81 (1991) to include direct injection of naked DNA into rat hearts; the injected genes were expressed in the heart of the animals for up to 25 days. Other genes, including the gene for dystrophin have been injected into the muscle of mice using this technique.

In one embodiment of the present invention, the DNA used is compacted to improve its survival in the cell, its uptake into the nucleus or its rate of transcription in the nucleus of the target cells. For example, the nucleic acid can be compacted at high concentrations with the carrier molecule at a critical salt concentration. The nucleic acid-loaded carrier molecule is then administered. In some embodiments, a tissue-specific carrier molecule is prepared, which is a bifunctional molecule having a nucleic acid-binding moiety and a target tissue-binding moiety.

In one embodiment, the present invention contemplates a method for delivering an oligonucleotide to cells of an animal, comprising: a) providing: i) a target binding moiety capable of binding to a polymeric immunoglobulin receptor present on the surface of a cell in a tissue of an animal; ii) a nucleic acid binding moiety; iii) an expression vector comprising an oligonucleotide encoding an SE-containing peptide or SE-motif containing peptide; iv) a subject; b) conjugating said target binding moiety to said nucleic acid binding moiety to form a carrier; c) coupling said carrier with said expression vector to form a pharmaceutical composition; and d) administering said composition to said subject. It is preferred that said expression vector (i.e., nucleic acid) is compacted.

In a preferred embodiment, the oligonucleotide is delivered to a tissue such as the brain or spinal cord. In a preferred embodiment, the expression vector further comprises a promoter sequence operably linked to the oligonucleotide. The invention is not limited by the nature of the promoter sequence chosen. In one embodiment, said target binding moiety is an antibody directed against a target molecule on neuronal tissue. It is preferred that said antibody is a monoclonal antibody or fragment thereof.

It is not intended that the present invention be limited by the nature of the nucleic acid binding moiety. In one embodiment, the nucleic acid binding moiety is a polycation, such as poly-L-lysine.

It is also not intended that the present invention be limited by the nature of the administration of the composition. In one embodiment, said administering comprises injection of said composition into said recipient animal (e.g., by intravenous injection).

In one embodiment, the present invention contemplates a method, comprising: a) providing: i) a subject having one or more symptoms of Alzheimer's disease and a plurality of neuronal cells expressing calreticulin and ii) a preparation comprising a peptide which binds said calreticulin (e.g. a calreticulin binding peptide); and b) administering said preparation to said subject under conditions such that said one or more symptoms are reduced.

In one embodiment, this peptide is an SE-containing peptide. In another embodiment, said SE-containing peptide is a synthetic peptide (which may be selected from the group consisting of SEQ ID NOs: 1, 2, 5, 6, 10, 28).

In another embodiment, these synthetic peptides are conjugates, coupled to at least one moiety, wherein said moiety is a lipophilic moiety, in the form of saturated or unsaturated radical, such as hydrocarbyl or carboxylic acyl having at least 5 carbon atoms.

In another embodiment the present invention contemplates a lipophilic moiety is conjugated at the C-terminus of said synthetic peptide.

In another embodiment the present invention contemplates a lipophilic moiety conjugated at the N-terminus of said synthetic peptide. In another embodiment, said lipophilic moiety is conjugated to both the N-terminus and the C-terminus.

In one embodiment, the present invention contemplates an SE-containing peptide conjugated to at least one carrier molecule, wherein said carrier molecule is an antibody and said antibody is an anti-transferrin receptor antibody.

The present invention also contemplates the use of non-peptide mimetics of SE-containing peptides.

BRIEF DESCRIPTION OF THE DRAWINGS

FIG. 1A is a bar graph that shows PKA activation in different cell types, with or without forskolin stimulation. (FIG. 1A abbreviations: NL, normal donors; RA, rheumatoid arthritis; HZ; homozygous tissue typing lines expressing the RA shared epitope; FSK, forskolin; PKA, protein kinase A.) FIG. 1B shows PKA activation over time in different cells. (FIG 1B. abbreviations: L565, murine L cells transfected with HLA-DRB1*0401; L259, murine L cells transfected with HLA-DRB1*0403, L300, murine L cells transfected with HLA-DRB1*0404 min, minutes.) FIG. 1C is a bar graph that shows relative PKA activation in different cells expressing different HLA DRB1 alleles. (FIG. 1C abbreviations: WT, wild type; *0404, murine L cell transfectants expressing HLA-DRB1*0404, *0403, murine L cell transfectants expressing HLA-DRB1*0403; Q70D, substitution of residue number 70 from glutamine to aspartic acid; R71K, substitution of residue number 71 from arginine to lysine; R71E, substitution, of residue number 71 from arginine to glutamic acid; A74E, substitution of residue number 74 from alanine to glutamic acid; E47A, substitution of residue number 74 from glutamic acid to alanine.)

(FIG. 2 abbreviations: 2CA, 2-chloroadenosine; $PGE_1$, prostaglandin E1, FSK, forskolin; 8-Br-cAMP, 8-bromo-cyclic AMP; H-89, a chemical inhibitor of protein kinase A; 8-Br-cGMP, 8-bromo-cyclic GMP; SNAP, S-nitroso-N-acetyl-penicillamine.) FIG. 2A is a graph which shows DNA repair in the presence of different concentrations of 2CA. FIG. 2B is a graph which shows DNA repair in the presence of different concentrations of $PGE_1$. FIG. 2C is a graph which shows DNA repair in the presence of different concentrations of forskolin. FIG. 2D is a graph which shows DNA repair in the presence of different concentrations of 8-Br-cAMP. FIG. 2E is a graph which shows DNA repair in the presence of different concentrations of enprofylline. FIG. 2F is a graph which shows DNA repair in the presence of different concentrations of H-89. FIG. 2G is a graph which shows DNA repair in the presence of different concentrations of 8-Br-cGMP. FIG. 2H is a bar graph which shows DNA repair in the presence or absence of SNAP.

FIG. 3A shows DNA repair in HEK293/A.sub.2a transfectants in the presence of different concentrations of 2CA. (FIG. 3A abbreviations: HEK293/A2a, human embryonic kidney 293 cells transfected with A2a adenosine receptor; 2CA, 2-chloroadenosine; M, Molar.) FIG. 3B shows DNA repair in HEK293/A.sub.2b transfectants in the presence of different concentrations of 2CA. (FIG. 3B abbreviations: HEK293/A2b, human embryonic kidney 293 cells transfected with A2b adenosine receptor; 2CA, 2-chloroadenosine; M, Molar.) FIG. 3C is a bar graph that shows DNA repair in HEK293/A.sub.1 transfectants in the presence of different concentrations of 2CA and cAMP. (FIG. 3C abbreviations: HEK293/A1, human embryonic kidney 293 cells transfected with A1 adenosine receptor; 2CA, 2-chloroadenosine; cAMP, cyclic AMP.)

FIG. 4A is a graph showing DNA repair over time in two transfected cell lines. (FIG. 4A abbreviations: L514, L cells transfected with HLA-DRB1*0402; L565, L cells transfected with HLA-DRB1*0401) FIG. 4B is a bar graph which shows DNA repair in different L cell transfectants. (FIG. 1B abbreviations: L565, L cells transfected with HLA-DRB1*0401; L514, L cells transfected with HLA-DRB1*0402; L259, L cells transfected with HLA-DRB1*0403.).

(FIG. 5 abbreviations: 65–79*0401, synthetic peptide corresponding to amino acids 65–79 of the β chain encoded by the HLA-DRB*0401 allele; 65–79*0402, synthetic peptide corresponding to amino acids 65–79 of the β chain encoded by the HLA-DRB*0402 allele; 65–79*0403, synthetic peptide corresponding to amino acids 65–79 of the β chain encoded by the HLA-DRB*0403 allele; 65–79*0404, synthetic peptide corresponding to amino acids 65–79 of the β chain encoded by the HLA-DRB*0404 allele.)

(FIG. 6 abbreviations: Bead*0401, peptide 65–79*0401 (corresponding to amino acids 65–79 of the β chain encoded by the HLA-DRB*0401 allele) chemically conjugated to Sepharose beads; Beads, unconjugated Sepharose beads; Bead*0402, peptide 65–79*0402 (corresponding to amino acids 65–79 of the β chain encoded by the HLA-DRB*0402 allele) chemically conjugated to Sepharose beads; ON, overnight; h, hours; min, minutes.)

FIG. 7 is an alignment which depicts SE homologies in several proteins. (FIG. 7 abbreviations: H. Laminin, human laminin; M. laminin, mouse laminin; APLP1, amyloid precursor protein-like protein 1; ApoE, apolipoprotein E.)

(FIG. 8 abbreviations: H. Laminin, human laminin; M. laminin, mouse laminin; H. Fibronectin, human fibronectin.)

FIG. 10A shows cAMP levels in the presence of different concentrations of 2CA and after preincubation with different peptide-conjugated beads. (FIG. 10A abbreviations: 2CA, 2-chloroadenosine; Bead*0401, peptide 65–79*0401 (corresponding to amino acids 65–79 of the β chain encoded by the HLA-DRB*0401 allele) chemically conjugated to Sepharose beads: Bead*0402, peptide 65–79*0402 (corresponding to amino acids 65–79 of the β chain encoded by the HLA-DRB*0402 allele) chemically conjugated to Sepharose beads; min, minutes; cAMP, cyclic AMP.) FIG. 10B shows PKA activity following preincubation with different peptide-conjugated beads. (FIG. 10B abbreviations: Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; PKA, protein kinase A; min, minutes.) FIG. 10C shows NO levels following preincubation with different peptide-conjugated beads. (FIG. 10C. abbreviations: NO, nitric oxide; Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; min, minutes.) FIG. 10D shows cGMP levels following exposure to different soluble peptides. (FIG. 10D abbreviations: *0401, soluble peptide 65–79*0401 (corresponding to amino acids 65–79 of the β chain encoded by the HLA-DRB*0401 allele) *0402, soluble peptide 65–79*0402 (corresponding to amino acids 65–79 of the β chain encoded by the HLA-DRB*0402 allele); cGMP, cyclic GMP; min, minutes.) FIG. 10E is a bar graph that shows DNA repair in cells exposed or not to L-NMA and different peptide-conjugated beads. (FIG. 10E abbreviations: Bead*0401, peptide 65–79*0401 (corresponding to amino acids 65–79 of the β chain encoded by the HLA-DRB*0401 allele) chemically conjugated to Sepharose beads; Bead*0402, peptide 65–79*0402 (corresponding to amino acids 65–79 of the β chain encoded by the HLA-DRB*0402 allele) chemically conjugated to Sepharose beads; L-NMA, $N^G$-monomethyl-L-arginine.) FIG. 10F is a bar graph that shows DNA repair in cells preincubated or not with KT5823 and preincubated with different peptide-conjugated beads. (FIG. 10F abbreviations: Bead*0401, peptide 65–79*0401 (corresponding to amino acids 65–79 of the β chain encoded by the HLA-DRB*0401 allele) chemically conjugated to Sepharose beads; KT5823, a chemical inhibitor of protein kinase G.)

Figure 1:
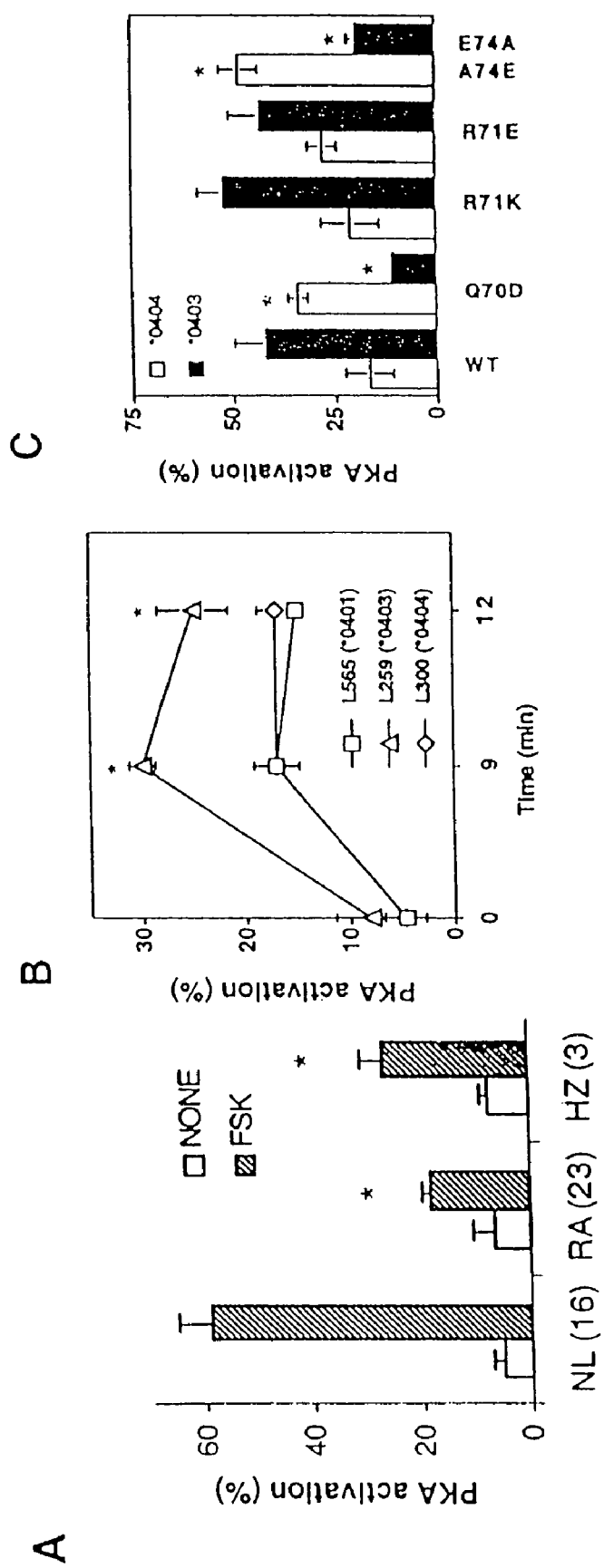
FIG. 1 depicts the impaired cAMP signaling exhibited in SE-expressing cells.

As used herein "protease resistant peptides" refers to peptides with a reduced susceptibility to protease digestion. For example, a protease resistant peptide may comprise a protecting group, or may comprise at least one D-amino acid. It is not intended that the present invention be limited to complete protease resistance. It is enough if susceptibility to protease digestion is reduced.

As used herein, "antagonists" of SE or SE motif-containing peptides refers to molecules or compounds which are inhibitory to SE or SE motif-containing peptides. Antagonists may or may not be homologous to the native compound which they inhibit with respect to conformation, charge or other characteristics. Thus, antagonists may be recognized by the same or different receptors that are recognized by the natural compound. SE- or SE motif-containing peptide antagonists are contemplated to be useful in the treatment of diseases which have signal transduction aberrations comprising reduced cAMP-mediated signaling or over-active NO-mediated signaling (see Tables 1 and 2). Rheumatoid arthritis is one example of such a disease.

As used herein, "conjugates" of SE or SE motif-containing peptides, peptide derivatives, analogues or antagonists refers to such peptides with a moiety linked to said peptide. In some embodiments, said linkage is to the N- or C-terminus, or both, of the peptide. In some embodiments, conjugation is achieved through the introduction of a cysteine into the peptide. While the cysteine can be added at the N or C termini, it can also be introduced into the middle of the motif. In some embodiments, the conjugate comprises linkage of a lipophilic or hydrophobic moiety. In some embodiments, the conjugate comprises linkage of a carrier molecule, including but not limited to an antibody. The linkage between the peptide and the moiety can be a direct chemical linkage, or the linkage can be through a linking agent, such as a cross-linker.

As used herein, "signal transduction aberrations" include (but are not limited to) over-activity or reduced activity of the cAMP-mediated and NO-mediated intracellular signaling pathways. Signal transduction aberrations also include disruptions in the balance between signaling pathways, such as the cAMP- and NO-mediated pathways. Signal transduction aberrations can also include alterations to intercellular signaling pathways.

As used herein, "diseases with underlying signal transduction aberrations" include, but are not limited to those diseases listed in Tables 1 and Tables 2. In such diseases, intercellular and intracellular signal transduction aberrations may underlie the pathogenesis of the disease.

As used herein, "synthetic peptide" refers to a peptide made by chemical or enzymatic synthetic procedures well known in the art. Synthetic SE- and SE motif-containing peptides, derivatives, analogues and mimetics are contemplated.

As used herein, "protecting groups" are those groups which prevent undesirable reactions (such as proteolysis) involving unprotected functional groups. Protecting groups can be added to the N-terminus, C-terminus or both of an SE-containing or SE motif-containing peptide. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

As used herein, "biological activity" of SE- or SE motif-containing peptides, derivatives or analogues and mimetics refers to the ability of said peptides, derivatives or analogues and mimetics to modulate signal transduction pathways. Such activity can be assayed by a number of means. For example, biological activity can be assayed in an in vitro cAMP-mediated assay for DNA repair following induction of DNA damage. SE-containing peptides inhibit DNA repair in such an assay. Biological activity of such peptides can also be determined by measuring intracellular cAMP levels or protein kinase A activation following application of said peptides to cells.

As used herein, the "N-terminus" of a peptide refers to the end of the peptide with a free amino group. Note that the N-terminus amino group does not necessarily have to be "free", for example, it may be involved in linking of moieties to the N-terminus in conjugates.

As used herein, the "C-terminus" of a peptide refers to the end with a free carboxyl group. Note that the C-terminus carboxyl group does not necessarily have to be "free", for example, it may be involved in linking moieties to the C-terminus in conjugates.

As used herein, a "carrier molecule" refers to a moiety used to facilitate transport of compounds of the invention (for example, SE-containing peptides) to neuronal tissue or across the blood brain barrier. The carrier molecule can be directly linked to the compounds of the invention, linked by a cross-linker or physically associated with the compounds of the invention. Carrier molecules include, but are not limited to, lipophilic or hydrophobic moieties, antibodies (and fragments thereof) or other molecules (such as polyamines, including but not limited to spermine).

As used herein, an "antibody" is a molecule produced by specific cells of the immune system. An antibody specifically recognizes and binds to another compound. In one embodiment of the present invention, an antibody that recognizes and binds to the transferrin receptor is contemplated for use as a carrier molecule for SE-containing peptides. The present invention contemplates the use of both polyclonal and monoclonal antibodies (and fragments thereof).

As used herein, "subject" refers to a human or animal.

As used herein, "HLA-DR4", or "DR4" refers to a particular human leukocyte antigen (or major histocompatibility complex antigen), as determined serologically. The DR4 antigen is associated with the DR locus B1 $\beta$ chain ("DRB1"). Multiple alleles of DRB1 are associated with the DR4 antigen. For example, DRB1*0401 and DRB1*0402 refer to the alleles, while the corresponding $\beta$ chains are referred to as DR$\beta$*0401 and DR$\beta$*0402, respectively.

As used herein, "single dosage" refers to a pharmaceutical composition of a formulation that is capable of achieving its intended effect in a single application or administration (e.g. once a day).

As used herein, "oral administration" or "orally" refers to the introduction of a pharmaceutical composition into a subject by way of the oral cavity (e.g., in aqueous liquid or solid form).

As used herein, "sublingual administration" or "sublingually" refers to the introduction of a pharmaceutical composition into a subject by application to the mucosal surface under the tongue (within the oral cavity) such that the composition is absorbed into the subject.

As used herein, "buccal administration" or "buccal" refers to the introduction of a pharmaceutical composition into a subject by application to the mucosal surface lining the cheek (within the oral cavity) such that the composition is absorbed into the subject.

As used herein, "intranasal administration" or "intranasally" refers to the introduction of a pharmaceutical composition within the nasal cavity.

As used herein, "respiratory inhalation" refers to the introduction of a pharmaceutical composition within the respiratory tract.

As used herein, "intrapulmonary delivery" refers comprises administration to the lung. Intrapulmonary delivery of pharmacologic agents to patients can be accomplished via aerosolization. Alternatively, the agent may be administered to the lung through a bronchoscope.

As used herein, "transdermal administration" or "transdermally" or "cutaneously" refers to the introduction of a pharmaceutical composition into a subject by application to the surface of the skin such that the composition is absorbed into the subject.

As used herein, "injection" or "standard injection" refers to the placement of a pharmaceutical composition into a subject (e.g., with a hypodermic needle). For example, such injection can be made subcutaneously, intravenously, intramuscularly, intracavernosally, etc.

As used herein, "intra-articular" injection refers to direct injection of a pharmaceutical composition into a joint (for example, in a method of treatment of rheumatoid arthritis).

DESCRIPTION OF THE INVENTION

A. Signaling Pathways

Over the past decade it has become increasingly apparent that intercellular and intracellular signal transduction aberrations may underlie the pathogenesis of many diseases. Consequently, attempts to target such signaling abnormalities have become a common theme in the design of new therapeutic strategies [Reviewed in Levitzki A. *Curr Opin Cell Biol* 8:239–244 (1996)]). The methods and compositions of the present invention allow for modulation of the balance between two antagonistic signaling pathways, mediated, respectively, by cyclic adenosine 3',5' monophosphate (cAMP) and nitric oxide (NO).

The cAMP-mediated pathway [reviewed in Antoni F A. *Front Neuroendocrinol* 21:103–132 (2000)] is involved in a myriad of important physiologic functions in the immune, cardiovascular, endocrine and nervous systems, to mention only a few. Diminished or excessive activation of this pathway may result in various pathologies, as exemplified by the list of disorders shown in Table 1. For instance, over-activity of the cAMP-PKA pathway has been implicated in the pathogenesis of polycystic kidney disease, idiopathic nephrotic syndrome, HIV-induced T cell anergy, non-autoimmune hyperthyroidism, prostate cancer, pre-malignant breast pathology, dopamine-induced motor disorder, obesity, arrhythmia and Alzheimer's disease (AD, see below). Conversely, blunted cAMP responses have been observed in a number of inflammatory or autoimmune conditions, such as systemic lupus erythematosus, psoriasis, asthma, glomerulonephritis, atopic dermatitis and rheumatoid arthritis (RA, see below).

NO is a ubiquitous second messenger with a wide range of effects in many tissues, in particular, the cardiovascular, endothelial, immune and the central nervous systems. Many pathological states have been attributed to aberrations in the NO system (Table 2). For example, elevated NO levels are found in inflammatory and autoimmune diseases, such as inflammatory bowel disease, infectious diseases and various experimental models of autoimmunity. Elevated NO levels have been also implicated in the pathogenesis of osteoarthritis, septic shock, and uremia. On the other hand, inadequate levels of NO have been implicated in the pathogenesis of atherosclerosis, AD (see below), pulmonary hypertension, re-stenosis, insulin resistance syndrome, ischemia-reperfusion injury, congestive heart failure, non-steroidal (NSAID)-associated gastrointestinal (GI) toxicity and, possibly, acute respiratory distress syndrome.

It is noteworthy that the NO and cAMP signaling pathways interact at different levels. For example, cAMP can either inhibit or stimulate inducible NO synthase (NOS2), depending on the cell type. While in hepatocytes, astrocytes and glial cells, cAMP-elevating agents almost invariably suppress NOS2 expression, the opposite outcome has been observed in aortic smooth muscle cells, cardiac myocytes, mesangial cells adipocytes and endothelial cells [Galena E and Feinstein D L. *FASEB J* 13:2125–2137 (1999)]. Conversely, NO can inhibit cAMP signaling either by suppressing adenylate cyclase, or by activation of soluble guanylate cyclase [Denninger J W and Marletta M A. *Biochim Biophys Acta* 1411:334–350 (1999)], with resultant increase in cyclic guanosine monophosphate (cGMP) levels, which in turn can facilitate cAMP degradation by activating phosphodiesterases.

TABLE 1

Examples of Disease-Associated Signal Transduction Abnormalities in the cAMP-PKA Pathway

| SIGNALING ABERRATION | DISEASE |
| --- | --- |
| Over Activity: | Alzheimer's disease |
| | arrhythmia |
| | dopamine-induced motor disorder |
| | HIV-induced T cell anergy |
| | idiopathic nephrotic syndrome |
| | non-autoimmune hyperthyroidism |
| | obesity |
| | polycystic kidney disease |
| | pre-malignant breast pathology |
| | prostate cancer |
| Reduced Activity: | asthma |
| | atopic dermatitis |
| | glomerulonephritis |
| | psoriasis |
| | rheumatoid arthritis |
| | systemic lupus erythematosus |

TABLE 2

Examples of Disease-Associated Signal Transduction Abnormalities in the NO-cGMP Pathway

| SIGNALING ABERRATION | DISEASE |
| --- | --- |
| Over Activity: | experimental models of autoimmunity |
| | infectious diseases |
| | inflammatory bowel disease |
| | osteoarthritis |
| | septic shock |
| | uremia |

TABLE 2-continued

Examples of Disease-Associated Signal Transduction Abnormalities in the NO-cGMP Pathway

| SIGNALING ABERRATION | DISEASE |
|---|---|
| Reduced Activity: | acute respiratory distress syndrome |
| | Alzheimer's Disease |
| | atherosclerosis |
| | congestive heart failure |
| | insulin resistance syndrome |
| | ischemia-reperfusion injury |
| | NSAID GI toxicity |
| | pulmonary hypertension |
| | re-stenosis |

B. Subjects to be Treated

The utility of the present invention relates to many disease states caused by signaling aberrations, as exemplified in Tables 1 and 2. For the purposes of illustration, and not to be construed as limiting, the potential utility of the invention will be discussed in the context of Alzheimer's disease (AD) and rheumatoid arthritis (RA).

1. Alzheimer's Disease

AD is a common neurodegenerative disease, accounting for 50–70% of all cases of dementia. Clinically, the disease is characterized by insidious loss of memory and other cognitive functions, as well as affective, behavioral and psychiatric abnormalities, which gradually evolve into dementia. According to some estimates, the current prevalence of AD in the United States is over 4,000,000. Because the major risk factor for AD is age, its prevalence is projected to double within the next two decades due to aging of the 'Baby Boomer' generation and improved life expectancy.

The disease poses a major economic burden. The total annual cost per case in the US was estimated as $47,000 in 1990 [Rice D P et al. Health Aff 12:165–176 (1993), which translated into a national cost of $100 billion, or ~2% of the GDP in that year. These staggering statistics and the projected aging of the US population, make AD an enormous public health problem. Finding a cure for AD, or identifying measures to even modestly delay its onset would have a major public health impact.

The main obstacle for designing effective treatments for AD is the fact that the pathogenesis of the disease is not well understood. Histologically, brain tissue of AD patients shows extracellular senile plaques consisted mostly of β-amyloid (Aβ) that is derived from APP (amyloid precursor protein), and intracellular neurofibrillary tangles containing pathologically hyperphosphorylated tau protein. The mechanisms leading to those changes are not well understood.

The etiology of AD has a strong genetic basis. Mutations in the APP or presenilin 1 (PS1) and PS2 genes, have been shown to underlie the early onset familial AD, whereas the risk for late-onset AD correlates with particular alleles of apolipoprotein (Apo) E [St. George-Hyslop P H. Biol Psychiatry 47:183–199 (2000)]. Interestingly, AD has long been noticed to be conspicuously rare among patients with RA [McGeer et al. Lancet 335:1037 (1990); Jenkinson et al. Br J Rheumatol 28:86–88 (1989); McGeer et al. Neurology 47:425–432 (1996)].

APP is a member of a family of transmembrane glycoproteins, which also include amyloid purcorsor-like protein-1 (APLP1) and APLP2. The physiologic function of these proteins is believed to involve cell-cell and cell-extracellular matrix interactions. In the familial forms of AD, due to mutations in either the APP gene or in PSN1 or PSN2, which affect APP processing, there is an increased cleavage of APP at the beta and gamma cleavage sites with resultant accelerated accumulation of Aβ.

Unlike the ubiquitously expressed APP and APLP2, APLP1 is expressed exclusively in the central nervous system, primarily in cerebral cortex postsynaptic densities [Kim T W et al. Brain Res Mol Brain Res 32:36–44 (1995)]. In addition to the putative functions of adhesion, neurite development and neuroprotection, shared by all members of the APP gene family, APLP1 may play a unique role in neurogenesis [Lorent K et al. Neuroscience 65:1009–1025 (1995)].

Genetic linkage studies indicate a susceptibility locus for AD on chromosome 19q12–q13 [Pericak-Vance M A et al. Am J Hum Genet 48:1034–1050 (1991)], a region which contains the APOE gene. The three major human ApoE alleles differ in two codons. The most common allele, ApoE3, is present in 75% of Caucasians and encodes a cysteine at position 112 and arginine at position 158. Allele ApoE2 (10% of Caucasians) encodes two cysteines, while ApoE4 (15% of Caucasians) has two arginines in those two positions. Analysis of the frequency of ApoE alleles in AD patients and controls show that there is increased frequency (40%) of the ApoE4 allele [Saunders A M et al. Neurology 43:1467–1472 (1993)] and decreased frequency (2%) of the ApoE2 allele [Corder E H et al. Nat Genet 7:180–184 (1994)] in patients with AD. Moreover, there is an inverse relationship between the number of ApoE4 copies and the age of onset of AD, with ApoE4/ApoE4 homozygous subjects showing the earliest age of onset [Corder E H et al. Science 261:921–923 (1993)].

Although the mechanism by which different ApoE alleles affect AD disease susceptibility is unclear, (and an understanding of this mechanism is not necessary to the successful practice of the invention) there is a substantial body of evidence to suggest that the ApoE polymorphism might directly influence the intracellular fate of tau and the processing of Aβ peptides [reviewed in Stirttmatter W J and Roses A D. Proc Natl Acad Sci USA 92:4725–4727 (1995); St. George-Hyslop P H. Biol Psychiatry 47:183–199 (2000)]. Studies with ApoE-deficient mice reveal memory deficits and hyperphosphorylation of tau. Taken together, human studies and ApoE knock out mice data support the hypothesis that ApoE may have a protective role, which allele ApoE4 may be uniquely devoid of.

Laminin has been shown to play a role in neuronal physiology [reviewed in Luckenbill-Edds L. Brain Res Rev 23:1–27 (1997)] and to modulate the neurodegenerative process in AD. For example, in vitro studies have shown that laminin inhibits formation of Aβ40 [Monji A et al. Neurosci Lett 251:65–68 (1998)] and Aβ42 [Monji A et al. Brain Res 788:187–190 (1998)] fibrils and attenuates amyloid peptide neurotoxicity in rat cortical neurons [Drouet B et al. J Neurochem 73:742–749 (1999)]. Interestingly, interaction of laminin with ApoE has been shown to enhance laminin's effect [Huang D Y et al. Exp Neurol 136:251–257 (1995)] and ApoE4-induced Aβ fibril formation can be reversed by laminin [Monji A et al. Brain Res 796:171–175 (1998)]. Thus, it is conceivable that laminin and ApoE encoded by either the ApoE2 or ApoE3 alleles operate synergistically, while the ApoE4 allele product has an opposite effect (but again, the invention is in no manner limited to such a mechanism). It is noteworthy that ApoE and laminin have been shown to co-localize anatomically in vivo.

AD begins slowly. At first, the only symptoms may be mild forgetfulness. People with AD may have trouble remembering recent events, activities, or the names of familiar people or things. Simple math problems may become hard for these people to solve. As the disease progresses, symptoms are more easily noticed and become serious enough to cause people with AD or their family members to seek medical help. For example, people with AD may forget how to do simple tasks, like brushing their teeth or combing their hair. They can no longer think clearly; and they begin to have problems speaking, understanding, reading, or writing. Later on, people with AD may become anxious or aggressive, or wander away from home. Eventually, patients may need total care. In general, the disease may be thought of in terms of three stages: mild, moderate and severe. Although the divisions are approximate and overlap, and progression of symptoms vary from one individual to the next, the symptoms and stages are still helpful in defining the disease state. Mild symptoms include confusion and memory loss, disorientation (getting lost in familiar surroundings), problems with routine tasks and changes in personality and judgement. Moderate symptoms include difficulty with activities of daily living (such as feeding and bathing), anxiety, suspiciousness, agitation, sleep disturbances, wandering, pacing and difficulty recognizing family and friends. Severe symptoms include loss of speech, loss of appetite and weight, loss of bladder and bowel control and total dependence on the caregiver.

Doctors at specialized centers can diagnose AD correctly 80 to 90 percent of the time. The presence of characteristic plaques and tangles in the brain can only be determined by looking at a piece of brain tissue under a microscope. It can be painful and risky to remove brain tissue while a person is alive, so doctors cannot look at the tissue until a post-mortem autopsy. Instead, doctors may say that a person has "probable" AD by finding out more about the patient's symptoms. For example, neuropsychological tests of memory, problem solving, attention, counting and language are carried out to pinpoint the specific problems the person has. The doctor may also carry out brain scans, such as computerized tomography, magnetic resonance imaging scans or positron emission tomography scans. These scans help the doctor rule out other causes of the person's symptoms, such as brain tumors or blood vessel disease.

Unfortunately, there is no specific treatment for AD. Cholinesterase inhibitors have been shown to have some effect in mild to moderate AD. Other treatments include free radical inhibitors, estrogen and anti-inflammatory drugs. None of these treatments has been found to effectively arrest disease progression. Consequently, AD management efforts are directed mostly at preventing complications, treating co-morbidities providing symptomatic relief, as well as offering educational and emotional support to patients and families.

2. Rheumatoid Arthritis

RA is the most common form of inflammatory arthritis, causing chronic inflammation of the joints, crippling deformities and early death [reviewed in Harris E D. *N Engl J Med* 322:1277–1289 (1990)]. The genetic predisposition to RA is strongly associated with the HLA-DRB1 locus of the major histocompatibility complex [Nepom G T et al. *Arthritis Rheum* 32:15–21 (1989)]. The vast majority of RA patients express HLA-DRB1 alleles encoding a "shared epitope" (SE), which contain the amino acid motif of QKRAA [Gln Lys Arg Ala Ala] [SEQ ID NO: 1] or QRRAA [Gln Arg Arg Ala Ala] [SEQ ID NO: 2] in residues 70–74 of the DRβ chain [Greegersen P K et al. *Arthritis Rheum* 30:1205–1213 (1987)]. The mechanism by which the SE affects disease susceptibility is unknown. Several mechanisms have been put forward as explanations, including presentation of arthritogenic self-peptides, molecular mimicry with foreign antigens, T cell repertoire selection or linkage disequilibrium with other genes. While those mutually non-exclusive hypotheses are all plausible, none of them provide an explanation for the seemingly random occurrence of RA among genetically susceptible individuals, as illustrated in monozygotic (MZ) twins. Recent studies estimate the concordance rate of RA in MZ twins at 12–15% only. It has been therefore suggested that in addition to the strong influence of genetic factors, stochastic events, such as somatic mutations, might be involved. Indeed, higher mutation rates, increased sensitivity to genotoxic agents and reduced DNA repair capacity have all been previously detected in RA.

It is noteworthy that association with the same DRB1 alleles has been shown in autoimmune diseases other than RA, such as polymyalgia rheumatica, giant cell arteritis, IDDM autoimmune hepatitis, as well as with a non-immune condition, early-onset chronic lymphoid leukemia. Thus, the association with a wide spectrum of antigenically and pathogenetically diverse diseases suggests that the RA SE may exert antigen-nonspecific influence [Auger I et al. *Nature Med* 2:306–310 (1996)].

In addition to its well-documented role in disease susceptibility, there is evidence to suggest that the RA SE may contribute to disease severity as well [Weyand C M et al. *Ann Intern Med* 117:10 801–806 (1992); Gonzalez-Escribano M F et al. *Hum Immunol* 60:1259–1265 (1999); Valenzuela A et al. *Hum Immunol* 60:250–254 (1999); Salvarani C et al. *Br J Rheumatol* 37:165–169 (1998)]. Genetic analyses indicate that the SE 'dose' has a measurable effect on disease outcome in many populations studied. Patients with a single SE-expressing allele tend to have a milder disease, less destructive joint changes and infrequent extra articular involvement, as compared to patients with two such alleles. Thus, the SE may have a dual role in RA: determination of disease susceptibility on the one hand and affecting disease severity on the other. The experimental results reported below indicate that the SE has a direct impact on intracellular signaling events.

Rheumatoid arthritis is an inflammatory disease of the synovium, or lining of the joint, that results in pain, stiffness, swelling, deformity, and loss of function in the joints. Inflammation most often affects joints of the hands and feet and tends to be symmetrical (occurring equally on both sides of the body). This symmetry helps distinguish rheumatoid arthritis from other types of arthritis. Pain and stiffness occur and last for more than 30 minutes in the morning or after a long rest.

Diagnosis of rheumatoid arthritis is often carried out by a rheumatologist. The doctor will review the patient's medical history, conduct a physical examination, and obtain laboratory tests and X-rays or other imaging tests. The doctor will examine all of the patient's joints for redness, warmth, deformity, ease of movement, and tenderness. Some of the laboratory tests may include arthrocentesis (joint aspiration to obtain a sample of synovial fluid), a blood test to detect rheumatoid factor (an antibody found in the blood of most (but not all) people who have rheumatoid arthritis) or an erythrocyte sedimentation rate test (which can be indicative of inflammation present in the body). Early diagnosis is important, as destruction of cartilage and bone within the joint may begin as early as the first year or two that a person has the disease.

Treatment goals in RA are to relieve pain, reduce inflammation, slow down or stop joint damage and improve the person's sense of well being and ability to function. Treatments for RA include rest and relaxation, exercise, proper diet and medication. Other treatments include the use of pain relief methods and assistive devices, such as splints or braces. In severe cases, surgery may be necessary. Medications include non-steroidal antiflammatories and other analgesics to reduce the pain and inflammation associated with RA. Other medications include gold, penicillamine, antimalarials (such as hydroxychloroquine), sulfasazine, methotrexate, azathioprine, cyclophosphamide and corticosteroids (such as prednisone and methylprednisolone).

3. Negative Association Between AD and RA

AD is conspicuously rare in RA patients. Both case-control and population-based studies have revealed a strong negative association between the two diseases [McGeer et al. *Lancet* 335:1037 (1990); Jenkinson et al. *Br J Rheumatol* 28:86–88 (1989); McGeer et al. *Neurology* 47:425–432 (1996)]. Statistical meta-analysis of the literature estimated the odd ratio for AD in RA as 0.194 (p<0.0001). The negative association between the two diseases has been previously attributed to extensive use of presumably AD-protective NSAID by RA patients. However, more recent evidence indicates that the negative association of AD with RA could be directly attributed to the RA-associated HLA-DRB1, rather than to drug use history, since DR4 itself has been found to associate with decreased risk for AD [Curran M et al. *NeuroReport* 8:1467–1469 (1997)]. Quantification of glial fibrillary acidic protein in hippocampal tissues from AD patients suggest that HLA-DR4 may exert a protective influence on AD [Aisen P S et al. *J Neurol Sci* 161:66–69 (1998)].

C. Compositions

While not wishing to be limited to any particular mechanism, it is believed that SE- and SE motif-containing peptides, derivatives, analogues, mimetics and antagonists can be used to counteract or reverse signal transduction aberrations underlying a number of diseases, including AD and RA. As demonstrated in the Experimental section below, SE- and SE motif-containing peptides inhibit cAMP-mediated DNA repair induction in cultured cells, as do genetically engineered SE-containing proteins. Additionally, SE-containing peptides confer neuroprotective effects in cultured cells.

As noted above, the vast majority of RA patients express HLA-DRB1 alleles encoding a "shared epitope" (SE), which contain the amino acid motif of QKRAA [Gln Lys Arg Ala Ala] [SEQ ID NO: 1] or QRRAA [Gln Arg Arg Ala Ala] [SEQ ID NO: 2] in residues 70–74 of the DRβ chain [Greegersen P K et al. *Arthritis Rheum* 30:1205–1213 (1987)].

As illustrated in the examples below, the cAMP-inhibiting domain of RA-associated SE maps to the third allelic hypervariable region of the DRβ protein. Inhibition of cAMP signaling was obtained by incubating cells with particular synthetic peptides, corresponding to amino acids 65–79 or 65–78 of particular alleles of the third allelic hypervariable domain of DRβ. Inhibition was associated with the peptides corresponding to the third allelic hypervariable region of the RA-SE-expressing DRB1 alleles *0401 and *0404, but not with peptides corresponding to that region in the control alleles *0402 or *0403. The sequences of the third allelic hypervariable region peptides used are shown in Table 3 below.

TABLE 3

Third Allelic Hypervariable Region Peptides Used in the Study. (Synthetic Peptides)

| Peptide | Amino Acid Sequence | SEQ ID NO. |
|---|---|---|
| 65-79*0401 | KDLLEQKRAAVDTYC<br>Lys Asp Leu Leu Glu<br>Gln Lys Arg Ala Ala<br>Val Asp Thr Tyr Cys | [SEQ ID NO: 5] |
| 65-78*0401 | KDLLEQKRAAVDTY<br>Lys Asp Leu Leu Glu<br>Gln Lys Arg Ala Ala<br>Val Asp Thr Tyr | [SEQ ID NO: 6] |
| 65-79*0402 | KDILEDERAAVDTYC<br>Lys Asp Ile Leu Glu<br>Asp Glu Arg Ala Ala<br>Val Asp Thr Tyr Cys | [SEQ ID NO: 7] |
| 65-78*0402 | KDILEDERAAVDTY<br>Lys Asp Ile Leu Glu<br>Asp Glu Arg Ala Ala<br>Val Asp Thr Tyr | [SEQ ID NO: 8] |
| 65-79*0403 | KDLLEQRRAEVDTYC<br>Lys Asp Leu Leu Glu<br>Gln Arg Arg Ala Glu<br>Val Asp Thr Tyr Cys | [SEQ ID NO: 9] |
| 65-79*0404 | KDLLEQRRAAVDTYC<br>Lys Asp Leu Leu Glu<br>Gln Arg Arg Ala Ala<br>Val Asp Thr Tyr Cys | [SEQ ID NO: 10] |
| 65-78*0404 | KDLLEQRRAAVDTY<br>Lys Asp Leu Leu Glu<br>Gln Arg Arg Ala Ala<br>Val Asp Thr Tyr | [SEQ ID NO: 28] |

Further investigation identified the QRRAA [Gln Arg Arg Ala Ala] [SEQ ID NO: 2] SE sequence in three human nervous system proteins: APLP1, laminin β2 and ankyrin B. A homologous sequence was also found around the variable position 158 of ApoE. Use of pentapeptides based on these sequences (see example below) showed that the cAMP signal-inhibiting sequences possess the Q-(K/R)-X-X-A [Gln (Lys/Arg) Xaa Xaa Ala (wherein Xaa represents any amino acid)] [SEQ ID NO: 3] motif. This motif exists in RA SE, as well as in APLP1, laminin β2 and ApoE. Thus, the motif from the SE which appears to be associated with signal transduction (i.e. the SE motif) is Q-(K/R)-X-X-A [Gln (Lys/Arg) Xaa Xaa Ala (wherein Xaa represents any amino acid)] [SEQ ID NO: 3].

The length of SE- or SE motif-containing peptides can vary. In some embodiments, SE- or SE motif-containing peptides range in length from five to hundreds of amino acids. In other embodiments, SE- or SE motif-containing peptides are between five amino acids and 75 amino acids in length. In other embodiments, SE- or SE motif-containing peptides are between five amino acids and 25 amino acids in length, and in yet other embodiments, SE- or SE motif-containing peptides are between five amino acids and fifteen amino acids in length.

In some embodiments, said SE- or SE motif-containing peptides comprise genetically engineered proteins. For example, said SE- or SE motif-containing sequences may be inserted into the sequence of another protein, including, but not limited to, the hepatitis B core (HBc) protein. In one embodiment, residues 65–79 of the SE-containing DRβ*0401 chain are engineered to be expressed at the tips of the HBc spikes. Recombinant viral particles thus comprise an SE-containing peptide on the spikes of the viral shell. In other embodiments, SE motif-containing peptides similarly expressed in an engineered HBc protein are contemplated.

As noted above, sequences which vary from the QRRAA [Gln Arg Arg Ala Ala] [SEQ ID NO: 2] and the QKRAA [Gln Lys Arg Ala Ala] [SEQ ID NO: 1] SE still retain biological activity, as assayed in a cAMP signaling assay (to measure induction of DNA repair; see experimental section below). For example, QKRLA [Gln Lys Arg Leu Ala] [SEQ ID NO: 11] and QKCLA [Gln Lys Cys Leu Ala] [SEQ ID NO: 12] pentapeptides inhibited cAMP signaling. Both of these pentapeptides conform to the Q(K/R)XXA [Gln (Lys/Arg) Xaa Xaa Ala (wherein Xaa represents any amino acid)] [SEQ ID NO: 3] motif. Other peptides containing variations of the Q(K/R)XXA [Gln (Lys/Arg) Xaa Xaa Ala (wherein Xaa represents any amino acid)] [SEQ ID NO: 3] motif are also expected to have cAMP signal inhibition activity. Any such peptides are contemplated for use in the present invention. Such SE motif-containing peptides may have a range of lengths, from approximately five amino acids to peptides containing up to several hundred amino acids. Most preferably, SE motif-containing peptides will range from approximately 5 amino acids to approximately 20 amino acids in length, even more preferably from approximately 5 to approximately 15 amino acids in length.

It is also believed that other alterations can be made to SE-containing or SE motif-containing peptides to produce variant peptides (i.e. derivatives and analogues) that retain biological activity. An alteration is defined as a substitution, deletion or insertion of one or more amino acids in the peptides of interest. For example, peptides comprising the sequence QHXXA [Gln His Xaa Xaa Ala (wherein Xaa represents any amino acid)] [SEQ ID NO: 4] are expected to have cAMP signal inhibition activity. Preferably, the alterations are conservative amino acid changes.

For example, it is contemplated that an isolated replacement of a leucine with an isoleucine or valine, an alanine with a glycine, a threonine with a serine or a similar replacement of an amino acid with a structurally related amino acid (i.e. conservative substitutions) will not have a major effect on the biological activity of the resulting molecule. Conservative substitutions are those that take place within a family of amino acids that are related by their side chains. Amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In an alternative, yet similar fashion, the amino acid repertoire can be grouped as: (1) acidic (aspartate, glutamate); (2) basic (lysine, arginine, histidine); (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (See e.g. Stryer ed., Biochemistry, 2E, WH Freeman and Co. (1981) pp. 13–16).

Thus, in certain embodiments, modifications of the SE- or SE motif-containing peptides selected from the group consisting of SEQ ID NOs: 1, 2, 3, 5, 6, 10, 11, 12 and 17 are contemplated by the present invention. Guidance in determining which and how many amino acid residues may be substituted, inserted, or deleted without abolishing biological activity may be found by using computer programs well known in the art, for example, DNAStar software or GCG (Univ. of Wisconsin).

Whether a change in the amino acid sequence of an SE- or SE motif-containing peptide defined by an amino acid sequence selected from the group consisting of SEQ ID NOs: 1, 2, 3, 5, 6, 10, 11, 12 and 17 results in a peptide useful for counteracting or reversing disease-causing signaling defects in diseases with underlying signal transduction defects, including but not limited to AD, can be readily determined by an in vitro assay for cAMP-mediated signaling as described in the examples below. Briefly, one such assay involves the assessment of the repair of $H_2O_2$-induced DNA damage. Cells can be preincubated in the presence or absence of various SE-containing peptides, analogues or derivatives prior to induction of DNA damage.

As noted, in several embodiments, the derivatives of the present invention are peptides having sequence homology to the above-described SE sequences and motif. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. (W R Pearson and D J Lipman. Proc. Natl. Acad. Sci. (USA) 85:2444–2448 (1988); D J Lipman and W R Pearson. Science 227:1435–1441 (1985)). In the present invention, synthetic polypeptides useful in counteracting and reversing disease-causing signaling defects in diseases with underlying signal transduction aberrations, including but not limited to AD, are those peptides with statistically significant sequence homology and similarity (Z value of Lipman and Pearson algorithm in Monte Carlo analysis exceeding 6).

In yet other embodiments, SE- or SE motif-containing peptide analogues or derivatives comprise genetically engineered proteins, including, but not limited to, the hepatitis B core (HBc) protein. In these embodiments, the SE- or SE motif derivatives or analogues are engineered to be expressed at the tips of the HBc spikes. Recombinant viral particles thus comprise an SE- or SE motif-derivative or analogue on the spikes of the viral shell.

As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to formation of peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

As noted above, the present invention contemplates peptides that are protease resistant. In one embodiment, such protease-resistant peptides are peptides comprising protecting groups. In a preferred embodiment, the present invention contemplates a peptide comprising the SE or SE motif that is protected from protease degradation by N-terminal acetylation ("Ac") and C-terminal amidation. The acetylated and amidated SE- or SE motif-containing peptide is useful for in vivo administration because of its resistance to proteolysis.

In another embodiment, the present invention also contemplates peptides protected from protease degradation by substitution of L-amino acids said peptides with their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention, these mirror-image structures are called the D and L forms of the amino acid. These forms cannot be interconverted without breaking a chemical bond. With rare exceptions, only the L forms of amino acids are found in naturally occurring proteins. In one embodiment, the present invention contemplates Q(dK)RAA-[Gin (dLys) Arg Ala Ala] [SEQ ID NO: 13] containing peptides.

In other embodiments, peptides protected from protease degradation by both the use of protecting groups and substitution of L-amino acids with their corresponding D-isomers are contemplated. For example, a peptide comprising at least one D-amino acid can be acetylated and amidated as described above.

1. Calreticulin

Calreticulin is a ubiquitous multifunctional calcium-binding protein which the present inventors have found, for the first time, binds SE-containing peptides. Although originally characterized as an endoplasmic reticulum (ER) molecular chaperone, more recently it has been shown to attach to low density lipoprotein receptor-related protein (LRP/CD91/alpha-2 macroglobulin receptor) on the cell surface. See, Basu S, Binder R J, Ramalingam T and Seivastava P. CD91 is a common receptor for heat shock proteins gp96, hsp70, and calreticulin. *Immunity* 14: 303–313, 2001. Calreticulin has also been implicated in signal transduction events associated with cell adhesion, angiogenesis and apoptosis. Because calreticulin lacks transmembrane domain, LRP may serve as a partner receptor, which transduces calreticulin-triggered signaling. Both LRP and calreticulin signaling have been shown to involve intracellular NO production.

Calreticulin modulates neuronal physiology. Increased cell surface expression of this protein is associated with neurite formation and neuronal survival. See, Johnson R J, Xiao G, Shanmugaratnam J and Fine R E. Increased calreticulin stability in differentiated NG-108–15 cells correlates with resistance to apoptosis induced by antisense treatment. *Mol. Biol. Aging* 53:104–11, 1998. Additionally, calreticulin has been shown to bind neuromodulatory proteins, such as APP (intracellularly) and laminin (extracellularly). A recent study has shown that cell surface calreticulin specifically binds neuronal survival-promoting peptide Y-P30 and mediates its neuroprotective effect. Calreticulin binding and other biological activities of survival peptide Y-P30 including effects of systemic treatment of rats. *Exp Neurol* 163: 457–468, 2000.

While it is not intended that the present invention be limited to any specific mechanism, calreticulin shows decreased expression in AD neurons. Moreover, in sum, these observations implicate calreticulin dysfunction in the pathogenesis of AD.

While its role in AD may be protective, in rheumatoid arthritis (RA) calreticulin is pathological. See, Sontheimer R D, Lieu T S and Cpara J D. Calreticulin: the diverse functional repertoire of a new human autoantigen. *Immunologisti* 1:155, 1993. That is to say, in contrast to AD neurons, the expression level of this protein in RA patients in increased. Moreover, calreticulin-derived peptides (residues 295–309) have been found to bind specifically to RA-associated HLA-DRβ molecule. Once again, while it is not intended that the present invention be limited to any specific mechanism, calreticulin likely plays opposite roles in the pathogeneses of AD and RA.

2. Mimetics

Compounds mimicking the necessary conformation for biological activity of the peptides of the present invention are contemplated as within the scope of this invention. For example, mimetics of QRRAA [Gln Arg Arg Ala Ala] [SEQ ID NO: 2] and QKRAA [Gln Lys Arg Ala Ala] [SEQ ID NO: 1] containing peptides are contemplated. A variety of designs for such mimetics are possible. For example, cyclic QRRAA [Gln Arg Arg Ala Ala] [SEQ ID NO: 2] and QKRAA [Gln Lys Arg Ala Ala] [SEQ ID NO: 1] containing peptides, in which the necessary conformation for biological activity is stabilized by nonpeptides, are specifically contemplated. U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all herein incorporated by reference, describe multiple methods for creating such compounds.

Synthesis of nonpeptide compounds that mimic peptide sequences is also known in the art. Eldred et al. (J. Med. Chem. 37:3882 (1994)) describe nonpeptide antagonists that mimic an Arg-Gly-Asp sequence. Likewise, Ku et al. (J. Med. Chem. 38:9 (1995)) give further elucidation of a series of such compounds. Such nonpeptide compounds that mimic QRRAA [Gln Arg Arg Ala Ala] [SEQ ID NO: 2] and QKRAA [Gln Lys Arg Ala Ala] [SEQ ID NO: 1]-containing peptides are specifically contemplated by the invention.

The present invention also contemplates synthetic mimicking compounds that are multimeric compounds that repeat the relevant peptide sequences. In one embodiment of the present invention, it is contemplated that the relevant peptide sequence is QRRAA [Gln Arg Arg Ala Ala] [SEQ ID NO: 2]; in another embodiment, the relevant peptide sequence is QKRAA [Gln Lys Arg Ala Ala] [SEQ ID NO: 1].

In some embodiments, the invention contemplates the use of antagonists of SE- or SE motif-containing peptides. Such antagonists are expected to be inhibitory, and may produce an opposite signalling effect. Without wishing to be limited to any particular mechanism, such antagonists may bind a (presently unknown) receptor without activating it. Such antagonists are contemplated to be used to suppress NO signaling and/or to increase cAMP activation where indicated. For example, a disease such as RA is contemplated for treatment by local application of such antagonists. Antagonists may be peptides or peptidomimetic compounds. The activity of a potential antagonist may be assayed in a variety of assays, including measurement of intracellular cAMP levels, measurement of protein kinase A activation and measurement of signaling through a cAMP mediated signaling pathway, such as the induced DNA repair assay described in the examples below.

Conjugates comprising the SE- or SE motif-containing peptides, analogues, derivatives, mimetics and antagonists linked to at least one additional moiety are also contemplated. The additional moiety may be a carrier molecule, to facilitate delivery of the conjugate to the appropriate target organ or tissue. In some embodiments, the conjugates are contemplated for delivery to the brain, across the blood brain barrier. In other embodiments, the conjugates are contemplated for enhanced permeability for topical administration (for example, topical administration over a joint affected by rheumatoid arthritis).

A variety of carrier molecules are contemplated, and may vary, depending on the desired delivery or administration format. Among the carrier molecules contemplated are lipophilic or hydrophobic moieties, antibodies (and fragments thereof) and polyamines, although additional carrier molecules are also considered.

Conjugates of the SE- or SE motif-containing peptides, analogues, derivatives, mimetics and antagonists comprising the compounds of interest coupled to a lipophilic moiety are contemplated in some embodiments. U.S. Pat. No. 5,972,883 to Gozes et al., herein incorporated by reference, describes a lipophilic moiety conjugated to vasoactive intestinal peptide (or analogues and derivatives), as shown in Formula I of Gozes et al. [supra]. The present invention contemplates adapting Formula I of Gozes et al. [supra] for conjugation of at least one lipophilic moiety to an SE-containing peptide, SE motif-containing peptide, analogue, derivative, mimetic or antagonist, as shown below.

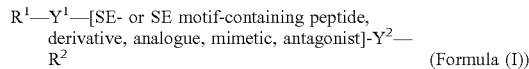

(Formula (I))

$R^1$ and $R^2$ may be the same or different and each is hydrogen, a saturated or unsaturated lipophilic group or a $C_1$–$C_4$ hydrocarbyl or carboxylic acyl, with the proviso that at least one of $R^1$ and $R^2$ is a lipophilic group;

$Y^1$ and $y^2$ may be the same or different, and each is —$CH_2$— or a bond in case the associated $R^1$ or $R^2$ is hydrogen and $Y^1$ may further be —CO—.

The lipophilic moiety which is coupled to the SE- or SE motif-containing peptides, analogues, derivatives, mimetics and antagonists is preferably a saturated or unsaturated radical such as hydrocarbyl or carboxylic acyl having at least 5 carbon atoms. The lipophilic moiety can be attached at either or both of the N-terminus and C-terminus of the peptide molecule.

In one preferred embodiment, the SE- or SE motif-containing peptides, analogues, derivatives, mimetics and antagonists are peptides of the Formula (I) above, in which $Y^1$ is —CO— and $R^1$ is a $C_5$–$C_{17}$ alkyl, with $Y^1R^1$ being, for example, stearoyl, lauroyl or caproyl, $Y^2$ is a bond and $R^2$ is hydrogen. Gozes et al. (supra) found stearoyl conjugates of vasoactive intestinal peptide derivatives to reach the brain following nasal administration.

In other embodiments, said conjugates comprise a long chain aliphatic carboxylic acid, as described in U.S. Pat. No. 5,147,855 to Gozes et al., herein incorporated by reference. Said long chain aliphatic carboxylic acid conjugate may have the long chain aliphatic carboxylic acid conjugated to the N terminus or to the C terminus. The long chain aliphatic carboxylic acid is a hydrophobic moiety having the formula —$CH_3(CH_2)_nCO$, wherein n is an integer from 6–16. In one embodiment, the long chain aliphatic carboxylic acid is a stearyl group conjugated to the SE- or SE motif-containing peptides, analogues, derivatives, mimetics and antagonists.

In other embodiments, the SE- or SE motif-containing peptides, analogues, derivatives, mimetics and antagonists may be conjugated with other molecules. In some embodiments, the other molecules may be carrier molecules, such as peptides or antibodies. For example, U.S. Pat. No. 4,902,505 to Pardridge et al., herein incorporated by reference, describes chimeric peptides suitable for neuropeptide delivery through the blood brain barrier. Briefly, such peptides include a peptide which by itself is capable of crossing the blood brain barrier by transcytosis at a relatively high rate, which is conjugated to a peptide which is only transportable at a very low rate into the brain across the blood brain barrier. Such chimeric peptides are useful in delivery of peptides (such as SE- or SE motif-containing peptides, derivatives and analogues) to the brain. Suitable blood brain barrier transportable peptides for use in such conjugates include histone, insulin, transferrin, insulin-like growth factor I, insulin-like growth factor II, basic albumin (or cationized albumin) and prolactin. The chimeric peptide conjugates are made by conjugating a transportable peptide with the SE- or SE motif-containing peptides, derivatives and analogues. The conjugation may be carried out using bifunctional reagents which are capable of reacting with each of the peptides and forming a bridge between the two. A preferred method of conjugation involves peptide thiolation, wherein the two peptides are treated with a reagent such as N-succinimidyl 3-(2-pyridylthio) propionate to form a disulfide bridge between the two peptides to form the chimeric conjugate. Other known conjugation agents may be used, so long as they provide the linkage of the two peptides together without denaturing them. Preferably, the linkage can be easily broken once the chimeric peptide conjugate has entered the brain. Suitable examples of conjugation reagents include glutaraldehyde and cystamine and EDAC. The conjugates comprising an SE- or SE motif-containing peptide, analogue, derivative, mimetic or antagonist may comprise a formulation further comprising pharmaceutically acceptable carriers and vehicles.

In other embodiments, the carrier molecule conjugated to the SE- or SE motif-containing peptides, analogues, derivatives, mimetics and antagonists is an antibody. In some embodiments, the antibody is a cationized antibody. U.S. Pat. Nos. 5,004,697 and 5,130,129, both by Pardridge and herein incorporated by reference, describe the cationization of antibodies to raise their isoelectric point in order to increase their rate of transport across the blood-brain barrier.

The use of an anti-transferrin receptor monoclonal antibody (OX26) as a carrier for a vasoactive intestinal peptide (VIP) analogue is described in Bickel et al. [Proc. Natl. Acad. Sci. USA 90:2618–2622 (1993)]. The OX26 antibody was conjugated to avidin, and this conjugate was then conjugated to a biotinylated VIP analogue. Bickel et al. [supra] note that the high concentration of transferrin receptors on brain capillary endothelia results in antibody targeting to the brain by receptor mediated transcytosis through the blood brain barrier. Bickel et al. [supra] noted an in vivo central nervous system effect (increased cerebral blood flow) following systemic infusion of the carrier-conjugate in rats, but no effect following systemic infusion of the biotinylated VIP analogue without the carrier antibody. As noted by Bickel et al. [supra], such a targeting system could be adapted for delivery of other drugs to the brain. Thus, transport of SE- or SE motif-containing peptides, analogues, derivatives, antagonists and mimetics to the brain is contemplated. For example, biotinylation of an SE- or SE motif-containing peptide, derivative, analogue or mimetic would permit conjugation to an avidin-conjugated anti-transferrin receptor antibody, either monoclonal or polyclonal. Thus, in some embodiments, a biotinylated SE- or SE motif-containing peptide, analogue, derivative, mimetic or antagonist is contemplated. In other embodiments, said biotinylated peptides, analogues, mimetics or antagonists are further conjugated to an antibody. Said antibody may be specific for the transferrin receptor, and may be a monoclonal or polyclonal antibody preparation. The monolconal or polyclonal antibody to the transferrin receptor may recognize the human transferrin receptor, or it may recognize the transferrin receptor of another subject species (for example, rat, mouse or a non-human primate). In other embodiments, said conjugation to an antibody is accomplished by using a chemical crosslinker, rather than through a biotin-avidin linkage.

In yet other embodiments, the SE- or SE motif-containing peptides, analogues, derivatives, mimetics and antagonists are in the form of conjugates with a carrier molecule comprising a naturally occurring polyamine, such as putrescine, spermidine or spermine. Conjugates of neurologically active compounds with a polyamine carrier molecule are described in U.S. Pat. No. 5,670,477 to Poduslo et al., herein incorporated by reference. Suitable polyamines and linkages are described by Podsulo et al. [supra], and one of skill in the art may apply these to the SE- or SE motif-containing peptides, analogues, derivatives, mimetics and antagonists. In some embodiments, conjugates comprising a polyamine are in a formulation comprising pharmaceutically acceptable carriers and vehicles. While not limited to any particular formulation or any particular administration, in some embodiments, such formulations are suitable for parenteral delivery of the conjugates, while in other embodiments, the formulation comprising the conjugates is suitable for intranasal administration of the conjugates.

D. Routes of Administration and Formulations

The present invention is not limited by the method of introduction of the therapeutic compound to the body. Among other methods, the present invention contemplates administering cutaneously, orally, or by standard injection (e.g. intravenous).

The present invention also contemplates administering SE- or SE motif-containing peptides, derivatives, mimetics, conjugates or antagonists to the patient intranasally or through respiratory inhalation. Formulations suitable for intranasal administration include ointments, creams, lotions, pastes, gels, sprays, aerosols, oils and other pharmaceutical carriers which accomplish direct contact between the compounds of the invention or a pharmaceutical composition comprising compounds of the invention and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all herein incorporated by reference. Formulations suitable for respiratory inhalation include ointments, creams, lotions, pastes, gels, sprays, aerosols, oils and other pharmaceutical carriers which accomplish direct contact between compounds of the invention or a pharmaceutical composition comprising compounds of the invention and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all herein incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

While the present invention is not limited by the form of oral administration, aqueous and organic solutions of SE- or SE motif-containing peptides, derivatives, analogues, mimetics, conjugates or antagonists is contemplated. Likewise, compounds of the invention can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Compounds of the present invention (i.e. SE- or SE motif-containing peptides, derivatives, analogues, mimetics, conjugates or antagonists) may also be administered cutaneously in a carrier adapted for topical administration. Such carriers include creams, ointments, lotions, pastes, jellies, sprays, aerosols, bath oils, or other pharmaceutical carriers which accomplish direct contact between the compounds of the invention and the pore of the skin. In general pharmaceutical preparations may comprise from about 0.001% to about 10%, and preferably from about 0.01 to 5% by w/w of the active compound (e.g., SE- or SE motif-containing peptides, derivatives, analogues, mimetics, conjugates or antagonists) in a suitable carrier. In some cases it may be necessary to dissolve the active compound in an appropriate solvent such as ethanol or DMSO (dimethylsulfoxide), and the like, to facilitate incorporation into a pharmaceutical preparation.

While the present invention is not limited by a specific method of introducing compounds of the invention by injection, injection of the compounds of the invention can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the patient.

Compounds of the present invention (i.e. SE- or SE motif-containing peptides, derivatives, analogues, mimetics, conjugates or antagonists) can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which compounds of the present invention are dissolved or suspended, such that the resulting composition is suitable for injection. Such a physiologically acceptable composition can also include a non-irritant preservative, such as, e.g., benzalkonium chloride at 0.05% (w/v) to 0./2% (w/v).

While the present invention is not limited to the method of injecting compounds of the present invention, in the preferred embodiment, it is injected with a standard syringe.

One skilled in the art would be capable of injecting compounds of the present invention with a carrier as described above.

In some embodiments (e.g. in a method of treating a subject with one or more symptoms of AD), it is desirable that the compositions of the invention reach the brain, as this is the primary target organ for the neuroprotective therapy. While substances pass easily from the bloodstream to cells in other parts of the body, the brain has a complex set of defenses that protect it from possible poisons. Known as the blood-brain barrier (BBB), these defenses include physical barriers, such as tightly opposed cells in the walls of the blood vessels. Another defense is chemical-enzymes that act as gatekeepers, escorting only certain substances into the inner compartments.

In some embodiments, targeting of the SE- or SE motif-containing peptide, derivative, analogue, antagonist or mimetic to the brain is desired. In such cases, delivery across the blood-brain barrier is necessary. As described above, conjugates comprising an SE- or SE motif-containing peptide, derivative, analogue, antagonist or mimetic and a carrier molecule are useful in such embodiments. As described above, the carrier molecule of the conjugate may be lipophilic moiety, a transportable peptide (including, but not limited to a histone, insulin, transferrin or basic albumin), an antibody (including, but not limited to an anti-transferrin receptor antibody) or a polyamine.

Such conjugates may be administered by any route for delivery across the blood-brain barrier. In some embodiments oral administration is contemplated. In other embodiments, parenteral administration is contemplated, including, but not limited to, intravenous injection. In yet other embodiments, intranasal administration, as an aerosol, is contemplated. Intranasal administration permits penetration of the aerosol composition to the CNS through the olfactory nerve. As described above, any pharmaceutical carrier that can be used as a vehicle for the administration of the conjugates comprising an SE- or SE motif-containing peptide, analogue, derivative, mimetic or antagonist and a carrier for delivery across the blood-brain barrier is contemplated for the pharmaceutical compositions.

In other embodiments, delivery to the brain across the blood-brain barrier is effected by direct delivery to the brain. In some embodiments, delivery to the brain is accomplished by using a subcutaneously implantable infusion reservoir and pump system, as described in U.S. Pat. No. 4,588,394 to Schulte et al., herein incorporated by reference. The implantable infusion reservoir and pump system of Schulte et al. [supra] includes a variable capacity reservoir for receiving and storing fluids containing medications for delivery to a catheter which directs the medications to a specific infusion location in the body. A pump and valving arrangement is interposed between the reservoir and the catheter to facilitate and control the transfer of the medications from the reservoir to the catheter in a safe and efficient manner. Schulte et al. [supra] describes placement of the catheter in the body for the delivery of morphine or other pain killing medications directly into the lateral ventricle of the brain in the treatment of terminally ill patients. One of skill in the art would be able to use and adapt the implantable infusion reservoir and pump system of Schulte et al. [supra] for the direct administration of SE- or SE motif-containing peptides, analogues, derivatives, mimetics, conjugates and antagonists directly to the brain of a subject. In some embodiments, such administration is contemplated for the treatment of Alzheimer's disease.

Another pump system which may be used in delivering SE- or SE-motif containing peptides, analogues, derivatives, conjugates, mimetics and antagonists directly to the brain is described in U.S. Pat. No. 6,042,579 to Elsberry et al., herein incorporated by reference. Elsberry et al. [supra] describe a method of treatment of a neurodegenerative disorder by means of an implantable pump and a catheter having a proximal end coupled to the pump and having a discharge portion for infusing into the brain therapeutic dosages of one or more nerve growth factors. The catheter is implanted in the brain so that the discharge portion lies adjacent to a predetermined infusion site of the brain, such as the neuropil, the intraventricular space, or the subarachnoidal space. One skilled in the art would be able to use and adapt the system and method described by Elsberry et al. [supra] for the administration of SE- or SE motif-containing peptides, analogues, derivatives, mimetics, conjugates or antagonists directly to specific regions of the brain of a subject.

Another implantable system is described in U.S. Pat. No. 5,643,207 to Rise, herein incorporated by reference. Rise [supra] describes an implantable system for infusing an agent into an organ containing an endogenous fluid, including an implantable reservoir for the agent and implantable first and second catheters implanted into the organ. An implantable pump transmits the endogenous fluid to the organ through one catheter and returns it through the other catheter. A predetermined quantity of the agent is added from the reservoir to the endogenous fluid to facilitate buffering and dilution of the agent before administration to the organ. One of skill in the art would be able to use and adapt the system described by Rise [supra] for administration of SE- or SE motif-containing peptides, analogues, derivatives, conjugates, mimetics and antagonists directly to the brain of a subject.

As an alternative to implantable pump systems, an implantable therapy system is contemplated in some embodiments. U.S. Pat. No. 6,179,826 B1 to Aebischer et al., herein incorporated by reference, describes an implantable, retrievable therapy device useful for the sustained and controlled delivery of a biologically active factor to a subject, and more particularly, a device which can deliver a biologically active factor to a localized region in the central nervous system of a subject. A biocompatible vehicle containing a biologically active factor is inserted and positioned at the treatment site. Biocompatible vehicles and systems for the positioning and implantation of the biocompatible vehicles containing a biologically active factor are described by Aebischer et al. [supra] and may be used and adapted by one of skill in the art for the administration of SE- or SE motif-containing peptides, analogues, derivatives, conjugates, mimetics or antagonists to the brain of a subject.

In other embodiments, a polymeric delivery system for the delivery of SE- or SE motif-containing peptides, analogues, derivatives, mimetics, conjugates and antagonists is contemplated. Such a system is described in U.S. Pat. No. 5,601,835 to Sabel et al., herein incorporated by reference. The delivery system is preferably implanted in the central nervous system for delivery directly to the central nervous system for the treatment of disorders. Continuous delivery directly into the brain for an extended time period can be achieved with these systems. The delivery device is a two-phase system which is manufactured using standard techniques such as blending, mixing or the equivalent thereof, following selection of the material to be delivered and an appropriate polymer for formation of the matrix. The active substance is dispersed within the devices to create channels and pores to the surface for release of the active substance at the desired rate. One of skill in the art would be able to use and adapt the polymeric drug delivery systems of Sabel et al. [supra] for the delivery of SE- or SE motif-containing peptides, analogues, mimetics, conjugates and antagonists directly to the brain of a subject.

In addition to the methods for delivering SE- or SE motif-containing peptides, derivatives, analogues, conjugates, mimetics and antagonists across the blood brain barrier described above, one of skill in the art will recognize that there are numerous other delivery systems suitable for delivery across the blood brain barrier, and that any suitable method may be employed in the methods of treatment described herein. For example, drug (or active substance) nanoparticles may be employed, as described in U.S. Pat. No. 6,117,454 to Kreuter et al., herein incorporated by reference.

Alternatively, a redox chemical delivery system, as described in U.S. Pat. Nos. 5,624,894; 5,525,727 and 5,618,803 to Bodor, herein incorporated by reference, may also be used. For example, a redox targetor (such as, for example, a dihydropyridine/pyridinium salt redox carrier) is linked to the substance of interest (such as, for example, an SE- or SE motif-containing peptide, derivative, analogue, mimetic or antagonist), and in its reduced form, can transport the substance of interest across the blood brain barrier. Once across the blood brain barrier, oxidation of the redox targetor effectively traps the substance of interest in the brain. Enzymatic processes in the brain result in sustained release of the substance of interest within the brain.

Similarly, liposomes may be employed for passage across the blood brain barrier, as described in U.S. Pat. No. 6,132,764 to Li et al., herein incorporated by reference. The liposomes may be polymerized, or may have targeting molecules at their surface to promote delivery to particular organs. Block copolymers, which form micelles, can also be employed, as described in U.S. Pat. No. 6,153,193 to Kabanov et al., herein incorporated by reference. Thus, one of skill in the art can take advantage of a plurality of delivery systems appropriate for directing SE- or SE motif-containing peptides, derivatives, analogues, mimetics, conjugates or antagonists across the blood brain barrier to the brain.

In other embodiments (e.g. in a method of treating a subject with symptoms of RA), it is desirable that the compositions of the invention reach the affected joints. In some embodiments, this may be accomplished by cutaneous or transdermal application of pharmaceutical compositions comprising the compounds of the invention (e.g. antagonists of SE- or SE motif-containing peptides) directly to the skin over the affected joint. In other embodiments, delivery of the compounds to the affected joints may be by direct injection into the joint. The present invention specifically contemplates intra-articular injections in RA patients.

To perform an arthrocentesis, the specific area of the joint to be injected is palpated and is then marked, e.g., with firm pressure by a ballpoint pen that has the inked portion retracted. This will leave an impression that will last 10 to 30 minutes. (The ballpoint pen technique can also be used with soft tissue injection.) The area to be aspirated and/or injected should be carefully cleansed with a good antiseptic, such as one of the iodinated compounds. Then the needle can be inserted through the ballpoint pen impression.

Helpful equipment includes the following items: alcohol sponges; iodinated solution and surgical soap; gauze dressings (2×2); sterile disposable 3-, 10- and 20-ml syringes; 18- and 20-gauge, 1½-inch needles; 20-gauge spinal needles; 25-gauge, ⅝-inch needles; plain test tubes; heparinized tubes; clean microscope slides and coverslips; heparin to add to heparinized tubes if a large amount of inflammatory fluid is to be placed in the tube; fingernail polish to seal wet preparation; chocolate agar plates or Thayer-Martin medium; tryptic soy broth for most bacteria; anaerobic transport medium (replace periodically to keep culture media from becoming outdated); tubes with fluoride for glucose; plastic adhesive bandages; ethyl chloride; hemostat; tourniquet for drawing of simultaneous blood samples; and 1 percent lidocaine.

Knee. The knee is the easiest joint to inject. The patient should be in a supine position with the knee fully extended. The puncture mark is made just posterior to the medial portion of the patella, and an 18- to 20-gauge, 1½-inch needle directed slightly posteriorly and slightly inferiorly. The joint space should be entered readily. On occasion thickened synovium or villous projections may occlude the opening of the needle, and it may be necessary to rotate the needle to facilitate aspiration of the knee when using the medial approach. An infrapatellar plica, a vestigal structure that is also called the ligamentum mucosum, may prevent adequate aspiration of the knee when the medial approach is used. However, the plica should not adversely affect injections or aspirations from the lateral aspect.

Shoulder. Injections in the shoulder are most easily accomplished with the patient sitting and the shoulder externally rotated. A mark is made just medial to the head of the humerus and slightly inferiorly and laterally to the coracoid process. A 20- to 22-gauge, 1½-inch needle is directed posteriorly and slightly superiorly and laterally. One should be able to feel the needle enter the joint space. If bone is hit, the operator should pull back and redirect the needle at a slightly different angle.

The acromioclavicular joint may be palpated as a groove at the lateral end of the clavicle just medial to the shoulder. A mark is made, and a 22- to 25-gauge, ⅝- to 1-inch needle is carefully directed inferiorly. Rarely is synovial fluid obtained.

The sternoclavicular joint is most easily entered from a point directly anterior to the joint. Caution is necessary to avoid a pneumotharax. The space is fibrocartilaginous, and rarely can fluid be aspirated.

Ankle Joint. For injections of the compounds of the present invention in the ankle joints, the patient should be supine and the leg-foot angle at 90 degrees. A mark is made just medical to the tibialis anterior tendon and lateral to the medial malleolus. A 20- to 22-gauge, 1½-inch needle is directed posteriorly and should enter the joint space easily without striking bone.

Subtalar Ankle Joint. Again, the patient is supine and the leg-foot angle at 90 degrees. A mark is made just inferior to the tip of the lateral mallcolus. A 20- to 22-gauge, 1½-inch needle is directed perpendicular to the mark. With this joint the needle may not enter the first time, and another attempt or two may be necessary. Because of this and the associated pain, local anesthesia may be helpful.

Wrist. This is a complex joint, but fortunately most of the intercarpal spaces communicate. A mark is made just distal to the radius and just ulnar to the so-called anatomic snuff box. Usually a 24- to 26-gauge, ⅝ to 1-inch needle is adequate, and the injection is made perpendicular to the mark. If bone is hit, the needle should be pulled back and slightly redirected toward the thumb.

First Carpometacarpal Joint. Degenerative arthritis often involves this joint. Frequently the joint space is quite narrowed, and injections may be difficult and painful. A few simple maneuvers may make the injection fairly easy, however. The thumb is flexed across the palm toward the tip of the fifth finger. A mark is made at the base of the first metacarpal bone away from the border of the snuff box. A 22- to 26-gauge, ⅝ to 1-inch needle is inserted at the mark and directed toward the proximal end of the fourth metacarpal. This approach avoids hitting the radial artery.

Metacarpophalalangeal Joints and Finger Interphalangral Joints. Synovitis in these joints usually causes the synovium to bulge dorsally, and a 24- to 26-gauge, ½ to ⅝-inch needle can be inserted on the either side just under the extensor tendon mechanism. It is not necessary for the needle to be interposed between the articular surfaces. Some prefer having the fingers slightly flexed when injecting the metacarpophalangeal joints. It is unusual to obtain synovial fluid. When injecting, a mix of the compounds of the present invention with a small amount of local anesthetic is also contemplated.

Metatarsophalangeal Joints and Toe Interphalangeal Joints. The techniques are quite similar to those of the metacarpophalangeal and finger interphalangeal joints, but many prefer to inject more dorsally and laterally to the extensor tendons. Marking the area(s) to be injected is helpful as is gentle traction on the toe of each joint that is injected.

Elbow. A technique preferred by many is to have the elbow flexed at 90 degrees. The joint capsule will bulge if there is inflammation. A mark is made just below the lateral epicondyle of the humerus. A 22-gauge, 1 to 1½-inch is inserted at the mark and directed parallel to the shaft of the radius or directed perpendicular to the skin.

Hip. This is a very difficult joint to inject even when using a fluoroscope as a guide. Rarely is the physician quite sure that the joint has been entered; synovial fluid is rarely obtained. Two approaches can be used, anterior or lateral. A 20-gauge, 3½-inch spinal needle should be used for both approaches.

For the anterior approach, the patient is supine and the extremity fully extended and externally rotated. A mark should be made about 2 to 3 cm below the anterior superior iliac spine and 2 to 3 cm lateral to the femoral pulse. The needle is inserted at a 60 degree angle to the skin and directed posteriorly and medially until bone is hit. The needle is withdrawn slightly, and possibly a drop or two of synovial fluid can be obtained, indicating entry into the joint space.

Many prefer the lateral approach because the needle can "follow" the femoral neck into the joint. The patient is supine, and the hips should be internally rotated—the knees apart and toes touching. A mark is made just anterior to the greater trochanter, and the needle is inserted and directed medially and sightly cephalad toward a point slightly below the middle of the inguinal ligament. One may feel the tip of the needle slide into the joint.

Temporomandibular Joint. For injections, the temporomandibular joint is palpated as a depression just below the zygomatic arch and 1 to 2 cm anterior to the tragus. The depression is more easily palpated by having the patient open and close the mouth. A mark is made and, with the patient's mouth open, a 22-gauge, ½ to 1-inch needle is inserted perpendicular to the skin and directed slightly posteriorly and superiorly.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); ° C. (degrees Centigrade); FSK (forskolin); SEM (standard error of the mean); Ci (Curies)

EXAMPLE 1

In this example, various assays used to detect intercellular and intracellular signaling events are presented.

Protein Kinase A Activity Assay

Protein kinase A (PKA) was measured using the Life Technologies™ Protein Kinase A (cAMP-dependent Protein Kinase) Assay System (Cat. No. 13128-012). The basis of the assay system is the use of a heptapeptide substrate and a 17-amino acid inhibitor peptide (which is valuable for proving PKA-specific protein kinase activity). Four assay conditions per experimental condition are recommended by the manufacturer (+/−inhibitor and +/−cAMP) to determine total PKA-specific kinase activity and proportion of PKA activated in the cells or tissue of interest. Briefly, the four parallel assay conditions are set up for each of the four assay conditions for a given cell or tissue sample, according to the manufacturer's instructions. Substrate and [γ-$^{32}$P]ATP (3000–6000 Ci/mmol stock solution) are then added to each tube, and incubated according to the manufacturer's instructions. Following the incubation period, a sample from each tube is spotted onto a nitrocellulose disc, which is the acid washed prior to scintillation counting (all according to the manufacturer's instructions). Activity can then be determined as described by the manufacturer of the kit.

cAMP Assay cAMP was determined by using an Amersham Pharmacia Biotech cAMP enzymeimmunoassay (EIA) system (code RPN 225). The reagents are prepared as described by the manufacturer (lysis reagents 1 and 2, the standard for the non-acetylation assay, the anti-cAMP antiserum, the cAMP peroxidase conjugate and wash buffer). Briefly, a microtiter plate is prepared as suggested by the manufacturer. Samples are added, followed by the antiserum solution. Following the recommended incubation, cAMP-peroxidase conjugate is added and incubated according to the recommended protocol. Each well is then aspirated and washed, and enzyme substrate is added and incubated. The results can then be read at 630 nm or at 450 nm (depending on the time of incubation and method of stopping the reaction), again according to the manufacturer's protocol.

cGMP Assay cGMP was determined using an Amersham Pharmacia Biotech cGMP enzymeimmunoassay (EIA) system (Code RPN 226). The reagents (lysis reagents, standards, antibody, cGMP conjugate and wash buffer) are all prepared according to the manufacturer's instructions. Briefly, samples are acetylated with acetylation reagent (acetic anhydride in triethylamine) and then incubated with the antibody reagent and lysis buffer according to the manufacturer's instructions. The cGMP conjugate is then added and the microtiter plate is incubated according to the manufacturer's instructions. The wells are aspirated and washed, enzyme substrate is added and incubated, and the plate can be read at 630 nm or 450 nm (depending on the length of incubation and how the reaction was terminated). Controls are carried out as recommended by the manufacturer, and the results are calculated according to the manufacturer.

Nitrate/Nitrite Assay

Nitrate/Nitrite are assayed using the Cayman Chemical Company Nitrate/Nitrite Colorimetric Assay Kit (LDH Method) (Catalog No. 760871). Briefly, the assay uses an excess of NADPH, an essential cofactor for the nitric oxide synthase enzyme (NOS), and then uses lactate dehydrogenase (LDH) to destroy the excess NADPH. NOS activity, as well as nitrate and nitrite in urine, plasma, serum and tissue culture medium can all be assayed with this kit. Nitrite and nitrate measurement are carried out as described by the manufacturer, which includes a nitrate standard curve. Samples are added to assay buffer in microtiter wells, followed by NADPH and nitrate reductase mixture. The samples are then incubated for 40 or 60 minutes at room temperature (depending on the sample). Cofactor solution and LDH solution are then added and incubated for 20 minutes at room temperature. Greiss reagents are then successively added, and the absorbance at 540 or 550 nm is read following a 10 minute incubation at room temperature. All steps are carried out according to the manufacturer's protocol. Calculations of nitrate and nitrite are then carried out as described by the manufacturer.

Comet Assay

In related studies, the inventors have found that DNA repair proteins (118) and activity can be induced through extracellular signaling. To further determine the signaling pathways involved in DNA repair induction, the inventors used the Trevigen CometAssay™ kit (Cat. No. 4250-50-K). The CometAssay is a single-cell gel electrophoresis method that can measure a variety of types of DNA damage, and repair of damage, in individual cells. The assay is based on the alkaline lysis of labile DNA at sites of damnage. The unwound, relaxed DNA is able to migrate out of the cell during electrophoresis and can be visualized by SYBR Green staining. Cells that have accumulated DNA damage appear as fluorescent comets with tails of DNA fragmentation or unwinding, whereas normal undamaged DNA does not migrate far from the origin.

After cells have been preincubated with various compounds of interest, cells are collected, washed, and subjected to DNA damage with 100 µM $H_2O_2$ at 4° C. for 20 min. To quantify DNA damage, cells were collected and three parallel samples were processed (a negative control, a DNA damage control ($H_2O_2$) and a sample subjected to $H_2O_2$ following exposure to various modulators of the cAMP signaling pathway). Cells are then washed in PBS. The washed cells are combined with molten low-melting agarose (Trevigen Cat. No. 4250-50-02) and transferred to a CometSlide™ (Trevigen Cat. No. 4250-100-03). The slides are immersed in lysis buffer for 30 min, on ice, in the dark. The slides are then treated with alkali buffer for 20 to 60 min at room temperature in the dark. The slides are then electrophoresed in buffer for 10 min at 20 volts, then fixed in methanol and ethanol. The slides are then stained with SYBR green (Trevigen Cat. No. 4250-50-05) solution and fluorescently imaged with a Diagnostic Instruments digitized camera, mounted on a Nikon Eclipse E400 microscope. Scion Image software is used to quantitate the comet tail intensity. Each data point is derived from tail fluorescent intensity determination in 50–100 individual cells. Data is presented as % DNA repair (the percent decrement in tail fluorescence intensity in agonist or antagonist-treated cells, relative to the intensity recorded in cells treated with $H_2O_2$ only) ±SEM.

Figure 2:
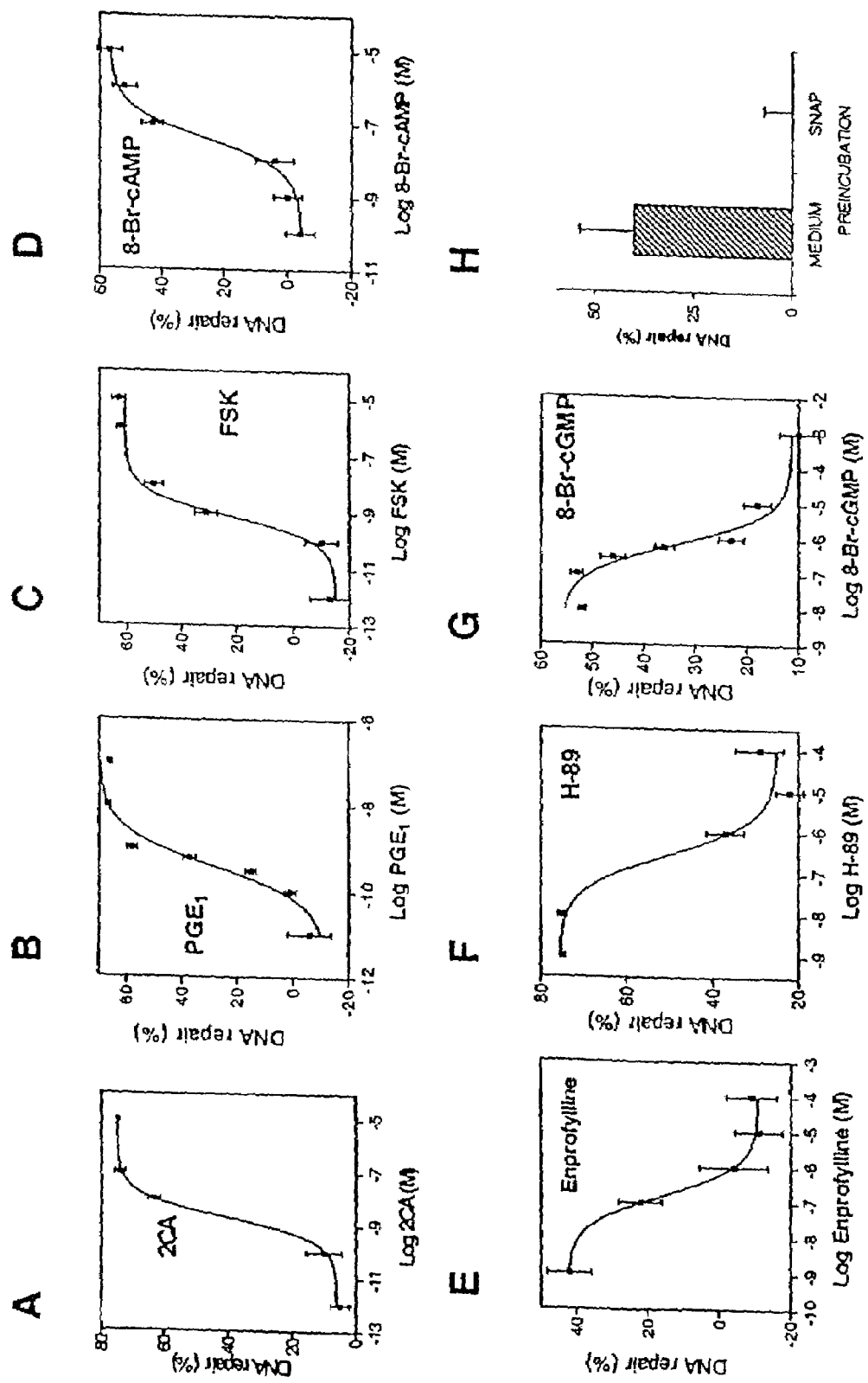
FIG. 2 depicts the experimental results confirming that inducible DNA repair signaling is transduced through a cAMP-dependent pathway.

The Comet Assay is an Accurate and Reproducible Readout System to Determine Signaling Through the cAMP-PKA Pathway. Using this system, the inventors established that in normal cells, induction of DNA repair activity is mediated by a Gs protein-coupled receptor-dependent pathway. As shown in FIG. 2, stimulation of the human fibroblastoid line M1 cells for 20 min with various concentrations of either prostaglandin E1 ($PGE_1$) (FIG. 2B), 2-chloro adenosine (2CA) (FIG. 2A), FSK (FIG. 2C) or 8-Br-cAMP (FIG. 2D) triggered in all cases DNA repair. M1 cells express the $A_{2b}$, but not the $A_{2a}$ subset of Gs protein-coupled adenosine receptors (data not shown). Indeed, as shown in FIG. 2, DNA repair activity, triggered by 10 µM 2CA, could be blocked by co-incubation with various concentrations of the adenosine receptor $A_{2b}$ antagonist, enprofylline (FIG. 2E) and by the non-selective adenosine receptor antagonist XAC, but not by the $A_{2a}$-selective antagonist, CSC (data not shown). 10 µM 2CA-triggered DNA repair could also be blocked by co-incubation with various concentrations of the specific PKA inhibitor, H-89, (FIG. 2F). Additionally, S-Nitroso-N-Acetylpenicillamine (SNAP), a NO donor, and a membrane-permeable cGMP analog, 8-Br-cGMP, completely blocked 10 µM 2CA-induced DNA repair (FIG. 2H and FIG. 2G, respectively).

Figure 3:
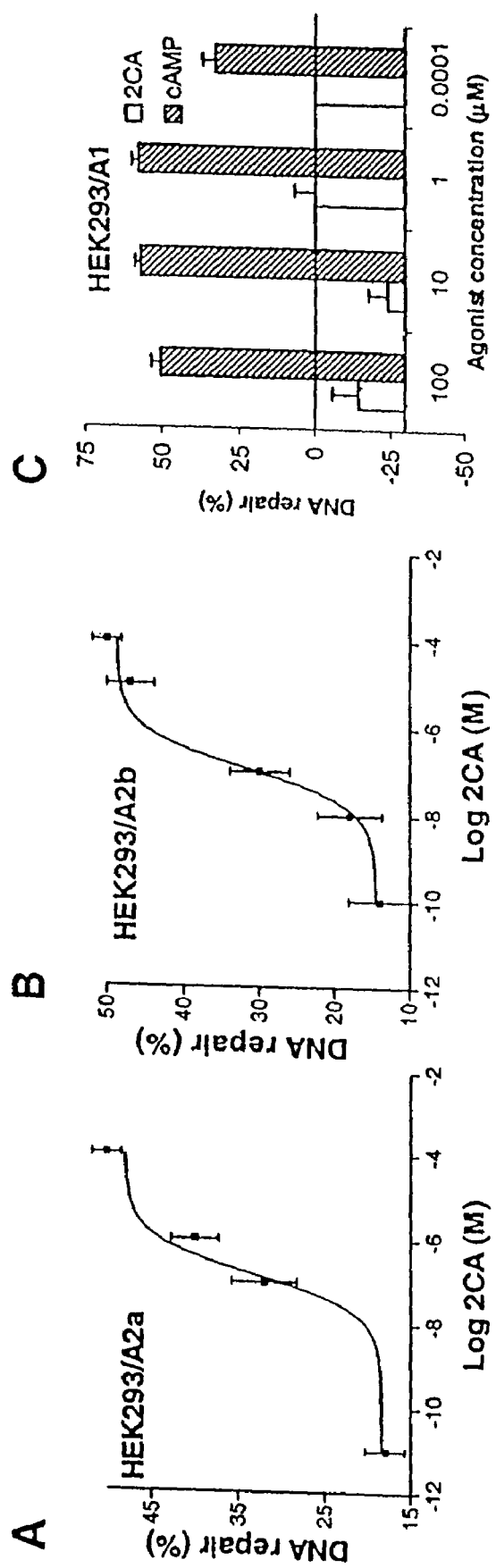
FIG. 3 depicts the experimental results assessing the role of Gs protein-coupled receptors in the inducible DNA repair signaling.

The extracellular signaling is transduced by Gs-protein coupled receptors, as evidenced by using adenosine receptor type-selective agonists and antagonists (not shown), and more conclusively, by using HEK293 cell transfectants (FIG. 3).

Human embryonic kidney 293 cells (HEK 293) transfected with adenosine receptors were provided by Joel Linden. The preparation of the HEK 293 transfectants is described in Linden et al. [Molecular Pharmacology 56:705–713 (1999)]. Briefly, the procedure carried out, as described in Linden et al. [supra] involved subcloning the cDNA for human $A_1$ adenosine receptor, human $A_{2B}$ adenosine receptor or human $A_{2A}$ adenosine receptor into the expression plasmid CLDN10B. The plasmids were amplified in competent JM109 cells and plasmid DNA isolated by using Wizard Megaprep columns (Promega Corporation, Madison, Wis.). Recombinant vectors were introduced into HEK 293 cells by lipofectin. Colonies were selected by growth of cells in 0.6 mg/ml G418. Stably transfected cells were maintained in Dulbecco's modified Eagle's medium/Ham's F12 medium with 10% fetal calf serum, 100 U/ml penicillin, 100 µg/ml streptomycin and 0.3 mg/ml G418.

Cells were pretreated for 20 min with various doses of 2CA before exposure to 100 µM $H_2O_2$ as above. As can be seen, HEK293 cell transfectants expressing the Gs-coupled adenosine receptors, $A_{2a}$ (FIG. 3A) or $A_{2b}$ (FIG. 3B), but not the Gi protein-coupled adenosine receptor A1 (FIG. 3C), transduced the signal. HEK293 cells transfected with $A_1$ adenosine receptors were not inherently resistant to cAMP signaling, as pretreatment with various doses of a membrane-permeable cAMP analog, 8-Br-cAMP triggered comparable responses in those cells (FIG. 3C).

Thus, it is concluded that under physiological conditions, DNA repair activity can be induced either by extracellular agonists capable of signaling through Gs-coupled receptors, or by agents capable of intracellular activation of the cAMP-PKA pathway. This system allows highly reproducible detection of intracellular cAMP concentration shifts at a sub-nanomolar range and is highly sensitive to both cAMP and NO changes and as such is suitable for accurate determination of cAMP and NO signaling events.

It is noteworthy that recent studies have demonstrated increased expression and enzymatic activity of DNA excision repair proteins in brain tissues of AD patients. It has been suggested that the pathology seen in AD may represent an excessive effort to repair aging-related DNA damage (discussed in Schmitz C et al. [*Acta Neuropathol* 97:71–81 (1999)]). Relevant to this notion, ERCC1 and 2 (excision repair proteins), APLP1 and ApoE are all located on chromosome 19q13 in an intriguingly close proximity. It is of interest that RA, which has been found to associate with reduced DNA repair activity [McCurdy D et al. *Radiat Res* 147:48–54 (1997); Colaco C B et al. *Clin Exp Immunol* 72:15–19 (1988)] has also been shown to protect against AD. Thus, it is conceivable that the comet assay system described above is not only an accurate and convenient readout system for intracellular cAMP-dependent signaling events, but may also be directly relevant to the pathogenesis of AD.

EXAMPLE 2

In this example, results of experiments carried out are presented to demonstrate that SE-expressing cells have impaired cAMP signaling.

Given the negative association between RA and AD and the postulated role of the cAMP-PKA pathway in the latter disease, it was of interest to determine the efficiency of signaling through that pathway in RA. As can be seen in FIG. 1A, lymphoblastoid B cell lines from 23 patients with RA displayed markedly lower PKA activation following stimulation with forskolin (FSK), compared to the control group of 16 healthy controls. PKA activation was determined 14 minutes following stimulation with 25 µM FSK. Results are shown as percent of maximal activity, relative to the response with the manufacturer's control (cAMP) provided with the kit. Similarly, PKA activation by $PGE_1$ in lymphoblastoid lines from 8 RA patients were significantly lower than the activation in 5 normal lines (p<0.001, data not shown). Equally diminished responses could be found in freshly isolated peripheral blood T cells of RA patients, compared to healthy controls (data not shown).

To assess the role of the RA SE, homozygous tissue-typing lines expressing either the DRB1*0401 or DRB1*0404 alleles were tested. As shown in FIG. 1A, SE-expressing lines displayed resistance to PKA activation, similar to the RA group. Control lines, homozygous for other DRB1 alleles showed normal FSK-induced PKA activation (data not shown). PKA activation was determined 14 minutes following stimulation with 25 µM FSK. Results are shown as % of maximum activity, relative to the response with the manufacturer's positive control (cAMP) provided with the kit. Taken together, these results demonstrate an association between the RA SE and the cAMP-PKA signaling pathway defect.

To more directly assess the role of the SE in cAMP signaling, L cell transfectants expressing different DRβ*04 chains were used. The L cell transfectants were donated by Robert Karr, and are described in Drover et al. [*Human Immunology* 40:51–60 (1994)]. The transfectants, as described in Karr et al. [supra] are cells of the DAP.3 sublcone of the class-II-negative murine L-cell fibroblasts that had been transfected with DRB cDNA constructs as described in Klohe et al. [*J Immunology* 141:2158–2164 (1988)]. Briefly, Klohe et al. [supra] describe maintaining cells of the DAP.3 sublcone of class II-negative murine L cell fibroblasts in Eagles MEM with 10% fetal calf serum and 2 mM glutamine. The cells were transfected using the calcium phosphate co-precipitation method, using 20 µg each of the plasmids containing the class II chain DNA and 1 µg of the pSV2-neo plasmid, which contains the neomycin resistance gene. The DNA precipitates were incubated with the cells for 18 hours before removal of the medium and replacement with fresh, complete medium. At 48 hours after addition of the DNA to the cells, the medium was removed and complete medium containing 1 mg/ml of the neomycin analog G418 was added. After 48 hours, the medium was removed and complete medium containing G418, 250 µg/ml, was added and was subsequently changed twice weekly. After the appearance of G418-resistant colonies of transfectants (2 to 3 weeks), the cells were detached from the tissue culture plastic with a trypsin-EDTA solution, and an aliquot of cells from each transfection was cultured overnight in selection media in a bacteriologic petri dish, and class II-expressing transfectants were identified by immunofluorescence.

As shown in FIG. 1B, transfectants L565 (expressing DRβ*0401; squares) and L300 (DRβ*0404; rhombus) showed markedly reduced FSK-induced PKA activation compared to L514 (DRβ*0402; not shown) and L259 (DRβ*0403; triangles). Cells were stimulated with FSK as above and PKA activity was determined at different time points. Data points represent the mean±SEM of 3–5 experiments.

Amino acids Q70 [Gln70], K/R71 [Lys/Arg71] and A74 [Ala74] have been previously identified as key residues in the SE-related RA susceptibility. To examine the contribution of each of those residues to the observed signaling defect, L-cell transfectants with single point mutations in positions 70, 71 or 74 were used (FIG. 1C). Alleles *0404 and *0403 differ by a single amino acid in position 74, alanine versus glutamic acid, respectively. As can be seen, substitution of alanine 74 in DRβ*0404 to glutamic acid (thereby converting it to a DRβ*0403-like sequence; A74E [Ala74Glu]) restored PKA activation, while substitution of glutamic acid 74 with alanine in DRβ*0403 (converting it to DRβ*0404-like sequence; E74A [Glu74Ala]) caused inhibition of that kinase activity. Interestingly, substitution of glutamine to aspartic acid in position 70 (Q70D [Gln70Asp]) restored PKA activation in DRβ*0404 transfectants, while the same substitution in DRβ*0403 produced an opposite effect. Other substitutions examined are: R71K [Arg71Lys], substitution of arginine to lysine in position 71; R71E [Arg71Glu], substitution of arginine to glutamic acid in position 71. Data points represent the mean±SEM of 3–5 experiments of FSK-induced PKA activation in L cells expressing either the wild type (WT) DRβ*0403 (closed bars), DRβ*0404 (open bars), or mutants thereof with single amino acid substitutions on the DRβ chain. Thus, the impact of residue 70 may be determined in the context of residue 74. The data presented here directly implicate for the first time the SE in a signaling aberration.

Figure 4:
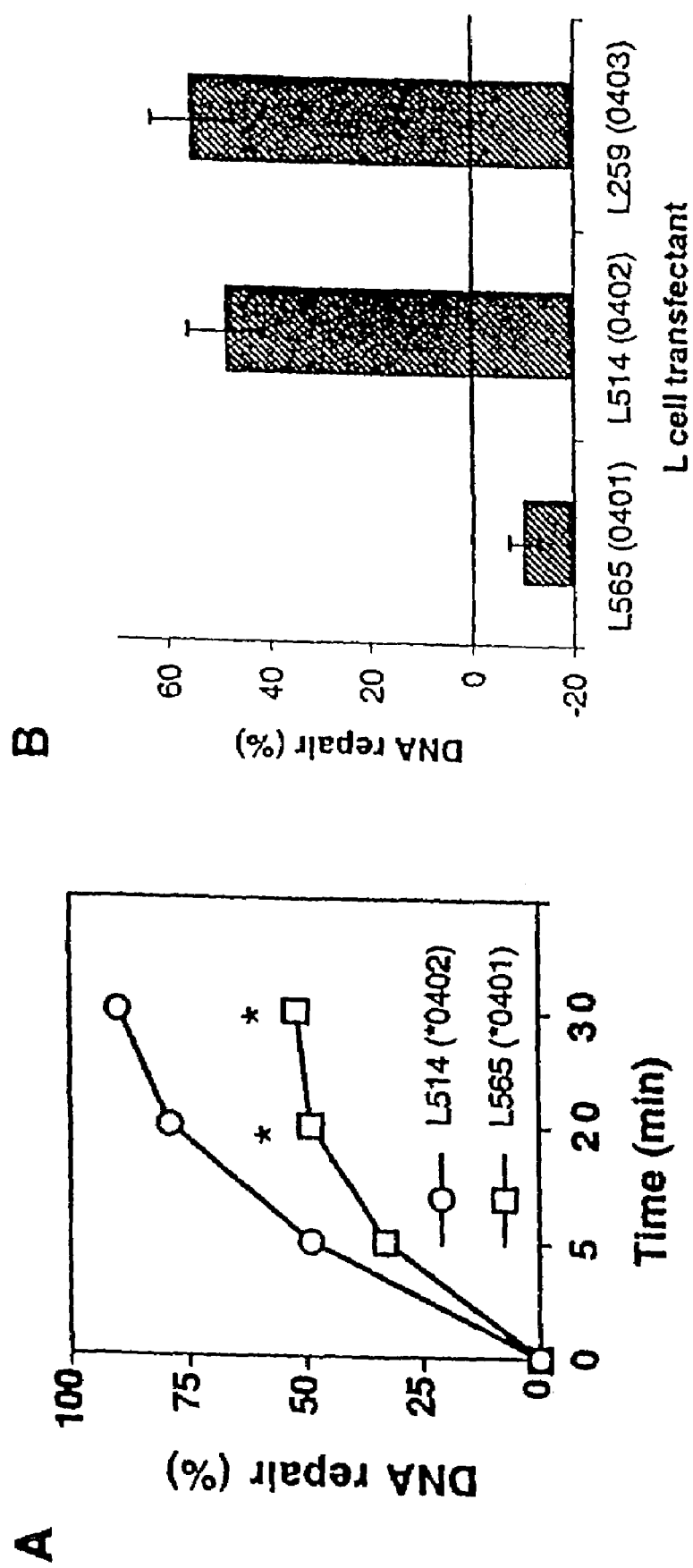
FIG. 4 depicts the experimental results demonstrating that SE-expressing DRB1 alleles have a direct inhibitory effect on cAMP-dependent signaling.

As could be predicted from their diminished cAMP-mediated signaling, SE-expressing cells displayed diminished DNA repair activity. FIG. 4A shows a time-course determination of spontaneous DNA repair activity following genotoxic damage by $H_2O_2$ in murine L cell transfectants expressing the DRβ*0401 (L565, squares) or DRβ*0402 (L514, circles) chains. Cells were treated with $H_2O_2$ and spontaneous DNA repair was determined as above at different time points. There was no significant difference in the extent of DNA damage at time zero between cell lines. However, as can be seen, L565 cells (DRB1*0401 transfectants) showed markedly reduced spontaneous repair ability over time compared to L514 (DRB1*0402) (FIG. 4A) and L259 (DRB1*0403) transfectants (FIG. 4B). In FIG. 4B, the L cell transfectants were pre-treated for 30 minutes with 10

µg/ml of cholera toxin before the induction of DNA damage with a 20 minute exposure to hydrogen peroxide and determining DNA repair as above. Similar patterns were observed in the human fibroblastoid line M1 expressing the DRβ*0401 chain (not shown). Additionally, protein extracts of lymphoblastoid B cell lines from RA patients and DRB1*0401 or *0404 homozygous tissue typing lines demonstrated much less efficient in-vitro repair of WV-damaged plasmids, compared to extracts from control lines (data not shown). Thus, it is concluded that cells expressing the RA-SE display diminished spontaneous DNA repair activity.

EXAMPLE 3

In this example, results of experiments carried out to address the effects of SE-containing peptides on cAMP-mediated DNA repair induction following application of such peptides to cells are presented.

Figure 5:
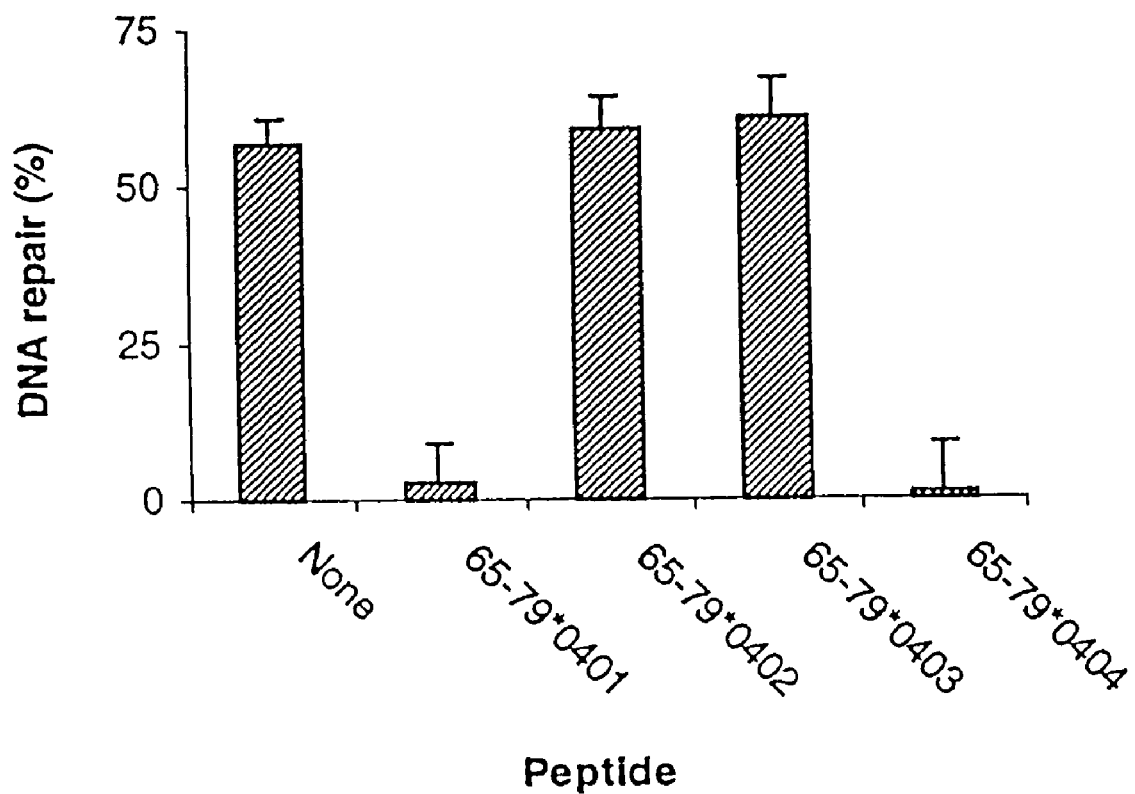
FIG. 5 is a bar graph which depicts the experimental results demonstrating that SE-containing peptides inhibit cAMP-mediated DNA repair.

As suggested by the data shown in FIG. 1, the cAMP-inhibiting domain of the RA-SE maps to the third allelic hypervariable region of the DRβ protein. To directly examine that possibility, cells were incubated overnight with synthetic peptides corresponding to the region contained within amino acids 65–79 and their ability to mount DNA repair activity in response to cAMP-elevating agents was determined. M1 cells were preincubated overnight with 50 µg/ml of synthetic peptides corresponding to the region surrounding the third allelic hypervariable region (aa 65–79) of each of the following DRβ chains: *0401 (65–79*0401) [SEQ ID NO: 5], *0402 (65–79*0402) [SEQ ID NO: 7], *0403 (65–79*0403) [SEQ ID NO: 9] or *0404(65–79*0404) [SEQ ID NO: 10]. At the end of the preincubation, cells were collected, washed and 2CA-induced DNA repair was determined as above. Table 3 (above) lists the different third allelic hypervariable region peptides used in the entire study disclosed here. As shown in FIG. 5, peptides corresponding to the third allelic hypervariable region of the RA-SE-expressing DRB1 alleles *0401 [SEQ ID NO: 5] and *0404 [SEQ ID NO: 10], but not peptides corresponding to that region in the control alleles *0402 [SEQ ID NO: 7] or *0403 [SEQ ID NO: 9], inhibited cAMP-mediated DNA repair induction in both human (FIG. 5) and mouse cells (data not shown). The $IC_{50}$ of the 65–78*0401 [SEQ ID NO: 6] peptide was ~250 nM.

To determine whether the inhibitory activity by the RA SE-derived peptides is due to an extracellular or intracellular effect, peptides conjugated to Sepharose beads were tested. Sepharose beads were chemically conjugated to 14-mer peptides corresponding to residues 65–78 of DRβ*0401 chain [SEQ ID NO: 6] (Beads*0401) or DRβ*0402 chain [SEQ ID NO: 8] (Beads*0402).

A modified method as described previously by Auger et al. [Nature Med 2:306–310 1996] was used. Briefly, cyanogen bromide activated Speharose 4B (1.5 ml) was washed with 1 mM HCl and incubated with peptides in 0.1 M $NaHCO_3$ and 0.5 M NaCl (pH 8) buffer overnight at 4° C. For each peptide, 5 mg was used per milliliter of Sepharose. Free Sepharose groups were blocked with 0.2 M glycine (pH 8) for 2 hours at room temperature. Columns were washed at 4° C. with the following buffers: 0.1 M $NaHCO_3$, 0.5 M NaCl (pH 8) buffer, then 0.5 M $CH_3COONa$ (pH 4) buffer and finally PBS at pH 7.5. M1 cells were plated at a density of $0.5 \times 10^6$ cells per well (6 well plate) in 10% FBS DMEM medium until 70–80% confluence. Prior to incubation with peptides, cultures were changed to serum-free DMEM medium, then evenly overlaid with 50 µg bead conjugated peptides, and incubated for the indicated period. Soluble peptides were added overnight to M1 cells at a concentration of 50 µg/ml.

Figure 6:
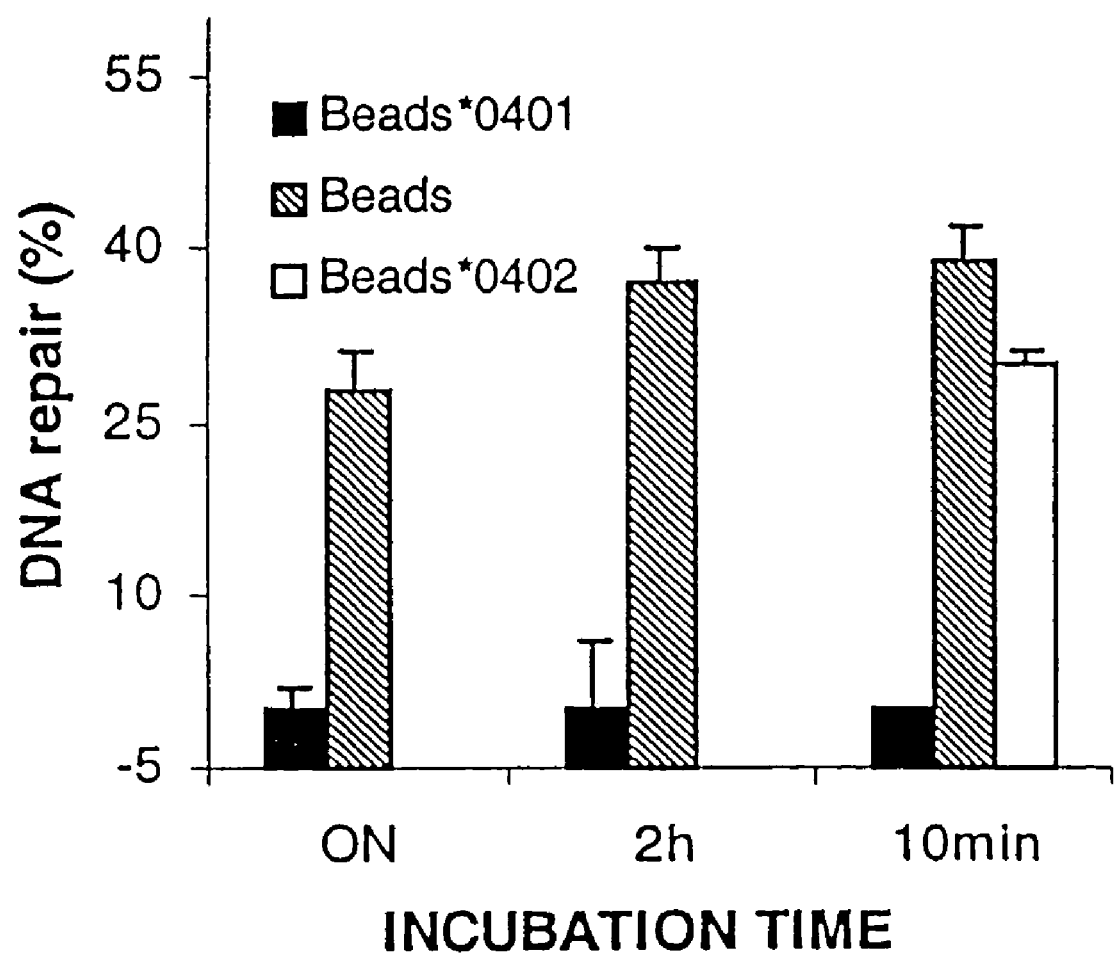
FIG. 6 is a bar graph which depicts the experimental results demonstrating the inhibition of cAMP-mediated inducible DNA repair by SE-containing peptide-conjugated beads.

M1 cells were preincubated for various times with bare Sepharose beads (Beads) or peptide-conjugated beads before 2CA-induced DNA repair assays were performed. As shown in FIG. 6, the conjugated peptide corresponding to residues 65–78 of the DRβ*0401 [SEQ ID NO: 6] protein, but not a peptide corresponding to the equivalent region on DRβ*0402 [SEQ ID NO: 8], blocked cAMP-mediated DNA repair. Complete inhibition could be seen as early as 10 minutes following incubation of human fibroblastoid cells with peptide-coated beads.

EXAMPLE 4

This example demonstrates that the SE is found in AD-modulating proteins, and that the SE in these proteins can inhibit cAMP-mediated DNA repair.

The amino acid sequence of the SE, QRRAA [Gln Arg Arg Ala Ala] [SEQ ID NO: 2], was subjected to a BLAST search against the SwissProt database (84,482 sequences). Only four non-MHC human proteins were found to contain that sequence. Strikingly, three of the four were nervous system proteins (APLP1, laminin β2 and ankyrin B). A homologous sequence was found around the variable position 158 of ApoE (FIG. 7). As shown in FIG. 7, amino acids 70–74 of HLA-DRβ*0401 and HLA-DRβ*0404 correspond to the SE. Amino acids 70–74 of HLA-DRβ*0402 and HLA-DRβ*0403 encode sequences which do not correspond to the SE or SE motif. Amino acids 118–122 of human laminin β2 also correspond to the SE sequence, as do amino acids 387–391 of APLP1. Amino acids 121–125 of murine laminin β2 are consistent with the SE motif. Similarly, amino acids 156–160 of ApoE ε4, ε3 and ε2 are consistent with the SE motif (FIG. 7).

Figure 8:
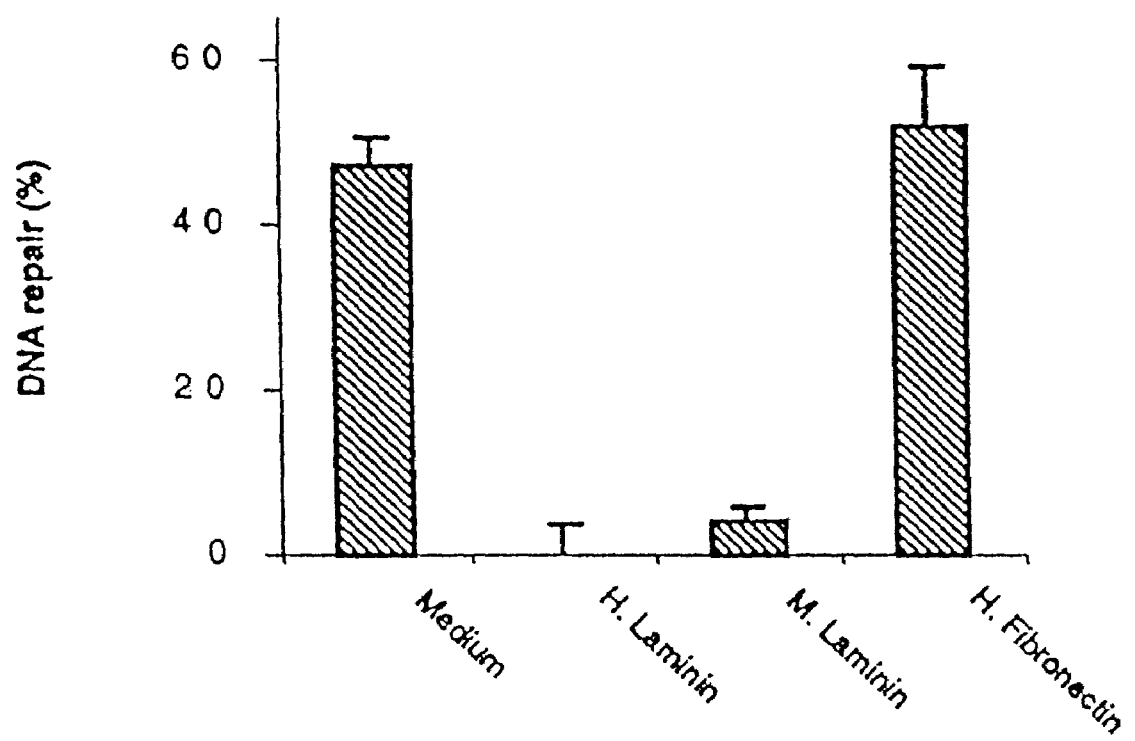
FIG. 8 is a bar graph which depicts the inhibition of cAMP-dependent DNA repair by SE-containing, non DR.beta. proteins.

The QRRAA [Gln Arg Arg Ala Ala] [SEQ ID NO: 2] sequence in human laminin appears to be functional, as exposure of M1 cells to purified human and mouse laminin inhibited their inducible DNA repair activity. 2CA-induced DNA repair was determined in M1 cells preincubated overnight in tissue culture plates coated with either human laminin (H. Laminin), mouse laminin (M. Laminin), or human fibronectin (H. Fibronectin). Fibronectin, on the other hand, did not cause any inhibition (FIG. 8).

Figure 9:
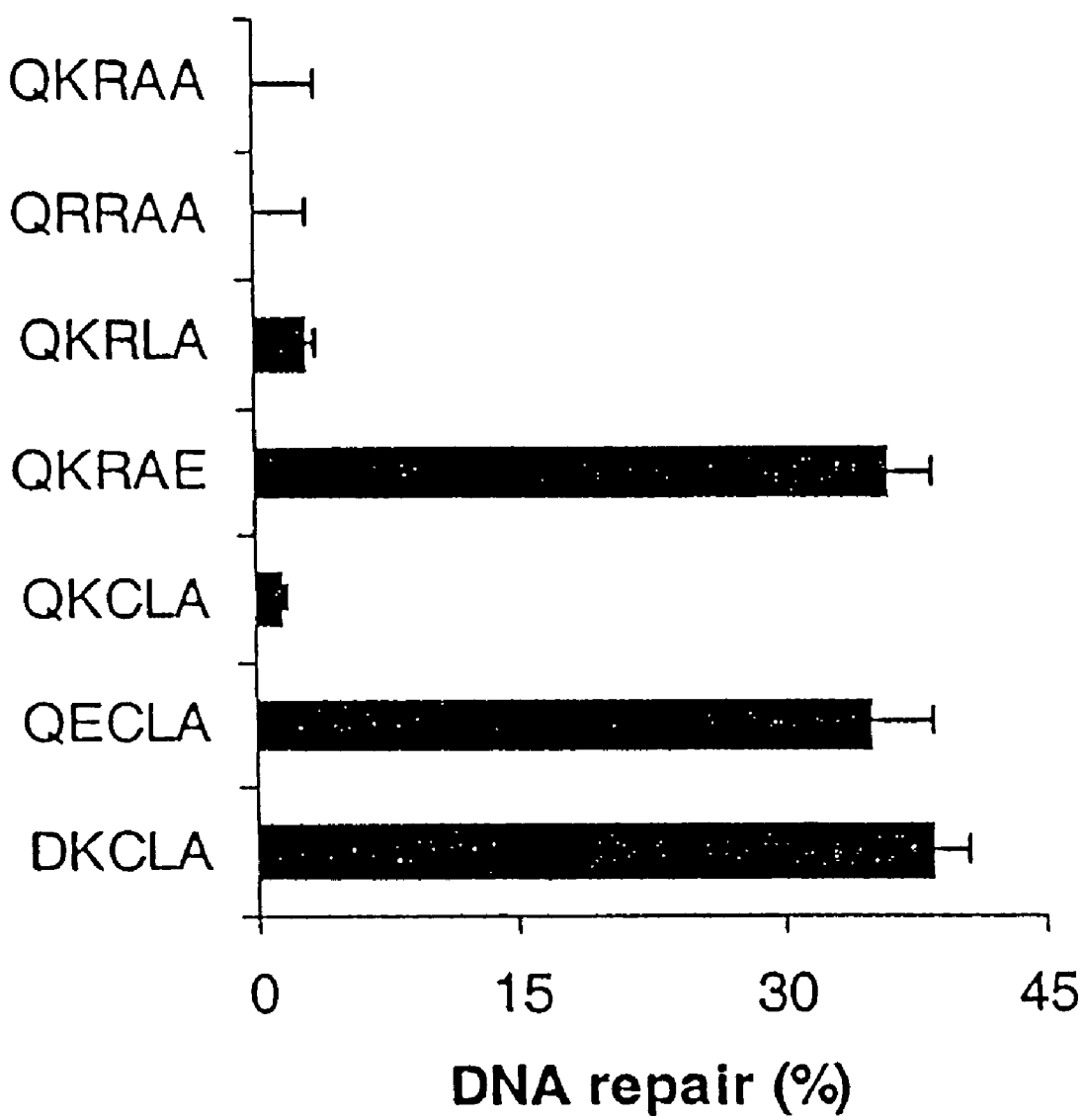
FIG. 9 is a bar graph which depicts the results of experiments carried out to determine the SE motif.

To directly examine the biological activity of the shared epitope, a QRRAA [Gln Arg Arg Ala Ala] pentapeptide [SEQ ID NO: 2] was synthesized and used in DNA repair assays. 2CA-induced DNA repair was determined in M1 cells preincubated overnight with 50 µg/ml of synthetic pentapeptides representing the SE, or its single- or multiple-amino acid substitutions. As can be seen in FIG. 9, preincubation of M1 cells with the short peptide inhibited completely cAMP-dependent DNA repair induction. The homologous pentapeptide QKRAA [Gln Lys Arg Ala Ala] [SEQ ID NO: 1] had a similar effect.

To further determine the critical amino acids involved, a series of synthetic pentapeptides carrying single or multiple amino acid substitutions were tested. The sequences of the pentapeptides are shown in Table 4.

TABLE 4

Synthetic Pentapeptides

| Pentapeptide Sequence | SEQ ID NO |
|---|---|
| QKRAA<br>Gln Lys Arg Ala Ala | SEQ ID NO: 1 |
| QRRAA<br>Gln Arg Arg Ala Ala | SEQ ID NO: 2 |
| QKRLA<br>Gln Lys Arg Leu Ala | SEQ ID NO: 11 |
| QKRAE<br>Gln Lys Arg Ala Glu | SEQ ID NO: 14 |
| QKCLA<br>Gln Lys Cys Leu Ala | SEQ ID NO: 12 |
| QECLA<br>Gln Glu Cys Leu Ala | SEQ ID NO: 15 |
| DKCLA<br>Asp Lys Cys Leu Ala | SEQ ID NO: 16 |

As can be seen in FIG. 9, substitution of either glutamine 70 with aspartic acid, arginine/lysine 71 with glutamic acid, or alanine 74 with glutamic acid, abolished in all cases the inhibitory effect on cAMP-dependent signaling. On the other hand, substitution of arginine 72 to cysteine, or alanine 73 to leucine had no effect on the inhibitory effect of the peptide. It is therefore concluded that, consistent with the data shown in FIG. 1, residues Q70 [Gln70], R/K71 [Arg/Lys71] and A74 [Ala74] are critical amino acids, while R72 [Arg72] and A73 [Ala73] are not. These findings indicate that cAMP signal-inhibiting sequences possess the Q-(K/R)-X-X-A [Gln (Lys/Arg) Xaa Xaa Ala (wherein Xaa represents any amino acid)] [SEQ ID NO: 3] motif. That motif exists in RA SE, as well as in APLP1, laminin β2 and ApoE.

It is noteworthy that the ApoE2-derived peptide, QKCLA [Gln Lys Cys Leu Ala] [SEQ ID NO: 12], and the ApoE3/ApoE4-derived peptide, QKRLA [Gln Lys Arg Leu Ala] [SEQ ID NO: 11], were equally effective in suppressing cAMP signaling. However, only ApoE2 and ApoE3, but not ApoE4 are believed to have a neuroprotective effect in-vivo. It is hypothesized that the failure of the ApoE4 protein to trigger neuroprotective signaling in-vivo may be due to the C112R [Cys112Arg] substitution [the single substitution which truly distinguishes between the AD-enhancing (ApoE4 with R112) and AD-protecting (ApoE2 and ApoE3 with C112) alleles]. The 156–160 domain of ApoE4 may be inaccessible to interaction with its receptor due to conformational constraints imposed by the arginine residue at position 112. A positively charged residue at this position has been previously shown to affect the secondary structure and binding properties of ApoE [Weisgraber K H. *J Lipid Res* 31:1503–1511 (1990); LaDue M J et al. *J Neurosci Res* 49:1 9–18 (1997)].

EXAMPLE 5

In this example, results of experiments carried out to address the potential pathway by which the SE motif may inhibit cAMP signaling are presented. The SE motif may inhibit cAMP signaling through the NO pathway, although the precise mechanism underlying the invention is not essential to the practice of the invention, and any hypothesized mechanism is not intended to be in any way limiting.

As mentioned above, DNA repair signaling is mediated by the cAMP/PKA pathway and is inhibited by NO. Because NO has neuroprotective effects and elevating NO levels has been identified as a desirable therapeutic objective in AD, the inventors studied the signaling events caused by SE peptides.

A. cAMP levels were assayed in M1 cells that were preincubated for 10 minutes with peptide-conjugated beads [Bead*0401, SEQ ID NO:6; Bead*0402, SEQ ID NO: 8], and intracellular cAMP level changes in response to stimulation with either 10 μM (FIG. 10A, top) or 100 μM (FIG. 10A, bottom) of 2CA were determined at different time points. cAMP levels were measured using a commercial enzyme immunoassay kit from Pharmacia. Results are expressed as fold increase of cAMP above baseline levels.

B. PKA activity was determined in M1 cells preincubated with peptide-conjugated beads [Bead*0401, SEQ ID NO: 6; Bead*0402, SEQ ID NO: 8], at different time points following treatment with 10μM 2CA as above.

C. NO levels were determined as described above using a commercial kit (from Cayman) in M1 cells at different time points following exposure to peptide-conjugated Sepharose beads [Bead*0401, SEQ ID NO: 6; Bead*0402, SEQ ID NO: 8].

D. cGMP levels in M1 cells were determined as described above using an enzyme immunoassay kit (Pharmacia) at different time points following exposure to 50 μg/ml of soluble 65–78*0401 [SEQ ID NO: 6] or 65–78*0402 [SEQ ID NO: 8] peptides.

Figure 10:
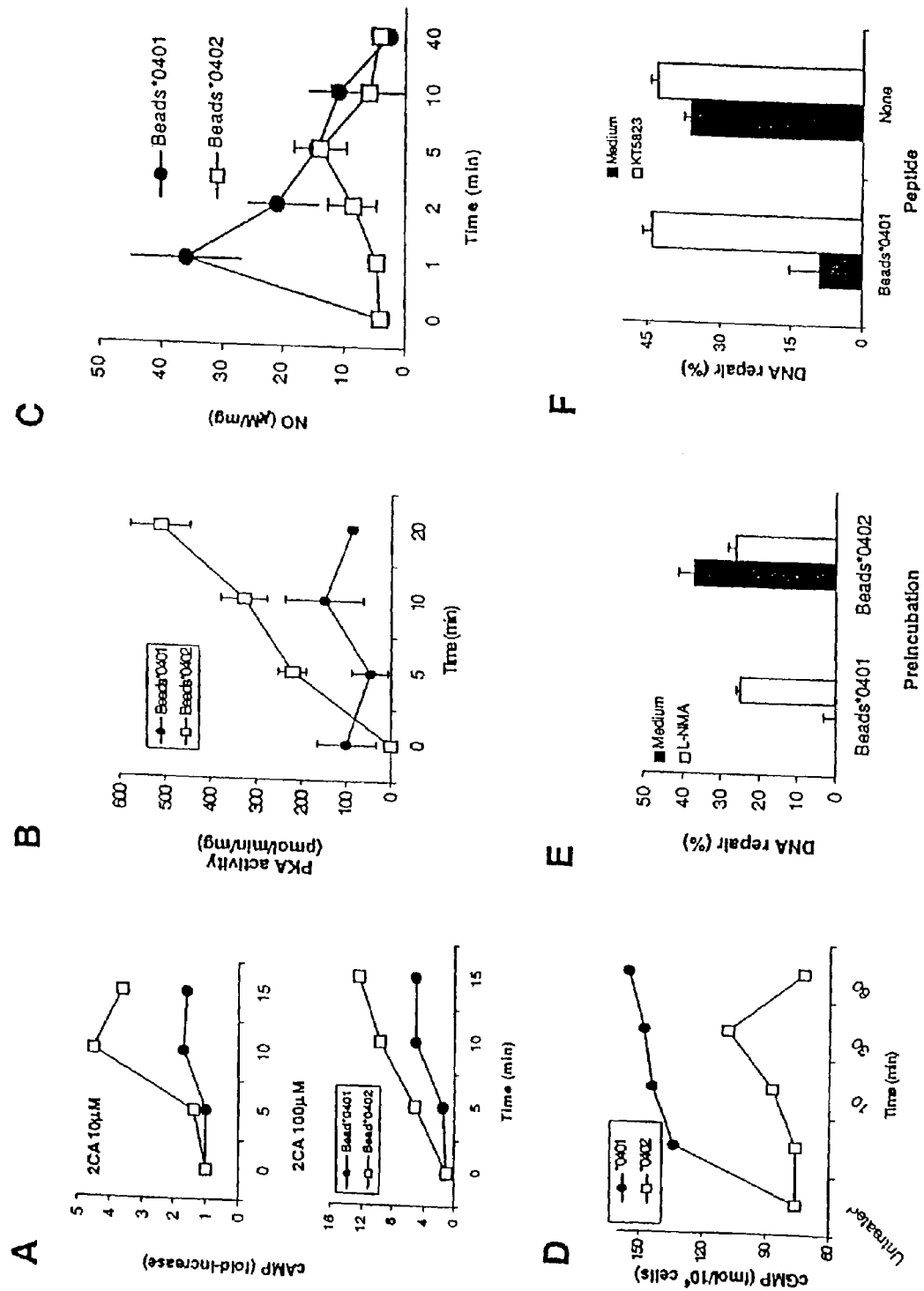
FIG. 10 presents a characterization of SE-triggered intracellular signaling.
Figure 11B:
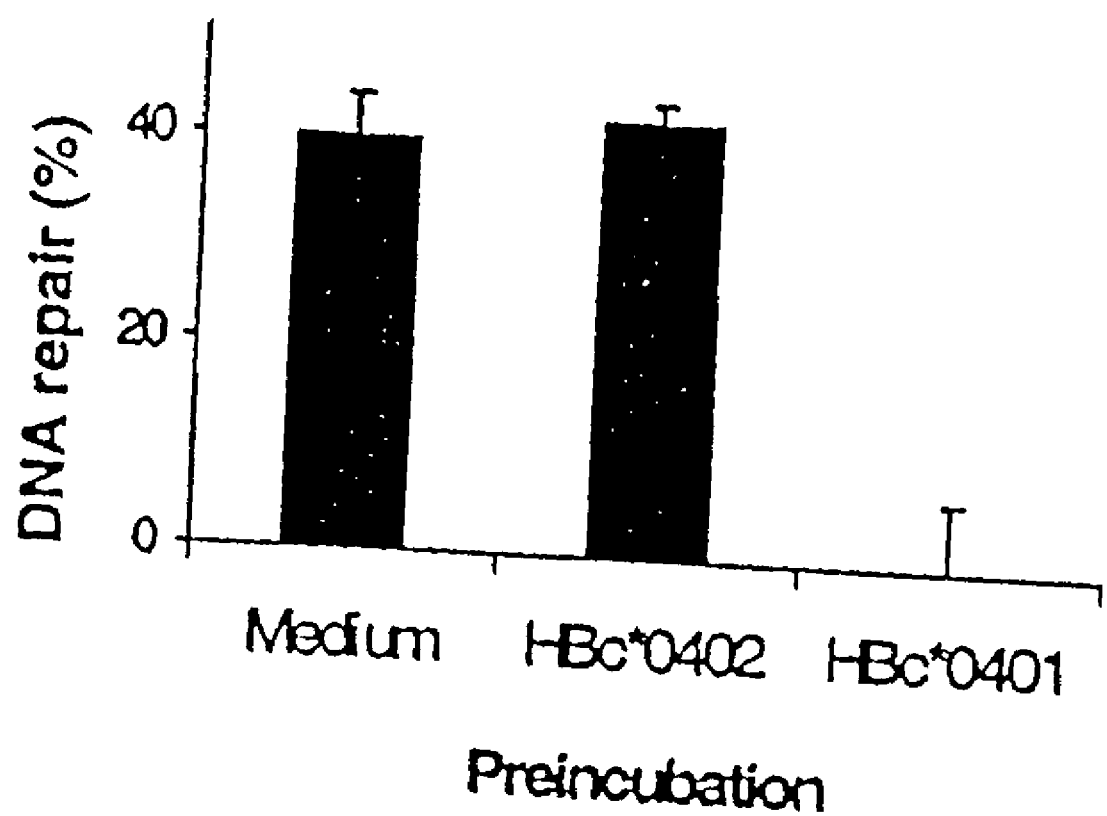
FIG. 11 shows the inhibition of cAMP signaling by SE genetically inserted into foreign proteins.
FIG. 11A shows the amino acid sequence of the recombinant HBc proteins contain number of alterations in such peptides. In some embodiments, the derivatives comprise peptides with amino acid sequence changes. Such changes can be conservative amino acid substitutions, amino acid deletions or amino acid insertions, provided that the SE or SE motif activity is substantially (50% or greater) retained. Analogues have amino acid analogues in place of the corresponding natural amino acids. Examples of such analogues include (but are not limited to) p-fluorophenylalanine (an analogue of phenylalanine) and ethionine and norleucine. Analogues also include incorporation of D-amino acids at particular points along the peptide chain. Derivatives and analogues may be conjugated (see below).

As shown in FIG. 10, M1 cells incubated with peptides [SEQ ID NO: 6] which contain QKRAA [Gln Lys Arg Ala Ala] [SEQ ID NO:1] failed to increase cAMP levels or activate PKA following stimulation with 2CA, while cells incubated with a control peptide [SEQ ID NO: 8] mounted substantial response to the agonist (FIGS. 10A and B).

E. M1 cells were preincubated overnight with 5 mM of the nitric oxide synthase (NOS) inhibitor, $N^G$-methyl-L-arginine (L-NMA). At the end of incubation, cells were collected, washed and preincubated for 10 min with peptide-conjugated beads [Bead*0401, SEQ ID NO: 6; Bead*0402, SEQ ID NO: 8], before determining 2CA-inducible DNA repair activity.

F. M1 cells were preincubated for 10 min with 1 μM of the protein kinase G (PKG) inhibitor, KT5823. At the end of incubation, cells were collected, washed and preincubated with either medium or 65–78*0401 [SEQ ID NO:6] peptide-conjugated beads. Cells were then collected, washed and subjected to 2CA-induced DNA repair assay.

As shown in FIG. 10(E), the inhibitory effect of the peptide [SEQ ID NO: 6] which contains QKRAA [Gln Lys Arg Ala Ala] [SEQ ID NO: 1] could be blocked by prior incubation of cells with a NOS inhibitor, $N^G$-methyl-L-arginine (L-NMA). Additionally, incubation of M1 cells with the SE-containing peptide triggered increased cGMP levels in those cells (FIG. 10D). The inhibitory effect of SE-containing peptides could be blocked by prior incubation of M1 cells with the PKG inhibitor, KT5823 (FIG. 10F).

Taken together, these data suggest that the mechanism by which SE-containing peptides modulate cAMP-dependent signaling involve receptor-mediated activation of NOS with resultant increased levels of NO, which, in turn cause increased cGMP, culminating in PKG activation (FIG. 10).

EXAMPLE 6

In this example, results of experiments carried out to address the cAMP signaling effects of genetically-engineered SE-containing proteins are presented.

To further assess the ability of SE-containing compounds to reverse cAMP signaling and to assess the potential utility of delivery systems for such epitopes, a genetic approach was used. To that end, the SE was inserted into a recombinant hepatitis B core (HBc) protein, which assembles a multimer of 180–240 subunit shell of approximately 30–34 nm in diameter with 90–120 spikes. That system has been previously shown to be an efficient, non-replicative and non-infective carrier of foreign epitopes [Reviewed in Pumpens P and Grens E. *FEBS Lett* 442:1–6 (1999)]. Accordingly, oligonucleotides corresponding to the region surrounding the third allelic hypervariable region (residue 65–79 of the DRβ chain) of either the SE-containing, DRB1*0401, or the SE-negative, DRB1*0402, alleles were expressed at the tips of the HBc spikes (HBc*0401 (SEQ ID NO: 17) and HBc*0402 (SEQ ID NO: 18), respectively, FIG. 11A).

The appropriate coding sequence was inserted as a synthetic oligonucleotide between two unique restriction sites between amino acid residues 78 and 79 of the HBc molecule, as described in Borisova et al. [Biol Chem 380: 315–324 (1999)]. Due to the necessity to introduce neighboring restriction sites, the oligonucleotides coded for additional amino acid residues located amino- and carboxy-terminally to the SE (His, and Val and Asp, respectively). The nucleotide sequence for amino acids 65–79 derived from DRB*0401 along with the amino-terminal flanking His and the carboxy-terminal flanking Val and Asp is:

cac aag gac ctc ctg gag cag aag cgg gcc gcg gtg gac acc tac tgc gta gat [SEQ ID NO: 19]

and the nucleotide sequence for amino acids 65–79 derived from DRB*0402 along with the amino-terminal flanking His and carboxy-terminal flanking Val and Asp is:

cac aag gac atc ctg gaa gac gag cgg gcc gcg gtg gac acc tac tgc gta gat [SEQ ID NO: 20].

M1 cells were preincubated overnight with 50 μg/ml of HBc*0401 or HBc*0402. At the end of incubation, cells were collected, washed and subjected to 2CA-induced DNA repair assay as above. As shown in FIG. 11B, SE-expressing core particles, but not those expressing a non-SE-containing sequence, effectively suppressed cAMP signaling. Thus, the SE, when engineered into carrier proteins can specifically transduce a cAMP-inhibitory signal, similar to SE-containing native proteins, or short synthetic peptides. This finding suggests that a gene transfer for targeted delivery of the SE might prove useful in therapies.

EXAMPLE 7

This example presents the results of experiments carried out to address the neuroprotective effects of SE-containing peptides.

In order to assess whether SE-containing peptides exert a neuroprotective effect, preliminary experiments were carried out with the hybrid neuroblastoma-glioma NG108-15 cell line. Cells ($10^5$/ml) were first cultured overnight at near-confluence in 24-well plates in DMEM medium supplemented with 1% fetal calf serum (FCS). Under these conditions, NG108-15 cells show a flat, multipolar morphology and neurite formation (129). After 20 hours, cells were stressed acutely in serum-free medium (by aspiration of the medium and replacement with serum-free DMEM) with 50 μg/ml of peptides and evaluated morphologically at different time points thereafter. In cultures treated with the control peptide 65–78*0402 [SEQ ID NO: 8], adjacent cells showed a rounding effect and collapsed into aggregates (FIG. 12A). In cultures treated with the SE-containing peptide 65–78*0401 [SEQ ID NO: 6], there was greater preservation of the multipolar flat cell morphology with neurites (FIG. 12B). Morphological differences between cultures treated with different peptides could be observed as early as 5–6 hrs after treatment. The photographs shown were taken at the 24 hr time point. In another experiment (FIG. 12C), NG108-15 cells were cultured at low cell density ($2\times10^4$/ml) in 1% FCS-containing DMEM medium overnight. The next day cells were subjected to acute stress in serum-free and low glucose (RPMI1640) medium (after aspiration of the 1% FCS DMEM) in the presence of 50 μg/ml of either 65–78*0401 [SEQ ID NO: 6] or 65–78*0402 [SEQ ID NO: 8] peptides. After 72 hours, cells were fixed with 1% formaldehyde and inspected microscopically. Mean ±SEM was determined by averaging cell counts in eight randomly-selected microscopic fields in 200× magnification. Neurite-positive cells were defined as cells with one or more projections extending at least twice as long as the cell diameter. Cells cultured in the presence of SE-containing peptide 65–78*0401 [SEQ ID NO: 6] showed a significantly higher survival rate ($p<0.0005$) and a higher percentage of neurite-positive cells ($p<0.001$), compared to cells cultured in the presence of the control peptide, 65–78*0402 [SEQ ID NO: 8] (FIG. 12C). The calculated number of neurite-positive cells was over 6-fold higher in SE-containing peptide-cultured cells. When cultured in the presence of lysophosphatidic acid or high concentrations of serum, neuronal cells undergo neurite retraction (130). Treating NG108-15 cells with the SE-containing, 65–78*0401 [SEQ ID NO: 6] peptide, but not with the control 65–78*0402 [SEQ ID NO: 8] peptide, inhibited the neurite retraction effect of 10% FCS (data not shown). Thus, it is concluded that SE-containing peptides may exert neuroprotective effects.

The data presented here indicate that the RA SE represents a sequence motif found in proteins capable of transmembrane activation of the NO/cGMP/PKG pathway. It is proposed that the SE motif is playing a role in the neuroprotective effects of ApoE, APLP1 and laminin and could account for the negative association between AD and RA. Of course, understanding the mechanism underlying the invention is not required for the successful practice of the invention, and the invention is in no way limited to any particular mechanism.

EXAMPLE 8

This example outlines various animal models and assays that may be used to evaluate the biological activity of the compounds of the present invention in vivo.

A. Transgenic Mice Models

Transgenic (Tg) mice over expressing wild type or mutant APP manifest age-dependent neuropathology reminiscent of AD, including amyloid plaques, hyperphosphorylated tau, cognitive deficits and behavioral abnormalities. There are several such Tg lines, which differ in the type of mutant APP, the promoter used for targeted expression, the background strain of mice and the level of APP overexpression achieved.

The resemblance to the human disease is substantial, though incomplete, since no neurofibrillary tangles or neuronal loss can be seen.

Double Tg mice expressing APP and mutant presenilin have been described. Those mice demonstrate AD-like neuropathology at an earlier age compared to most single Tg mice.

Other Tg models involve the ApoE4 or tau genes. Those models are characterized by psychometric impairment with axonopathy in the brain and spinal cord. Although hyperphosphorylated tau is present, neurofibrillary tangles are absent. Double Tg mice expressing tau and mutant APP show earlier and more severe neuropathology.

ApoE-deficient mice manifest mild cognitive impairment and tau hyperphosphorylation. Tg mice over expressing ApoE4 in neurons manifest a severe neuropathologic phenotype, which included motor problems, muscle wasting, hyperphosphorylated tau and early death. The pathology is evident as early as three months after birth.

B. Induced Models of AD-like Pathology in Rodents.

Cholinotoxicity in rats is considered an acceptable model for Alzheimer's-associated dementia. The underlying rationale for studying this model is that an intact cholinergic system is required for normal brain functions. That system is defective in AD. To induce cholinotoxicity, male Wistar rats are injected intracerebrally with the cholinotoxin, ethylcholin aziridium (AF64A), which is a blocker of choline uptake. Short-term memory is significantly impaired in those animals.

Another model of induced dementia in rats involves induction of bilateral electrocortical lesions of nucleus basalis manocellularis. Those lesions produce deficiency in several behavioral AD-related tests, such as active avoidance, neophobia, aggression and depression.

Amyloid plaque deposition can be induced in mammals by infusing into the brain parenchyma an amyloid peptide at a basic pH as described in U.S. Pat. No. 6,172,277 to Tate et al., herein incorporated by reference.

C. Aged Animals

AD-like neuropathology has been reported in aged dogs and monkeys. Old canines develop extensive β amyloid deposition within neurons and synapses, with formation of senile plaques. Neurofibrillary tangles, however, are not seen. The age-associated histopathology in canine is accompanied by cognitive decline. Aged rhesus monkeys show β amyloid deposition in senile plaques. Microinjection of fibrillar β amyloid into the aged- but not young-rhesus monkey cerebral cortex results in profound neuronal loss, tau phosphorylation and microglial proliferation.

D. Biological Tests in vivo.

Tg mice and aged dogs and monkeys are treated with one of the compounds of the invention (e.g. SE- or SE motif-containing peptides, derivatives, analogues, mimetics, conjugates or antagonists) by any convenient route of administration (e.g. intravenously, subcutaneously, intraperitoneally or intramuscularly). Alternatively, the compounds are administered intranasally or as an inhaled aerosol. At different time points thereafter, animals are subjected to behavioral studies, which in mice include open field testing, beam task, string task, Y-maze, water maze, circular platform task, as well as passive and active avoidance. Aged dogs are evaluated for cognitive function and exploratory behavior. Monkeys are tested for memory tasks.

Histological parameters of neurodegeneration are determined in sacrificed mice and rats at different time points after treatment. Brain tissue is tested for glial fibrillary acidic protein, activated microglia, dystrophic neurites, amyloid plaques and detergent-insoluble and water soluble amyloid β protein. Brain sections and tissue extracts from different anatomical areas are used to determine the extent of ApoE expression and tau phosphorylation by immunohistochemistry and Western blotting, using specific monoclonal antibodies.

For cholinotoxin-induced cognitive impairments, male Wistar rats are injected intracerbroventricularly (ICV) with AF64A as described by Fisher et al. [*Neurosci Lett* 102: 325–331 (1989)]. Animals are left to recover for a week. Learning and memory tests are conducted using the swim maze test. Subgroups of animals are injected ICV daily with any of the compounds of the present invention (e.g. SE- or SE motif-containing peptides, analogues, derivatives, mimetics or antagonists), or with saline as a control. Learning and memory tests are repeated 7 and 14 days later.

E. Biological Tests in vitro.

Survival of neurons is determined in vitro by culturing neuronal cells as described by Forsythe and Westbrook [*J Physiol* (Lond) 396:515–533 (1988)]. Alternatively, neuroblastoma cell lines are used. After established growth is observed, the cultures are given a change of medium and treated with different concentrations of the compounds of the invention (e.g. SE- or SE motif-containing peptides, derivatives, analogues, mimetics and antagonists). Neuronal survival is determined by microscopic determination of viable cell number per field. The extent of neurite formation in neuroblastoma cell lines is determined by counting the number of cells with neurites extending to a length greater than twice the cell diameter.

EXAMPLE 9

In this example, the preparation of a peptide conjugate is described. The synthetic peptide $NH_2$-Q(K/R/H)XXA [Gln (Lys/Arg/His Xaa Xaa Ala] [SEQ ID NO: 21]can be prepared commercially (e.g. Multiple Peptide Systems, San Diego, Calif.). In a preferred embodiment, a cysteine is added (e.g. QRACA [Gln Arg Ala Cys Ala] [SEQ ID NO: 22], QKRAAC [Gln Lys Arg Ala Ala Cys] [SEQ ID NO: 23] or CQKRAA [Cys Gln Lys Arg Ala Ala] [SEQ ID NO: 24]) to facilitate conjugation to other proteins.

In order to prepare the carrier protein for conjugation (e.g. BSA), it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM $NaPO_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

EXAMPLE 10

In this example, several peptides based on the SE motif are contemplated.

The SE motif, Q(K/R)XXA [Gln (Lys/Arg) Xaa Xaa Ala] [SEQ ID NO: 3], has two variable amino acid positions (Xaa, wherein Xaa represents any amino acid). Thus, a variety of peptide sequences are possible, based on variation at the variable positions. As noted above, a derivative of the SE motif, in which histidine is substituted for the lysine or arginine is also contemplated (i.e. QHXXA [Gln His Xaa Xaa Ala] [SEQ ID NO: 4]). Thus, possible SE motif-containing peptides and derivatives can be expressed by the following sequences: $QRX_1X_2A$ [Gln Arg $Xaa_1$ $Xaa_2$ Ala] [SEQ ID NO: 25], $QKX_1X_2A$ [Gln Lys $Xaa_1$ $Xaa_2$ Ala] [SEQ ID NO: 26] and $QHX_1X_2A$ [Gln His $Xaa_1$ $Xaa_2$ Ala] [SEQ ID NO: 27] in which $X_1$ is selected from the group of amino acids consisting of alanine, valine, leucine, isoleucine, serine, threonine and asparagine; and $X_2$ is selected from the group of amino acids consisting of alanine, valine, isoleucine, serine, threonine and asparagine.

EXAMPLE 11

In this example calreticulin is identified as a receptor which binds SE-containing peptides.

Total cellular protein extracts were loaded onto columns of Sepharose beads, conjugated with either SE-containing peptide 65–78*0404 [SEQ ID NO: 28] or the control peptide 65–78*0402 [SEQ ID NO: 8]. Bound proteins were eluted at low pH. See, Auger I, Escola J M, Gorvel J P and Roudier J. HLA-DR4 and HLA-DR10 motifs that carry susceptibility to rheumatoid arthritis bind 70-kD heat shock protein. *Nat Med* 2:306–310, 1996. While no protein binding was detected on the 65–79*0402 [SEQ ID NO: 7]-conjugated control column, 65–78*0404 [SEQ ID NO: 28]-conjugated column eluates gave ~20 distinct bands corresponded to known proteins. 11 sequenced bands matched intracellular proteins, and only two sequences matched previously identified cell surface proteins: heat shock protein 60 (HSP60) and calreticulin. Both calreticulin and HSP60 are chaperones, with strong tendency to form hetero-complexes.

Figure 13A:
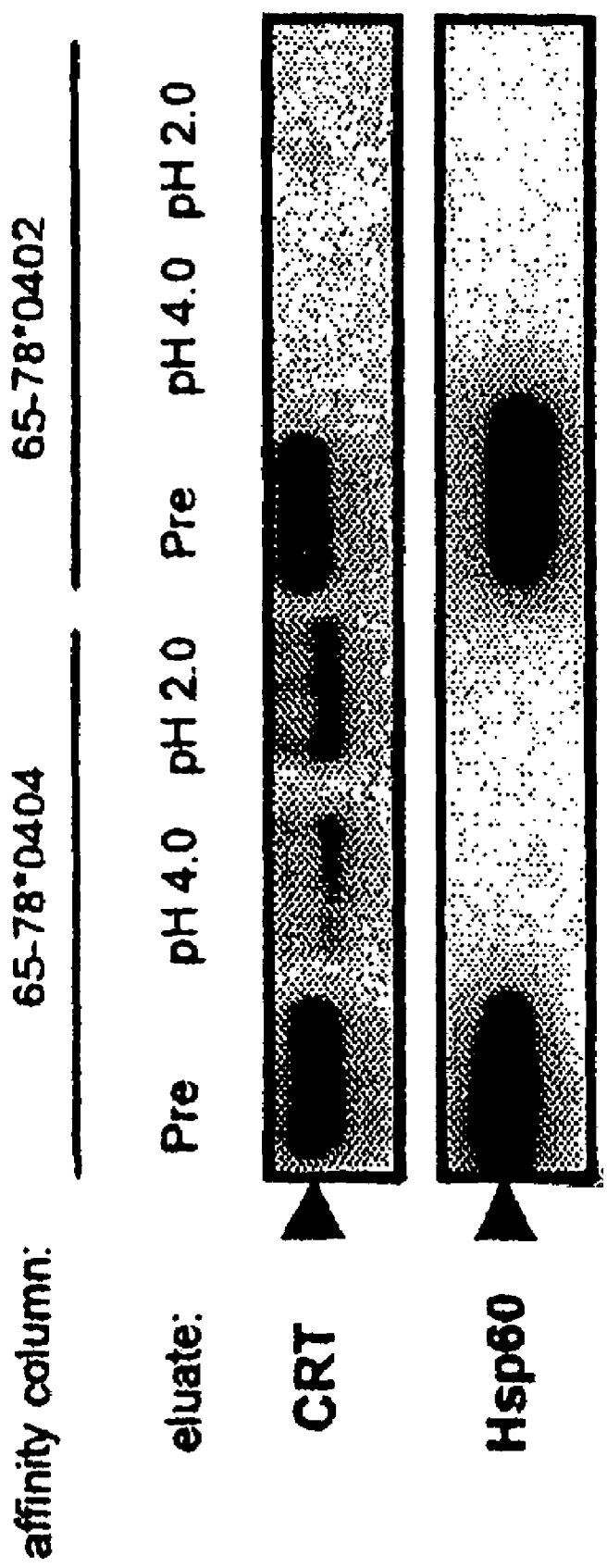
Figure 13B:
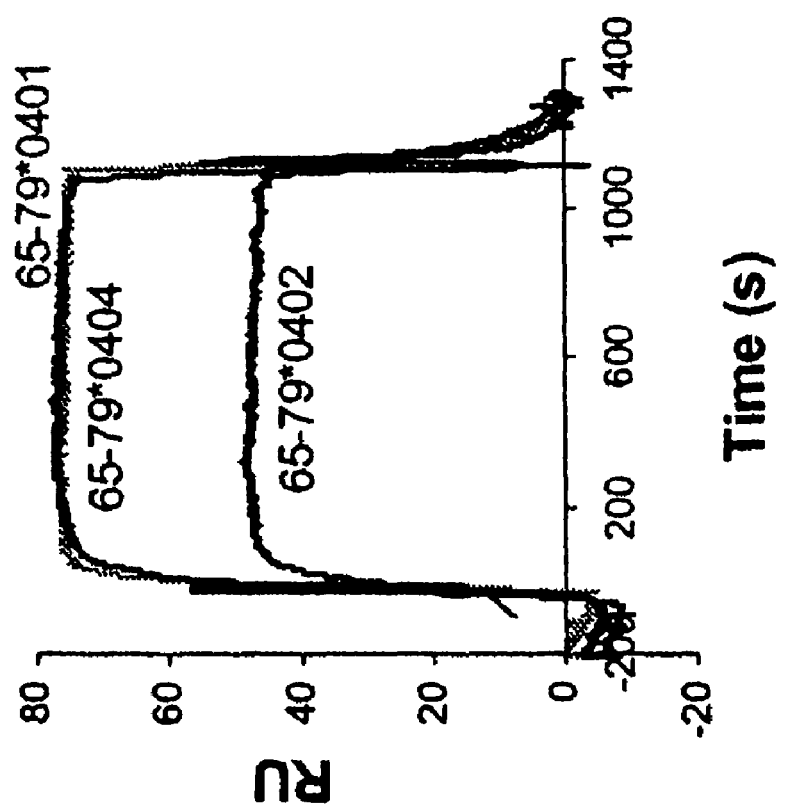

To determine whether 65–78*0404 [SEQ ID NO: 28]-conjugated peptides bind these proteins directly, purified recombinant products were used. As can be seen in FIG. 13A, 65–78*040-affinity columns specifically bound recombinant human calreticulin (the amino acid sequence of this recombinantly produced protein is set out in FIG. 14 [SEQ ID NO: 29]), but not HSP60. These data confirm that cell surface calreticulin is binding SE-containing peptides. That conclusion was supported in surface plasmon resonance experiments shown in FIG. 13B. SE-containing peptides, 65–79*0401-[SEQ ID NO: 5] and 65–79*0404-[SEQ ID NO: 10], as well as a control peptide 65–79*0402-[SEQ ID NO: 7] were immobilized on different channels in a Biacore® sensor chip CM5 and purified recombinant calreticulin was applied in the flow phase. As can be seen in FIG. 13B, SE-containing 65–79*0401-[SEQ ID NO: 5] and 65–79*0404-[SEQ ID NO: 10] showed markedly higher calreticulin binding, compared to the control peptide, 65–79*0402-[SEQ ID NO: 7].

Figure 13C:
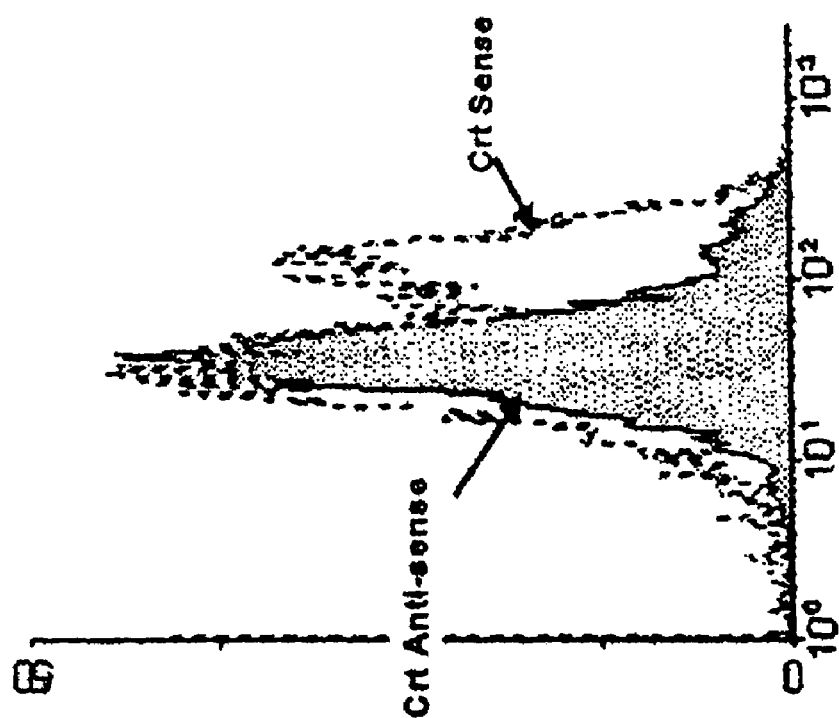
Figure 13D:
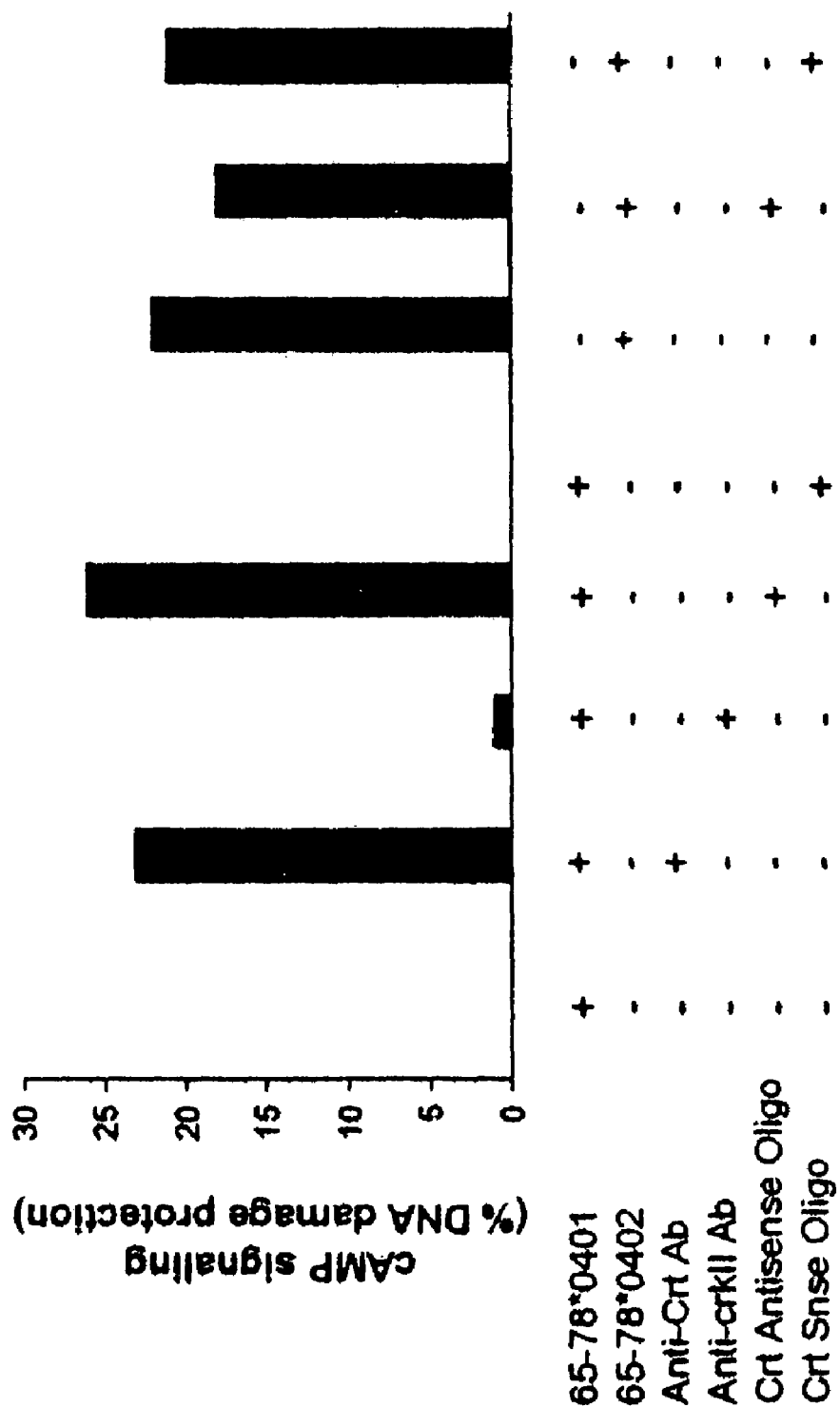

Finally, in order to determine whether these neuroprotective peptides transduce their signaling through calreticulin, two complementing protocols were executed: i) Inhibition of peptide-calreticulin interaction using anti-calreticulin antibodies, or ii) blocking calreticulin expression with antisense oligonucleotides (as shown in FIGS. 13C and 13D). As can be seen in FIG. 13C, calreticulin antisense (but not sense) oligonucleotides inhibited cell surface expression and blocked peptide-triggered signaling as shown in FIG. 13D. Similarly, as shown in FIG. 13D, anti-calreticulin antibodies specifically blocked the peptide effect. These data are support the conclusion that calreticulin is the cell surface receptor which mediates SE-peptide signaling.

---

The invention claimed is:

1. A composition comprising a synthetic shared epitope peptide, said peptide consisting of the sequence DKCLA (Asp Lys Cys Leu Ala) (SEQ ID NO: 16).

2. The peptide of claim 1, wherein said peptide is conjugated to at least one lipophilic moiety.

3. The peptide of claim 2, wherein said lipophilic moiety is a moiety in the form of a saturated or unsaturated radical.

4. The peptide of claim 3, wherein said moiety comprises a hydrocarbyl or carboxylic acyl having at least 5 carbon atoms.

5. The peptide of claim 3, wherein said lipophilic moiety is conjugated at the carboxy terminus of said peptide.

6. The peptide of claim 1, wherein said peptide is amidated at the carboxy terminus of said peptide.

7. The peptide of claim 3, wherein said lipophilic moiety is conjugated at the amino terminus of said peptide.

8. The peptide of claim 1, wherein said peptide is acetylated at the amino terminus of said peptide.

9. The peptide of claim 1, wherein said lipophilic moiety is conjugated to both the amino terminus and carboxy terminus of said peptide.

10. A composition comprising:
   a synthetic peptide consisting of the sequence DKCLA (Asp Lys Cys Leu Ala) (SEQ ID NO: 16),
   a) an aqueous medium; and
   b) at least one compound selected from the group comprising a buffer, a preservative and a salt.

11. The composition of claim 10, wherein said preservative is an antimicrobial preservative.

12. The composition of claim 10, wherein said synthetic peptide is present at 1–1000 micrograms.

13. A synthetic peptide consisting of the sequence DKCLA (Asp Lys Cys Leu Ala) (SEQ ID NO: 16).

14. The synthetic peptide of claim 13, wherein said peptide is conjugated to at least one moiety.

* * * * *

SEQUENCE LISTING

<160> NUMBER OF SEQ ID NOS: 36

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Gln Lys Arg Ala Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Gln Arg Arg Ala Ala
1               5

```
<210> SEQ ID NO 3
<211> LENGTH: 5
<212> TYPE: PRT
<213> ORGANISM: Escherichia coli
<220> FEATURE:
<221> NAME/KEY: MISC_FEATURE
<222> LOCATION: (2)..(2)
<223> OTHER INFORMATION: The residue at this position can be lysine or
      arginine.
<220> FEATURE:
<221> NAME/KEY: MISC_FEATURE
<222> LOCATION: (3)..(4)
<223> OTHER INFORMATION: The residues at these positions can be any
      amino acid.

<400> SEQUENCE: 3

Gln Xaa Xaa Xaa Ala
1               5

<210> SEQ ID NO 4
<211> LENGTH: 5
<212> TYPE: PRT
<213> ORGANISM: Escherichia coli
<220> FEATURE:
<221> NAME/KEY: MISC_FEATURE
<222> LOCATION: (3)..(4)
<223> OTHER INFORMATION: The residues at these positions can be any
      amino acid.

<400> SEQUENCE: 4

Gln His Xaa Xaa Ala
1               5

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Lys Asp Leu Leu Glu Gln Lys Arg Ala Ala Val Asp Thr Tyr Cys
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Lys Asp Leu Leu Glu Gln Lys Arg Ala Ala Val Asp Thr Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Lys Asp Ile Leu Glu Asp Glu Arg Ala Ala Val Asp Thr Tyr Cys
1               5                   10                  15

<210> SEQ ID NO 8
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 8

Lys Asp Ile Leu Glu Asp Glu Arg Ala Ala Val Asp Thr Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Asp Leu Leu Glu Gln Arg Arg Ala Glu Val Asp Thr Tyr Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Lys Asp Leu Leu Glu Gln Arg Arg Ala Ala Val Asp Thr Tyr Cys
1               5                   10                  15

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Gln Lys Arg Leu Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gln Lys Cys Leu Ala
1               5

<210> SEQ ID NO 13
<211> LENGTH: 5
<212> TYPE: PRT
<213> ORGANISM: Escherichia coli
<220> FEATURE:
<221> NAME/KEY: MISC_FEATURE
<222> LOCATION: (2)..(2)
<223> OTHER INFORMATION: The residue at this position is dLys.

<400> SEQUENCE: 13

Gln Lys Arg Ala Ala
1               5

<210> SEQ ID NO 14
<211> LENGTH: 5
```

<212> TYPE: PRT
<213> ORGANISM: Artificial Sequence
<220> FEATURE:
<223> OTHER INFORMATION: Synthetic

<400> SEQUENCE: 14

Gln Lys Arg Ala Glu
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Gln Glu Cys Leu Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

Asp Lys Cys Leu Ala
1               5

<210> SEQ ID NO 17
<211> LENGTH: 169
<212> TYPE: PRT
<213> ORGANISM: Artificial Sequence
<220> FEATURE:
<223> OTHER INFORMATION: Synthetic

<400> SEQUENCE: 17

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Asn Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp His Lys
65                  70                  75                  80

Asp Leu Leu Glu Gln Lys Arg Ala Ala Val Asp Thr Tyr Cys Val Asp
                85                  90                  95

Pro Ile Ser Arg Asp Leu Val Val Ser Tyr Val Asn Thr Asn Met Gly
            100                 105                 110

Leu Lys Phe Arg Gln Leu Leu Trp Phe His Ile Ser Cys Leu Thr Phe
        115                 120                 125

Gly Arg Glu Thr Val Ile Glu Tyr Leu Val Ser Phe Gly Val Trp Ile
    130                 135                 140

Arg Thr Pro Pro Ala Tyr Arg Pro Pro Asn Ala Pro Ile Leu Ser Thr
145                 150                 155                 160

Leu Pro Ala Trp Ala Arg Val Ile Asn
                165

<210> SEQ ID NO 18
<211> LENGTH: 169
<212> TYPE: PRT
<213> ORGANISM: Artificial Sequence
<220> FEATURE:
<223> OTHER INFORMATION: Synthetic

<400> SEQUENCE: 18

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Asn Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp His Lys
65                  70                  75                  80

Asp Ile Leu Glu Asp Glu Arg Ala Ala Val Asp Thr Tyr Cys Val Asp
                85                  90                  95

Pro Ile Ser Arg Asp Leu Val Val Ser Tyr Val Asn Thr Asn Met Gly
            100                 105                 110

Leu Lys Phe Arg Gln Leu Leu Trp Phe His Ile Ser Cys Leu Thr Phe
        115                 120                 125

Gly Arg Glu Thr Val Ile Glu Tyr Leu Val Ser Phe Gly Val Trp Ile
    130                 135                 140

Arg Thr Pro Pro Ala Tyr Arg Pro Pro Asn Ala Pro Ile Leu Ser Thr
145                 150                 155                 160

Leu Pro Ala Trp Ala Arg Val Ile Asn
                165
```

<210> SEQ ID NO 19
<211> LENGTH: 54
<212> TYPE: DNA
<213> ORGANISM: Artificial Sequence
<220> FEATURE:
<223> OTHER INFORMATION: Synthetic

<400> SEQUENCE: 19
cacaaggacc tcctggagca gaagcgggcc gcggtggaca cctactgcgt agat        54

<210> SEQ ID NO 20
<211> LENGTH: 54
<212> TYPE: DNA
<213> ORGANISM: Artificial Sequence
<220> FEATURE:
<223> OTHER INFORMATION: Synthetic

<400> SEQUENCE: 20
cacaaggaca tcctggaaga cgagcgggcc gcggtggaca cctactgcgt agat        54

<210> SEQ ID NO 21
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The amino acid at this position can be lysine, arginine, or histidine.

```
<220> FEATURE:
<221> NAME/KEY: MISC_FEATURE
<222> LOCATION: (3)..(4)
<223> OTHER INFORMATION: The amino acids at these positions can be any
      amino acid.

<400> SEQUENCE: 21

Gln Xaa Xaa Xaa Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Gln Arg Ala Cys Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Gln Lys Arg Ala Ala Cys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Cys Gln Lys Arg Ala Ala
1               5

<210> SEQ ID NO 25
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is selected
      from the group of amino acids consisting of alanine, valine,
      isoleucine, serine, threonine and asparagine.

<400> SEQUENCE: 25

Gln Arg Xaa Xaa Ala
1               5

<210> SEQ ID NO 26
<211> LENGTH: 5
<212> TYPE: PRT
<213> ORGANISM: Escherichia coli
<220> FEATURE:
```

```
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is selected
      from the group of amino acids consisting of alanine, valine,
      isoleucine, serine, threonine and asparagine.

<400> SEQUENCE: 26

Gln Lys Xaa Xaa Ala
1               5

<210> SEQ ID NO 27
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: The amino acid at this position is selected
      from the group of amino acids consisting of alanine, valine,
      leucine, isoleucine, serine, threonine and asparagine.
<220> FEATURE:
<221> NAME/KEY: MISC_FEATURE
<222> LOCATION: (4)..(4)
<223> OTHER INFORMATION: The amino acid at this position is 2 is
      selected from the group of amino acids consisting of alanine,
      valine, isoleucine, serine, threonine and asparagine.

<400> SEQUENCE: 27

Gln His Xaa Xaa Ala
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Lys Asp Leu Leu Glu Gln Arg Arg Ala Ala Val Asp Thr Tyr
1               5                  10

<210> SEQ ID NO 29
<211> LENGTH: 417
<212> TYPE: PRT
<213> ORGANISM: Artificial Sequence
<220> FEATURE:
<223> OTHER INFORMATION: Synthetic

<400> SEQUENCE: 29

Met Leu Leu Ser Val Pro Leu Leu Gly Leu Leu Gly Leu Ala Val
1               5                  10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Lys Asp Lys
        50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
```

-continued

```
                 85                  90                  95
Val Lys His Glu Gln Asn Ile Asp Cys Gly Gly Tyr Val Lys Leu
            100                 105                 110
Phe Pro Asn Ser Leu Asp Gln Thr Asp Met His Gly Asp Ser Glu Tyr
            115                 120                 125
Asn Ile Met Phe Gly Pro Asp Ile Cys Gly Pro Gly Thr Lys Lys Val
130                 135                 140
His Val Ile Phe Asn Tyr Lys Gly Lys Asn Val Leu Ile Asn Lys Asp
145                 150                 155                 160
Ile Arg Cys Lys Asp Asp Glu Phe Thr His Leu Tyr Thr Leu Ile Val
                165                 170                 175
Arg Pro Asp Asn Thr Tyr Glu Val Lys Ile Asp Asn Ser Gln Val Glu
            180                 185                 190
Ser Gly Ser Leu Glu Asp Asp Trp Asp Phe Leu Pro Pro Lys Lys Ile
            195                 200                 205
Lys Asp Pro Asp Ala Ser Lys Pro Glu Asp Trp Asp Glu Arg Ala Lys
210                 215                 220
Ile Asp Asp Pro Thr Asp Ser Lys Pro Glu Asp Trp Asp Lys Pro Glu
225                 230                 235                 240
His Ile Pro Asp Pro Asp Ala Lys Lys Pro Glu Asp Trp Asp Glu Glu
                245                 250                 255
Met Asp Gly Glu Trp Glu Pro Pro Val Ile Gln Asn Pro Glu Tyr Lys
            260                 265                 270
Gly Glu Trp Lys Pro Arg Gln Ile Asp Asn Pro Asp Tyr Lys Gly Thr
            275                 280                 285
Trp Ile His Pro Glu Ile Asp Asn Pro Glu Tyr Ser Pro Asp Pro Ser
290                 295                 300
Ile Tyr Ala Tyr Asp Asn Phe Gly Val Leu Gly Leu Asp Leu Trp Gln
305                 310                 315                 320
Val Lys Ser Gly Thr Ile Phe Asp Asn Phe Leu Ile Thr Asn Asp Glu
                325                 330                 335
Ala Tyr Ala Glu Glu Phe Gly Asn Glu Thr Trp Gly Val Thr Lys Ala
            340                 345                 350
Ala Glu Lys Gln Met Lys Asp Lys Gln Asp Glu Glu Gln Arg Leu Lys
            355                 360                 365
Glu Glu Glu Glu Asp Lys Lys Arg Lys Glu Glu Glu Glu Ala Glu Asp
            370                 375                 380
Lys Glu Asp Asp Glu Asp Lys Asp Glu Asp Glu Glu Asp Glu Glu Asp
385                 390                 395                 400
Lys Glu Glu Asp Glu Glu Glu Asp Val Pro Gly Gln Ala Lys Asp Glu
                405                 410                 415
Leu
```

<210> SEQ ID NO 30
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino acid.
<220> FEATURE:
<221> NAME/KEY: MISC_FEATURE
<222> LOCATION: (7)..(7)
<223> OTHER INFORMATION: The residue at this position can be any amino acid.

-continued

```
<400> SEQUENCE: 30

Xaa Gln Arg Arg Ala Glu Xaa
1               5

<210> SEQ ID NO 31
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 31

Xaa Gln Arg Arg Ala Ala Xaa
1               5

<210> SEQ ID NO 32
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 32

Xaa Gln Arg Arg Thr Ala Xaa
1               5

<210> SEQ ID NO 33
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 33

Xaa Gln Lys Arg Leu Ala Xaa
1               5

<210> SEQ ID NO 34
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
```

-continued

```
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 34

Xaa Gln Lys Cys Leu Ala Xaa
1               5

<210> SEQ ID NO 35
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 35

Xaa Gln Lys Arg Ala Ala Xaa
1               5

<210> SEQ ID NO 36
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: The residue at this position can be any amino
      acid.
<220> FEATURE:
<221> NAME/KEY: MISC_FEATURE
<222> LOCATION: (7)..(7)
<223> OTHER INFORMATION: The residue at this position can be any amino
      acid.

<400> SEQUENCE: 36

Xaa Asp Glu Arg Ala Ala Xaa
1               5
```